United States Patent [19]

Veech

[11] Patent Number: 4,663,166

[45] Date of Patent: May 5, 1987

[54] ELECTROLYTE SOLUTIONS AND IN VIVO USE THEREOF

[76] Inventor: Richard L. Veech, 712 Brent Rd., Rockville, Md. 20850

[21] Appl. No.: 748,232

[22] Filed: Jun. 24, 1985

Related U.S. Application Data

[63] Continuation-in-part of Ser. No. 623,510, June 22, 1984, abandoned.

[51] Int. Cl.[4] .................... A61K 31/19; A61K 31/70; A61K 33/14; A61K 33/25
[52] U.S. Cl. .................................. 424/146; 424/153; 514/23; 514/557
[58] Field of Search ....................... 424/153, 180, 146; 514/23, 557

[56] References Cited

U.S. PATENT DOCUMENTS

| | | | |
|---|---|---|---|
| 3,970,750 | 6/1976 | Brockemeyer et al. | 424/153 |
| 3,993,750 | 11/1976 | Fox | 424/153 |

FOREIGN PATENT DOCUMENTS

| | | |
|---|---|---|
| WO86/239 | 1/1986 | PCT Int'l Appl. |
| WO86/227 | 1/1986 | PCT Int'l Appl. |
| WO86/228 | 1/1986 | PCT Int'l Appl. |
| WO86/335 | 1/1986 | PCT Int'l Appl. |

OTHER PUBLICATIONS

Physicians' Desk Reference, 28th Ed. (1974), p. 125.
Latta, T., (1832), Malignant Cholera. Documents . . . Relative to the Treatment of Cholera by Copious Injection of Aqueous & Saline Fluids into the Veins, *Lancet* ii; 272-277.
Ringer, S., (1883), A Further Contribution Regarding the Influence of the Different Constituents of the Blood on the Contraction of the Heart, *J. Physiol* 4: 29-42.
Hartman, A. F., (1934), Theory & Practice of Parenteral Fluid Administration, *JAMA* 103: 1349-1354.
Locke, F. S., (1900), Die Wirkung der Metalle des Blutplasma & Verschiedener Zucker auf das Isolirte Saugerthierherz, *Zentrablatt fuer Physiologie* 14: 670-673.
Tyrode M.N., (1910), The Mode of Action of Some Purgative Salts, *Arch. Int. Pharmacedyn.* 20: 205-223.
Krebs H. A., Henseleit, K., (1932), Untersuchugen uber die Harnstoffbildung im Tierkorper, *Hoppe-Seyler's Z Physiol. Chem.* 210: 33-66.
Krebs, H. A., (1950), Body Size & Tissue Respiration, *Biochem. Biophys. Acta* 4: 249-269.
Dawson, A. M. C., Elliott, D., Elliott, W. H., Jone, K. M., (1969), Data for Biochemical Research 2nd Ed. Clarendon Press, Oxford, pp. 507, "Physiological Media".
Fox, Ch, Winfield, J. M., Slobody, L. B., Swindler C. M., Lattimer, J. K., (1952), Electrolyte Solution Approximating Plasma Concentrations with Increased Potassium for Routine Fluid & Electrolyte Replacement. *JAMA* 148: 827-833.
Mion, C. M., Hegstrom, R. M., Boen St, Scribner B. H., (1964), Substitution of Sodium Acetate for Sodium Bicarbonate in the Bath for Hemodialysis, *Trans. Amer. Soc. Artif. Int. Organs* 10: 110-113.
Parsons, F. M., Stewart, W. K., (1983), The Composition of Dialysis Fluid, In: Replacement of Renal Function by Dialysis, 2nd Ed. (Drukker, W., Parsons, F. M., Maher, J. F. eds), Martinus Nijhoff, Higham, pp. 148-170.
Facts and Comparisons, Oct. 1981-Aug. 1983. J. B. Lippincott; St. Louis 35d-53.
Documenta Geigy Scientific Tables (1962, Essellier, A. F., Jeanneret, P., Aqueous Solutions—Parenteral Infusion Therapy, pp. 331-334, Geigy Pharmaceutical Co., Ltd., Manchester.
Veech, R. L., Eggleston, L. V., Krebs, H. A., (1969), The Redox State of Free Nicotin Amide-Adenine Dinucleotide Phosphate in the Cytoplasm of Rat Liver *Biochem. J.* 115: 609-619.
Veech, R. L., Lawson, J. W. R., Cornell, N. W., Krebs, H. S., (1979), Cytosolic Phosphorylation Potential *J. Biol. Chem.* 254: 6538-6547.
Veech, R. L., Cook, G. A., King, M. T., (1980), Relationship of Free Cytoplasmic Pyrophosphate to Liver Glucose Content & Total Pyrophosphate to Cytoplasmic Phosphorylation Potential, *FEBS Lett.* 117: K65-K72.
Sistare, F. D., Haynes, R. C., Jr., (1985), The Interaction Between the Cytosolic Pyridine Mucleotide Redox Potential & Gluconeogenisis from Lactate/Pyruvate in Isolated Rat Hepatocytes, *J. Biol. Chem.* 260: 12748-12753.
Sistare, F. D., Haynes, R. C., Jr. (1985), Acute Stimulation by Gluconeogenisis from Lactate/Pyruvate in Isolated Hepatocytes from Normal and Adrenolectonized Rats, *J. Biol. Chem.* 260: 1254-12760.
Veech, R. L., (1986), The Toxic Impact of Parenteral Fluid Therapy, *J. Clin. Nutr.* (In Press).
Tauford, C. S., (1950), *J. Am. Chem. Soc.* 72: 441-451, Preparation & Properties of Serum Plasma Proteins, XXIII, Hydrogen Ion Equilibria in Nature & Modified Human Serum Albumin.

*Primary Examiner*—Stanley J. Friedman

[57] ABSTRACT

Electrolyte solutions are provided which are useful in electrolyte and fluid therapy, parenteral nutrition, and dialysis. The Na:Cl ratio is normalized, plasma and cellular pH are normalized, and cellular cofactor ratios are normalized, in a manner which decreases toxicity over prior art solutions. The solutions employ at least one of the following near-equilibrium couples: (a) bicarbonate/$CO_2$; (b) 1-lactate/pyruvate; and (c) d-betahydroxybutyrate/acetoacetate.

15 Claims, No Drawings

4,663,166

ELECTROLYTE SOLUTIONS AND IN VIVO USE THEREOF

RELATED APPLICATION

This application is a continuation-in-part of U.S. Ser. No. 623,102 filed June 22, 1984, now abandoned.

BACKGROUND OF INVENTION

1. Field of the Invention

This invention lies in the field of in vivo techniques and compositions for replenishing fluid electrolytes and nutrients while regulating metabolic processes in living mammals.

2. State of the Art

The vital functions of highly developed organisms are closely dependent on the internal aqueous medium and on the maintenance in it of extreme constancy of chemical and physical properties.

It has long been recognized that all animal intracellular and extracellular body fluids contain inorganic electrolytes, and that these electrolytes are involved in, and profoundly influence, various life processes. Attempts to make artificial electrolyte fluids which may bathe tissues or be administered to the human blood stream have been known since about 1880, and, although modern analytical tools and procedures have clarified compositional details of blood electrolytes, the use of various aqueous electrolyte solutions for in vivo purposes in human medicine and related fields has been extent for approximately one hundred years.

Those inorganic electrolytes characteristically found in normal human blood serum at respective concentration levels above about 1 millimolar per liter of concentration are shown below in Table I. Also, for comparative purposes, in Table I are shown some representative compositions of various aqueous electrolyte solutions that have been previously prepared and used for in vivo purposes. In general, the philosophy behind the formulation of aqueous electrolyte solutions for in vivo use has been that such should mimic or closely resemble the chemical composition of electrolytes in blood and plasma. An electrolyte is a substance (usually a salt, acid or base) which in solution dissociates wholly or partly into electrically charged particles known as ions (the term is also sometimes used in the art to denote the solution itself, which has a high electrical conductivity than the pure solvent, e.g. water). The positively charged ions are termed cations while the negatively charged ions are termed anions. Strong and weak electrolytes are recognized. The dissociation of electrolytes is very markedly dependent on concentration; it increases with increasing dilution of the solution. The ions can be regarded as molecules in electrolyte solutions. Because of dissociation considerations, the term "sigma" or the greek letter for sigma ("$\Sigma$") is sometimes employed herein as a prefix to designate the total presence of a specified material, such as an electrolyte, whether or not all of the material is in an ionic form complexed with a heavy metal, or regardless of charge on the material in a given solution. A pair of brackets ([]) indicates the free concentration of the substance indicated as opposed to that bound to tissue components, such as proteins.

TABLE I

Prior Art

Class 1a / Class 1b / Class 1c

| Units mmoles L fluid | Normal Plasma N.E.J.M. 283, 1285 1970 | 1.a.1 Normal 0.9% Saline U.S. | Class 1d | 1.a.2 Normal 0.95% Saline U.K. | 1.a.3 Isotonic Na Lactate, Salt | 1.b.1 Isotonic NaHCO₃⁻, Salt | 1.c.1 5% Dextrose in H₂O, U.S. | 1.c.2 5.25% Dextrose in H₂O, U.K. | 1.c.3 Isotonic Glucose 2 NaCl 1 | 1.c.4 Glucose + Na Lactate + NaCl | 1.c.10 D-5-W 0.9% NaCl | 1.c.11 10% Glucose + 0.9% NaCl | 1.c.12 2.5% Glucose 0.45% NaCl | 1.c.13 5% Fructose in Electrolyte 75 |
|---|---|---|---|---|---|---|---|---|---|---|---|---|---|---|
| Na | 136–145 | 155 | | 162.5 | 160.3 | 160.3 | | | 54.1 | 53.4 | 154 | 154 | 77 | 40 |
| K | 3.5–5.0 | | | | | | | | | | | | | 35 |
| Ca | 2.1–2.6 | | | | | | | | | | | | | |
| free [Ca²⁺] | [1.06] | | | | | | | | | | | | | |
| Mg | 0.75–1.25 | | | | | | | | | | | | | |
| free [Mg²⁺] | [0.53] | | | | | | | | | | | | | |
| Σ mEq Cations | 142.7–153.2 | 155 | | 162.5 | 160.3 | 160.3 | 0 | 0 | 54.1 | 53.4 | 154 | 154 | 77 | 75 |
| Cl | 100–106 | 155 | | 162.5 | 108.3 | 108.3 | | | 54.1 | 36.1 | 154 | 154 | 77 | 47.5 |
| HCO₃ | 26–28 | | | | | 52 | | | | | | | | |
| Σ Pi | 1–1.45 | | | | | | | | | | | | | 7.5H₂PO₄⁻ |
| SO₄ | 0.32–0.94 | | | | | | | | | 17.3 (d.l) | | | | |
| L-lactate | 0.6–1.8 | | | | 52.0 (d.l) | | | | | | | | | 20 (d.l) |
| pyruvate | | | | | | | | | | | | | | |
| Lact/pyr | | | | | ∞ | | | | | ∞ | | | | ∞ |
| D B OHbutyrate | | | | | | | | | | | | | | |
| acetoacetate | | | | | | | | | | | | | | |
| B HB/acac | | | | | | | | | | | | | | |
| acetate | | | | | | | | | | | | | | |
| Other | | | | | | | | | | | | | | |
| Σ mEq anions | 128.7–139.4 | 155 | | 162.5 | 160.3 | 160.3 | 0 | 0 | 54.1 | 53.4 | 154 | 154 | 77 | 75 |
| Na/Cl | 1.28–1.45 | 1.00 | | 1.00 | 1.48 | 1.48 | | | 1.00 | 1.48 | 1.00 | 1.00 | 1.00 | 0.84 |
| Glucose or others | 3.9–5.6 | | | | | | 278 | 292 | 195 | 195 | 278 | 556 | 139 | 278 (Fructose) |
| CO₂ | 0.99–1.39 | | | | | 8.6 | | | | | | | | |
| pH | 7.35–7.45 | 5.5–6.5 | | 5.5–6.5 | ~6.5 | | ~6.5 | ~6.5 | ~6.5 | ~6.5 | ~5.5–6.5 | ~5.5–6.5 | ~5.5–6.5 | |
| Σ mOsa | 285–295 | 310 | | 325 | 321 | 321 | 278 | 292 | 301 | 302 | 564 | 813 | 293 | 428 |
| Use: | | | | | | | | | | | | | | |

Prior Art

Class 2a

| Units mmole L fluid | Normal Plasma N.E.J.M. 283, 1285 1970 | 2.a.1. Ringer's Injection U.S. | 2.a.2. Lactated Ringer's | 2.a.3 Lactated Ringer's (Commercial) | 2.a.4. Acetated Ringer's U.S. | 2.a.5 Lact/Acet Ringer's | 2.a.10 Ionosol D-CM (Abbott) | 2.a.11 Plasmalyte (Travenol) | 2.a.12. Isolyte S (McGaw) Polyionic 148 (Cutter) | 2.a.13. Isolyte E (McGaw) | 2.a.14. Delbecco's Phosphate Saline | 2.a.15. Kreb's Ringer Phosphate | 2.b.1. Krebs Henseleit |
|---|---|---|---|---|---|---|---|---|---|---|---|---|---|
| Na | 136–14 | 147 | 129.8 | 130 | 130 | 140 | 138 | 140 | 140 | 140 | 152.2 | 150.76 | 143 |
| K | 3.5–5.0 | 4 | 5.4 | 4 | 4 | 10 | 12 | 10 | 5 | 10 | 4.17 | 5.92 | 5.9 |
| Ca | 2.1–2.6 | 2.5 | 0.9 | 1.5 | 1.5 | 2.5 | 2.5 | 2.5 | | 2.5 | 0.9 | 2.54 | 2.5 |
| free [Ca²⁺] | [1.06] | | | | | | | | | | | | |
| Mg | 0.75–1.25 | | 1.0 | | | 1.5 | 1.5 | 1.5 | 1.5 | 1.5 | 0.49 | 1.18 | 1.2 |
| free [Mg²⁺] | [0.53] | | | | | | | | | | | | |
| Σ mEq Cations | 142.7–153.2 | 156 | 139 | 137 | 137 | 158 | 158 | 158 | 148 | 2,158 | 159.15 | 164.12 | 156.3 |
| Cl | 100–106 | 156 | 111.8 | 109 | 109 | 103 | 108 | 103 | 98 | 103 | 140 | 131.51 | 127.8 |
| HCO₃ | 26–28 | | | | | | | | | | | | 25 |

TABLE I-continued

| | | | | | | | | | | | |
|---|---|---|---|---|---|---|---|---|---|---|---|
| Σ Pi | 1-1.45 | | | | | | | | | 9.83 | 17.38 | 1.18 |
| SO4 | 0.32-0.94 | | | | | | | | | 0.48 | 2.36 | 1.18 |
| L-lactate | 0.6-1.8 | | | 27.8 (d,l) | 28 (d,l) | | 27.5 (d,l) | 50 (d,l) | 8 (d,l) | | | |
| pyruvate | | | | | | | | | | | | |
| Lact/pyr | | | | ∞ | ∞ | | ∞ | ∞ | ∞ | | | |
| D B OHbutyrate | | | | | | | | | | | | |
| acetoacetate | | | | | | | | | | | | |
| B HB/acac | | | | | | | | | | | | |
| acetate | | | | | | 28 | 27.5 | | | | | |
| Other | | | | | | | | 47 | | 27 | | |
| | | | | | | | | | | 23 (gluconate) | 4 citrate | 49 |
| Σ mEq anions | 128.7-139.4 | | 156 | 139 | 137 | | 158 | 158 | 158 | 159.18 | 165.15 | 157.3 |
| Na/Cl | 1.28-1.45 | | 0.94 | 1.16 | 1.19 | | 1.36 | 1.28 | 1.36 | 1.08 | 1.15 | 1.12 |
| Glucose or others | 3.9-5.6 | | | | | | | | | | | |
| CO2 | 0.99-1.39 | | | | | | | | | | | 1.24 |
| pH | 7.35-7.45 | | | | | | | | | 7.4 | 7.4 | 7.4 |
| Σ mOsa | 285-295 | | 309 | 276 | 272 | 272 | 312 | 312 | 312 | 308 | 311.16 | 308 |
| Use: | | | I.V. fluid | I.V. fluid | I.V. fluid | I.V. fluid | I.V. fluid | I.V. electrolyte therapy | I.V. electrolyte therapy | Usually tissue culture, sometimes cardiac surgery | Biochemical experiments | Multiple Biochemical Uses |

| | | Prior Art | | | | | | | | | | |
|---|---|---|---|---|---|---|---|---|---|---|---|---|
| | | Class 2c | | | | | | | Class 2d | | | |
| Units mmoles L fluid | Normal Plasma N.E.J.M. 283, 1285 1970 | 2. c. 1 Lactated Ringer's + 5% Glucose | 2. c. 2 ½ Strength Lact-Ringer + 2.5% Glucose | 2. c. 3. Acetated Ringer's + Glucose | 2. c. 4. Ionosol B + 5% Glucose (Abbott) | 2. c. 5. Dianeal + 1.5% Glucose (Travenol) | 2. c. 6. Peritoneal Dialysis + 4.25% Glucose (Am. McGaw) | 2. c. 7. Dianeal K14 + 4.25% Glucose (Travenol) | 2. d. 1 Krebs Serum Substitute | 2. d. 2 Tyrode's Solution 1 (Schimassek) | 2. d. 3. Tyrode's Solution | 2. d. 4. Locke's Solution |
| Na | 136-145 | 130 | 65 | 130 | 57 | 141 | 141.5 | 132 | 141 | 151.54 | 150.1 | 157.57 |
| K | 3.5-5.0 | 4 | 2 | 4 | 25 | | | 4 | 5.93 | 5.9 | 5.9 | 3.57 |
| Ca | 2.1-2.6 [1.06] | 1.5 | 0.75 | 1.5 | | 1.75 | 2.0 | 1.875 | 2.54 | 1.8 | 1.8 | 2.16 |
| free [Ca2+] | | | | | | | | | | | | |
| Mg | 0.75-1.25 [0.53] | | | | 2.5 | 0.75 | 0.75 | 0.75 | 1.18 | 0.45 | 0.45 | 0 |
| free [Mg2+] | | | | | | | | | | | | |
| Σ mEq Cations | 142.7-153.2 | 137 | 68.5 | 137 | 87 | 146 | 147 | 141 | 154.37 | 162.07 | 160.5 | 165.46 |
| Cl | 100-106 | 109 | 55 | 109 | 49 | 101 | 102.5 | 106 | 104.8 | 147.48 | 147.48 | 163.92 |
| HCO3 | 26-28 | | | | | | | | 24.9 | 11.9 | 11.9 | 3.57 |
| Σ Pi | 1-1.45 | | | | 6.5 H2PO4− | | | | 1.23 | 1.22 | 1.22 | — |
| SO4 | 0.32-0.94 | | | | | | | | 2.36 | | | |
| L-lactate | 0.6-1.8 | 28 (d,l) | 14 (d,l) | | 25 (d,l) | 45 (dl) | | 35 (d,l) | | 1.33 | | |
| pyruvate | | | | | | | | | | 0.09 | | |
| Lact/pyr | | ∞ | ∞ | | ∞ | ∞ | | ∞ | 4.9 | 14.8 | | |
| D B OHbutyrate | | | | | | | | | | | | |
| acetoacetate | | | | | | | | | | | | |
| B HB/acac | | | | | | | | | | | | |
| acetate | | | | 28 | | | 44.5 | | | | | |
| Other | | | | | | | | | 2.45 glutamate−<br>5.4 fumarate2− | | | |

TABLE I-continued

| | | | | | | | | | | | |
|---|---|---|---|---|---|---|---|---|---|---|---|
| Σ mEq anions | 128.7–139.4 | 137 | 69 | 137 | 87 | 146 | 147 | 141 | 154.47 | 162.81 | 161.6 | 167.49 |
| Na/Cl | 1.28–1.45 | 1.19 | 1.18 | 1.19 | 1.16 | 1.40 | 1.38 | 1.25 | 1.35 | 1.03 | 1.02 | 0.96 |
| Glucose or others | 3.9–5.6 | 278 | 139 | 278 | 278 | 83 | 236 | 236 | 9.2 | 5.45 | 5.6 | 5.6–13.7 |
| CO$_2$ | 0.99–1.39 | | | | | | | | 1.0 | 1.17 | | |
| pH | 7.35–7.45 | | | | | ~5.5–6.5 | ~5.5–6.5 | ~5.5–6.5 | 7.4 | 7.1 | 7.1 | ? |
| Σ mOsa | 285–295 | 524 | 263 | 523 | 443 | 366 | 510 | 494 | 308.2 | 328 | 318.3 | 336 |
| Use: | | I.V. fluid nutrition & electrolytes | I.V. fluid for dehydration | same as 2. c. l. | Parenteral Nutrition | Peritoneal Dialysis | Peritoneal Dialysis | Peritoneal Dialysis | Artificial Serum for Tissue Slices | Liver Perfusion | Normal Na/Cl | |

Class 1a Solutions Containing 1 or 2 Cations, no Nutrients and No HCO$_3^-$/CO$_2$ 1. a. 1. Most common U.S. I.V. electrolyte solution, Merck Manual. Causes hyperchloremic acidosis with Na/Cl = 1.00. See Black DAK. Lancet i, 353, 1952.
1. a. 2. Used as "normal" saline in U.K. and Canada. Geigy Handbook.
1. a. 3. Darrow et al. J. Am. Med. Ass. 143: 365, 432, 1944. Normal Na/Cl ratio but causes abnormalities.

Class 1b. Solutions Containing 1 or 2 Cations, HCO$_3^-$, and No Nutrients.

1. b. 1. Darrow et al. J. Am. Med. Ass. 143: 365, 432, 1944. Use of bicarbonate alone to correct Na/Cl ratio gives a solution with an abnormal pH, and one which will cause Ca$^{2+}$ or Mg$^{2+}$ added to the solution to precipitate as MgCO$_3$ or CaCO$_3$, is the common alternative to Na lactate, salt; 1. a. 3.

Class 1c Solutions Containing 1 or 2 Cations, with Non-ionic Nutrients. Typically 2.5%, 5%, 10%, 20%, Glucose or Fructose in the U.S. and 2.62%, 5.25%, 10.5%, 20% Glucose or Fructose in the U.K.

1. c. 1. Most used I.V. solution in the U.S. Merck Handbook, 1966, p. 1867. This is combined with NaCl in varying proportions so long as the osmolarity is not below 270 mOsa.
1. c. 2. Same solution in the U.K., where "isotonic" differs. Geigy Handbook, 1970, p. 334.
1. c. 3. Geigy Handbook, 1970, p. 334, has Na/Cl = 1.00
1. c. 4. Geigy Handbook, 1970, p. 334, has reasonable Na/Cl ratio but induces an abnormal redox state.
1. c. 5. Fox et al. J. Am. Med. Ass. 148: 827, 1952.
1. c. 10. throught 1. c. 12. See Facts and Comparisons p. 51, Oct. '81, Lippincott
1. c. 13. Facts and Comparisons p. 52, Aug. '83, Lippincott. Used in parenteral nutrition.

Class 1d Solutions Containing 1 or 2 Cations, Nutrients, and HCO$_3^-$/CO$_2$. None in prior art.

Class 2a Electrolyte Fluids Containing 3 or 4 Cations Suitable for Contacting Cells, Containing No HCO$_3^-$/CO$_2$ and No Glucose or Other Non-Ionic Nutrients.

2. a. 1. Facts and Comparisons p 50, Oct '81, Lippincott
2. a. 2. Hartmann AF. J. Am. Med. Ass. 103: 1349, 1934.
2. a. 3. Facts and Comparisons p 50, Oct '81, Lippincott.
2. a. 4. Facts and Comparisons p 50, Oct '81, Lippincott.
2. a. 5. Facts and Comparisons p 50, Oct '81, Lippincott.
2. a. 10. Facts and Comparisons p 50, Oct '81, Lippincott.
2. a. 11. Facts and Comparisons p 50, Oct '81, Lippincott.
2. a. 12. Facts and Comparisons p 50, Oct '81, Lippincott.
2. a. 13. Facts and Comparisons Oct, 1981, p. 50, Lippincott, St. Louis
2. a. 14. Delbecco R, Vogt M. J Exp Med 1954: 99: 167-182
2. a. 15. Krebs HA. Hoppe S 2 Physiol Chem 1953: 217: 193

Class 2b Solutions Containing 3 or 4 Cations, HCO$_3^-$/CO$_2$ and No Glucose or Other Non-Ionic Nutrients.

2. b. 1. Krebs HA, Henseleit K. Hoppe-Seyle's 2 Physiol Chem 1932; 210: 33–66. This is the second major advance in fluids after S. J. Ringer, Physiol 1883; 4: 29, 223. This fluid became the basis for most tissue culture "balanced salt mixtures", was used in dialysis. It is known to contain twice too much Ca and Mg. It also has an abnormal Na/Cl ratio which Krebs himself unsuccessfully attempted to correct in 1950. (See Krebs HA. B B A 1950;
4: 249–269, or Table I class 2d.)

Class 2c Solutions Containing 3 or 4 Cations, No HCO$_3^-$/CO$_2$ to Which is Added Non-Ionic Nutrients.

2. c. 1. Multiple Manufacterer's. Facts and Comparisons p. 52, Oct 81
2. c. 2. Multiple Manufacterer's Facts and Comparisons p 52, Oct 81
2. c. 3. Multiple Manufacterer's Facts and Comparisons p 52, Oct 81
2. c. 4. (Abbott) Facts and Comparisons p 52b, Aug '83
2. c. 5. (Travenol) Facts and Comparisons p 704, Oct '82
2. c. 6. (American McGaw) Facts and Comparisons p 704, Oct '82

TABLE I-continued 2. c. 7. (Travenol) Facts and Comparisons p 704, Oct '82
Class 2d Solutions Containing 3 or 4 Cations, Plus Non-Ionic Nutrients and $HCO_3^-/CO_2$ 2. d. 1. Krebs HA, B.B.A. 4: 249–269, 1950. Not used in vivo but presented for comparison of composition.
2. d. 2. Tyrodes's solution as modified for liver perfusion by Schimassek H, Biochem Z 336: 460, 1963. Not used in vivo but presented to show prior art in composition. Same for 2. d. 3, Tyrode's, and 2. d. 4, Locke's.
2. d. 3. Tryrode MV, Arch Int Pharmacodya Ther 20: 205–223, 1910.
2. d. 4. Locke FS, Zeatbl Physiol 14: 670–672, 1900.

Contemporarily, a large number of different aqueous electrolyte solutions are prepared, sold in commerce, and used as in vivo fluids, such as for electrolyte and fluid replacement, parenteral nutrition, and dialysis (both hemo-and peritoneal).

Even a cursory examination of Table I will confirm the medical dicta that "plasma is an unmakable solution". The solutions listed in Table 1 illustrate this belief. The essential problem is that plasma contains, in addition to major inorganic electrolytes, trace quantities of various electrolytes plus various metabolites including plasma proteins. In practice, it has not been possible to construct synthetically a replication of plasma because of it complexity. Blood, extracellular fluid, and even plasma can be regarded as tissues.

In most prior art electrolyte solutions, the concentration of chloride anions ($Cl^-$) is higher than in human plasma or serum. For example, the Krebs Henseleit solution (see Table I) contains a concentration of $Cl^-$ which is about 20% higher than in human serum. This anion gap, that is, the difference between the positive cations and the negative anions, is now known to be due largely to the anionic metabolites in normal plasma plus the contribution of acidic amino acid groups found on plasma proteins. Referring to Table I, it is seen that the total positive cations in plasma is 142-154 meq/l while the total anions is only about 128-137 meq/l leaving a deficit of about 14-17 meq/l of anions. For convenience, the anion gap in human plasma can be expressed as the ratio of sodium cation milliequivalents per liter to chloride anion milliequivalents per liter.

From Table I, it is clear that the Krebs Serum substitute (Krebs, H. A. *Biochem. Biophys. Acta* 4, 249–269, 1950) comes closest to approximating the electrolyte composition of human plasma. In this solution, Krebs attempted to correct the excessive $Cl^-$ content in Krebs Henseleit solution (*Hoppe-S Z. Physiol. Chem.* 210, 33–66, 1932) using metabolic experiments with tissue slices. Because of the law of electrical neutrality, $Na^+$ cannot be added to a solution without some anion (such as $Cl^-$) being added also; the sum of cations and anions must be equal in any solution. In his 1950 attempt, Krebs chose pyruvate$^-$, 1—-glutamate$^-$, and fumarate$^{2-}$ as anions to be added.

An alternative to Krebs selection of anions came about at the same time. In 1949, the use of high concentrations of acetate as a metabolizable organic anion was advocated (Mudge G. H. Mannining, J. A. Gilman A.; *Proc. Soc. Exptl. Biol. Med.* 71, 136–138, 1949). This idea led in 1964 to the advocacy of the use of 35–45 mM (millimolar) acetate in commercial hemodialysis fluids (Mion C. M., Hegstrom R. M., Boen S. T., Scribner B. H.; *Trans. Am. Soc. Artif. Internal Organs* 10, 110–113, 1964).

In addition to the above organic anions, the current reference work "Facts and Comparisons" indicates various commercial electrolyte fluids which contain lactate anion.

All of the prior art electrolyte solutions (with or without nutrients) as exemplified in Table I are now believed to lead to undesirable and pathological consequences particularly through extended usage. As regards acetate, editorials recently appearing in the *British Medical Journal,* 287, 308–309, 1983) present evidence that acetate leads to fatigue, nausea, malaise, sudden hypertension, increased atherosclerosis, hypoventilation, and hypoxia. Also, the originator of acetate dialysis now advocates its use only in "healthy" patients (Pagel M. D., Ahmed S, Vizzo J. E. and Scribner B. H.; *Kidney Int.* 21, 513–518, 1982).

Krebs choice of glutamate$^-$ and fumarate$^{2-}$ is incorrect because these anions do not penetrate cell membranes in a predictable manner, but, like citrate$^{3-}$, exhibit severe gradients of six fold or greater between plasma $H_2O$ and cell $H_2O$. The alternate use of d,l-lactate$^-$ (Hartmann AF. *J Am Med Asso* 103 1349–1354, 1934) is now known to induce severe abnormalities, particularly coma at levels far below the 28 to 35 mM d,l-lactate contained in these solutions (Oh MS et al, *N Eng J Med* 301 249 251, 1979; Stolberg L, et al *N Eng J Med* 306: 1344–1348, 1982; Ballabriga A, et al *Helv Paediatr Acta* 25:25–34, 1970) in to the induction severe abnormalities in redox and phosphorylation state induced by the use of 1-lactate alone. The use of gluconate$^-$ induces abnormalities in the hexosemonophosphate pathway. Indeed, all previous used organic ions violate the "safe entry points" or the normal Na:Cl ratio as herein defined.

In addition to the use of d,l-lactate, gluconate, fumarate, glutamate, pyruvate, and citrate anions in current commercially available prior art electrolyte fluids, and wherein such anions are typically employed at levels above those found in the (plasma or serum) of healthy humans, many such prior art commercial fluids also employ high levels of nonionic metabolites, such as fructose and glycerol, which induce separate redox state and phosphorylation potential abnormalities in phosphorylation potential with rapid destruction of liver purine nucleotides and their release into blood sometimes leading to renal shutdown due to uric acid deposition in the kidneys (see Woods H. F., Eggleston L. V. and Krebs H. A.; *Biochem. J.* 119, 501–510, 1970). Fructose in plasma above 0.2 mM must be considered to violate the "safe entry point". Likewise, use of intravenous glycerol at levels above 5 mM/l as currently practiced leads, in tissue containing glycerol kinase, such as kidney and liver, to accumulation of 10 mM glycerol phosphate (over 100 times normal). See Burch H. B. et al.; *J. Biol. Chem.* 257, 3676–3679, 1982).

In addition to failing to solve the anion gap problem (or to provide a normal milliequivalent ratio of sodium cation to chloride anions) without causing profound and adverse physiological effects (including disruption of normal redox state and normal phosphorylation potential), many prior art aqueous electrolyte solutions for in vivo usage fail to have a pH which approximates the pH of mammalian intracellular and extracellular fluids, especially, plasma or serum.

Mammalian systems normally operate at temperatures between about 37°-38° C. where, by common thermodynamic convention, neutral pH is taken to be about 7 at 25 C. It is clear that changes in pH, (the negative log 10 of [$H^+$] concentration) necessarily affect the fundamental energetic relationships occurring in living cells. Also, enzymes have sharply defined ranges of "$H^+$] concentration in which they perform their catalytic functions in a normal manner. Deviation of mammalian plasma pH down to 6.9 or above 7.7 from its normal range of 7.35–7.45 is therefore fatal to most mammalian organisms. Massive changes in the cellular redox and phosphorylation states also disorder cellular homeostasis.

The pH of human plasma is normally maintained by the human body in the range from about 7.35 to 7.45 while the pH of human cellular cytoplasm is about 7.2 (see Veech et al in *J. Biol. Chem.* 254, 6538–6547, 1979).

If blood pH drops to 6.8 in man, then death ensues from cardiac arrest, and if blood pH increases to above pH 7.7, then death ensues from convulsions.

The major chemical system maintaining body pH within this narrow normal range is the $[CO_2]/[HCO_3^-]$ buffer system. The $[CO_2]$ of blood is maintained minute to minute by a portion of the mammalian brain called the respiratory center which senses brain cell pH and adjusts the depth and speed of respiration to change pH by increasing or decreasing $[CO_2]$ according to the famous Henderson Hasselbalch equation (Henderson L. J., *Silliman Lectures, Yale U. Press, New Haven*, 1928).

Even though pH is thus seen to be a critical factor in mammalian blood, many commercial electrolyte solutions as administered have pH values which deviate substantially from normal. Others give excessive $Cl^-$ relative to $Na^+$ which results in hyperchloremic acidosis, (Black D.A.K.; *Lancet i* 305-12, 1953), or give organic anions in a manner which causes measurable deviations from normal in the metabolic processes of the cell. Also, many commercially available electrolyte solutions contain no carbon dioxide which can result in a loss of respiratory drive and consequent hypoxia in patients.

The compositions and methods of the present invention overcome the above indicated prior art problems. These compositions and methods employ definite ratios of $[bicarbonate^-]/[carbon\ dioxide]$, $[1-lactate^-]/[pyruvate^-]$, and $[d-betahydroxybutyrate^-]/[acetoacetate^-]$. Each of these mixtures constitute a near equilibrium couple which is known to be a normal constituent of mammalian plasma. While each of these pairs of components has been previously employed at lease on a laboratory basis in solutions used for animal (mammalian) experiments, these mixture pairs have never previously been used in an electrolyte solution to obtain a normal Na:Cl milliequivalent ratio or to solve the anion gap problem.

All previous electrolyte solutions, and plasma substitutes, induce severe and measurable pathogenic abnormalities and no prior art electrolyte solution or plasma substitute has both (a) employed at least one of the three mixture pairs of this invention and (b) achieved a normal Na:Cl milliequivalent ratio as taught herein. Thus, for example, the Krebs Henseleit solution contains the $[HCO_3^-]/[CO_2]$ buffer system (but contains excessive chloride ions). Schimassek (Schimassek H.; *Bio. Chem. Z*, 336, 460, 1963) added about normal blood levels of lactate and pyruvate to what is essentially Tyrode's solution (see Tyrode, M. J.; *Arch Int. Pharmacodyn* 20, 205, 1910) containing 2.5% albumin in an attempt to create a physiological solution for perfusion. It should be noted that Schimassek added 1.33 mM/L D-L-lactate, which is definitely abnormal (see normal blood lactate levels shown in Table 1). Further, the $Na^+$ of 151 mM/l and $Cl^-$ of 147.5 mM/l in Schimassek's modified Tyrode's solution approximates the concentration of 155 mM/l Na and 155 mM/l Cl in so-called normal (0.9T) saline, the most widely used electrolyte infusion solution, and thus obtained a grossly abnormal Na:Cl milliequivalent ratio of about 1.24–1.45 with a mean of about 1.38. Infusions of electrolyte solutions with a Na:Cl milliequivalent ratio of less than about 1.38 have long been known to cause hyperchloremic acidosis in the treated organism. (See Levinsky N. G. in Harrison's *Textbook of Medicine* pp 230–236, McGraw-Hill, N.Y., 1983). It is the attempt to avoid this problem that leads to the wide use of such solutions as Ringer's lactate or acetate dialysis fluids which overcome the Na:Cl ratio problem, but which in turn create gross abnormalities of other types. It is the attainment of a normal Na:Cl milliequivalent ratio in a manner which avoids the pathological consequences inherent in all currently known or practiced methods which is a major part of the invention herein disclosed.

The making of a Krebs Henseleit electrolyte solution (or other prior art electrolyte solution) and the incorporation thereinto of a mixture of L-lactate and pyruvate anions, or of a mixture of D-betahydroxybutyrate and acetoacetate anions did not, and could not, result in the making of an electrolyte solution wherein the anion gap problem was overcome (or wherein the milliequivalent ratio of sodium cations to chloride anions was normalized), in accordance with the teachings of the present invention, because each of such resulting solutions would still contain excessive chloride anions and so would inevitably cause hyperchloremia if an when used in human or mammalian therapy.

In general summary, the prior art describes a series of electrolyte solutions typically of about 270–320 milliosmoles (or higher) comprised of: (a) 1 to 4 metallic cations of sodium, potassium, magnesium, and calcium in amounts greater than 0.5 mM/L, (b) 1 to 5 inorganic anions of chloride plus also $HPO_4^{2-}$), (c) 0 to several organic carboxylic or bicarbonate anions, (d) 0 to 5 nonionic materials in concentrations of greater than about 0.5 mM/L from the group comprising $CO_2$ gas, glucose, urea, glutamine, and others, and (e) sometimes one or more high molecular weight substances, such as albumin, hemocel, and the like. None of these solutions, for the reasons herein above explained, either normalize the milliequivalent ratio of Na:Cl at all, or normalize this ratio without causing profound and adverse physiological consequences. In the present invention, there are provided processes and compositions of a complex fluid nature for in vivo usage which can substantially completely eliminate all of such prior art problems. While the components of these new solution compositions are known solution components, no one has heretofore formulated the solutions of the present invention which not only tend to achieve a normal plasma milliequivalent ratio of sodium cations to chloride anions, but also tend to achieve a normalization of plasma pH and a normalization of the cellular redox state and the cellular phosphorylation potential. Also, these new solutions permit one to avoid usage of the previously employed carboxylic anions, as acetate, or lactate alone, which cause adverse effects.

BRIEF SUMMARY OF THE INVENTION

This invention relates to processes for accomplishing electrolyte and water therapy while simultaneously normalizing blood composition in a mammal (including man) by introducing in a physiologically effective amount by any means, including parenterally, (intravenously), intra-arterially, intramuscularly, intravascularly, and the like, by dialysis, or orally, and the like into such mammal an aqueous solution wherein:
 (a) the ratio of sodium cation milliequivalents per liter to the chloride anion milliequivalents per liter are so selected as to tend to produce the range found in normal mammalian blood plasma,
 (b) there is a physiologically effective amount of at least one near equilibrium couple selected from the group consisting of
  (1) bicarbonate$^-$ and carbon dioxide, (2) l-lactate⁻ and pyruvate⁻, and
(3) d-betahydroxybutyrate⁻ and acetoacetate⁻, and
(c) the pH ranges from 5 to 9.

This invention further relates to physiologically compatible aqueous salt solutions for mammalian (including human) administration which contain such a ratio of sodium to chloride and which incorporate such near-equilibrium couples(s).

This invention provides electrolytes of the class indicated wherein physiologically normal concentrations of the divalent cations $Mg^{2+}$ and $Ca^{2+}$ may be included without precipitation. No one has previously made solutions for in vivo use which contain the correct $Na^+:Cl^-$ ratio and which also contain the physiologically normal respective amounts of $Mg^{2+}$ and $Ca^{2+}$.

When used for mammalian administration in accord with the present process teachings, such a solution:
(a) tends to maintain and normalize in plasma the milliequivalent ratio of sodium cations to chloride anions in the normal range, and
(b) tends to maintain and normalize plasma pH, and
(c) tends to maintain and normalize the redox state and the phosphorylation potential.

One (first) class of such solutions chracteristically utilizes (contains) an inorganic class of anions comprised of chloride and bicarbonate. These solutions have a physiological pH which is broadly in the range from about 5 to 9, and preferably in the range from about 6.9 to 8.6, and more preferably in the range from about 7.35 to 7.45, and most preferably is about 7.4 (for human use). Dissolved carbon dioxide is also present in these solutions. When administered, these solutions not only tend to maintain the treated mammal's normal blood (and plasma) ratio of sodium to chloride, but also tend to set (regulate) the treated mammal's blood (plasma) pH at a normalized value. In addition the treated mammal's redox state and phosphorylation potential tend to be normalized.

Another (second) class (preferred) of such solutions characteristically utilizes (contains) chloride anions and a class of carboxylate anionic mixture couples comprised of at least one member from the group consisting of (a) a mixture of l-lactate⁻ anions and pyruvate⁻ anions, (b) a mixture of d-betahydroxybutyrate⁻ anions and acetoacetate⁻ anions, and (c) a mixture of both (a) and (b). These solutions have a physiological pH which is as above defined in connection with such (first) class of solutions. When administered, these solutions not only tend to maintain the treated mammal's redox state within a normal range, but also tend to maintain that mammal's phosphorylation potential within a normal range.

Another (third) class (more preferred) of such solutions characteristically utilizes (contains) both chloride anions, and bicarbonate/carbon dioxide mixture, as in such (first) class of solutions, but also utilizes (contains) such class of carboxylate anionic couples, as in such (second) class of solutions. When administered, these solutions achieve the above indicated effects obtained from the use of such (first) class of solutions and the above indicated effects obtained from the use of such (second) class of solutions.

The specified milliequivalent ratio of sodium to chloride in normal mammalian blood generally is believed to be in the range from about 1.24:1 to 1.47:1. In the case of a normal human adult, this range is now believed to extend (based on published information) from about 1.24:1 to 1.45:1 and preferably from about 1.33:1 to 1.42:1 and most preferably from about 1.36:1 to 1.42:1. These ratios of $Na^+:Cl^-$ are typically employed in solutions used in the practices of this invention. Ratios above 1.47, i.e. from about 1.47 to about 1.6 can be used within the spirit and scope of this invention as when it is the physician's conscience intention to create an abnormal $Na^+:Cl^-$ ratio as, for example, to create an excess of alkali reserve; however, such higher ratios are generally not presently preferred for general usage. In the case of dialysis fluids or to create an alkalotic condition in a cell or to correct an existent acidosis, this $Na^+:Cl^-$ ratio could range from a normal value (about 1.24 to 1.45) to about 1.6.

In using these couples, the important factor is the ratio of the concentration of [product]/[reactant] (see Eqns 0,1,2,3,4,5 & 7 hereinbelow). The absolute concentration becomes important in affecting the chemical activity of water (e.g. the osmotic pressure).

The total quantity, or sum (sigma), of each of the couples (bicarbonate/$CO_2$, l-lactate/pyruvate, and d-betahydroxybutyrate/acetoacetate) present in a solution of this invention can range from 0 to about 465 mMoles/liter of solution. However, in routine situations, the quantity of each couple commonly ranges from 0 to about 25 to 60 mMoles/liter.

Preferably, the ratio of bicarbonate milliequivalents per liter to dissolved carbon dioxide milliequivalents per liter in a solution of this invention can range from about 0.1:1 to 55:0.1 and preferably 11:1 to 24:1. More preferably, such total ranges from about 10 to 45 mM/l and such ratio ranges from about 18:1 to 26:1, and still more preferably such total ranges from about 23 to 35 mM/l while such ratio ranges from about 19:1 to 21:1. A ratio of 19.95 for $[HCO_3^-]/[CO_2]$ gives a pH 7.4, which is presently particularly preferred.

Preferably, the ratio of l-lactate anion milliequivalents per liter to pyruvate anion milliequivalents per liter in a solution of this invention can range from about 20:1 to 1:1. Preferably, such total quantity ranges from about 0.5 to 10 mM/l and such ratio ranges from about 3:1 to 15:1, and more preferably such total quantity ranges from about 2 to 8 mM/l while such ratio ranges from about 5:1 to 12:1.

Preferably, the ratio of d-betahydroxybutyrate anion milliequivalents per liter to acetoacetate milliequivalents per liter in a solution of this invention can range from about 6:1 to 0.5:1. Preferably, such total ranges from about 1 to 10 mM/l and such ratio ranges from about 4:1 to 1:1, and more preferably such total ranges from about 2 to 5 mM/l while such ratio ranges from about 3:1 to 1.5:1.

By the term "milliequivalent ratio" as sometimes used herein, reference is had the ratio of milliequivalents per liter of one substance to milliequivalents per liter of another substance in an aqueous medium.

One of the three near equilibrium couples employed in the practice of this invention (the bicarbonate⁻/carbon dioxide couple) tends, as used in this invention, to regulate the concentration of hydrogen ions in blood (plasma) and in the treated mammal's cells, and each one of such couples tends to normalize the redox state of each of the three pyridine nucleotide couples. The phosphorylation potential also tends to be normalized. Also, each such near equilibrium couple when used as herein described constitutes a safe entry point into the metabolic system of a mammal.

By the term "safe entry point" as used herein reference is generally had to a metabolite which, in living tissue or cells:
(1) does not cause a massive buildup of one or more of intermediate cellular metabolites,
(2) does not cause a severe disruption of any one of the controlling nucleotide ratios in a living cell,
(3) can be added to a physiological system of a living mammal at a concentration level which is greater than that which is found normally in such system (such as blood plasma of a fasting mammal) without causing any appreciable distortion in metabolism and without causing any pathological conditions to arise, and
(4) may be found in normal variants of the physiological state as when the total of d-betahydroxybutyrate plus acetoacetate reaches a level of about 8 to 10 mM/l in three-day fasting man, or the total of 1-lactate plus pyruvate rises to a level of about 5 to 6 mM/l in a jogging normal man.

Further, each such above described near equilibrium couple in this invention exhibits a distribution or permeability between intracellular fluid and extracellular fluid such that the ratio of the concentrations in, respectively, intracellular fluid to extracellular fluid ranges from about 1.0:1 to 1.5:1 in most all mammalian cells.

These respective three pairs of permeant monocarboxylate near equilibrium couples are unique among metabolites in being osmotically neutral in respect to the water in intracellular and extracellular space. Administration of these three couples, as their appropriate cationic salts (individually or in some combination with one another as taught herein) necessarily results in no net change in the distribution of water between intracellular and extracellular spaces in most tissues. By administration of varying ratios of these couples, however, the physician may control the distribution of water by varying the redox state and hence the phosphorylation state as described in equation 7 herein below. Osmotically active substances incorporated with the solutions of this invention preferably should each constitute a safe entry point. For example, glucose above 13 mM/l is higher than ever occurs under normal physiological conditions in a healthy man. Use of glucose above 13 mM/l (as in the widely used 5% glucose solution) as a calorie source is, apart from consideration of the source of pathology, and apart from the carboxylate couples, considered herein to be an acceptable source of calories. The extreme ability of the mammalian body to regulate its glucose metabolism makes it far to be preferred over other possibly nonionics, such as fructose or glycerol, which enter the metabolic system in an uncontrolled manner causing pathologic changes such as are already referenced, and so such are not safe entry points.

Characteristically, a solution used in the practice of this invention can contain from about 1 to 2400 millimoles per liter of sodium cations, but, in routine situations, commonly ranges from about 120 to 170 mM/L and more preferably from about 129 to 163.5 mM/l and most preferably from about 136 to 145 mM/l.

In addition, a solution contains sufficient chloride anions to produce a milliequivalent ratio of sodium cations to chloride anions in the range above defined.

Optionally, in addition to sodium, a solution of this invention can contain one or more of the following additional metallic cations each in a respective quantity as below indicated:

TABLE II

| cation component | Quantity range (millimoles per liter) | | |
|---|---|---|---|
| | broad | preferred | more preferred |
| potassium | 0–90 | 0–40 | 0–5 |
| calcium | 0–60 | 0–10 | 0–1.5 |
| magnesium | 0–15 | 0–10 | 0–1 |

Optionally a solution of this invention can have additionally incorporated (dissolved) therein from 0 to about 2400 millimoles per liter of at least one osmotically active substance which is preferably metabolizable and preferably substantially nonionic (including zwiterionic).

A solution used in the practice of this invention is further characterized by generally having:
(1) sufficient total substances dissolved therein to produce an osmolarity ranging from about 260 to 5000 milliosmoles/liter (mOs), and preferably from about 265 to 550 mOs, and more preferably from about 280 to 320 in mOs, and most preferably about 311 milliosmoles/liter.
(2) the relationship between total (dissolved) ionic substances is such that the pH ranges from about 5 to 9, and preferably from about 6.9 to 8.6; and most preferably from about 7.35 to 7.55;
(3) the charges of all cations equal the charges of all anions; and
(4) the minimum total concentration of all such near equilbrium couple(s) present is at least about 0.1 millimoles per liter, and preferably is at least about 0.5 mM/l, and more preferably about 2 mM/l, while the maximum concentration thereof is preferably not more than about 465 mM/L and more preferably is not more than about 65 mM/l and most preferably is not more than about 50 mM/l.

Examples of usable osmotically active substantially nonionic substances include glucose, glycerol, fructose, sorbitol, and the like. Glucose is presently most preferred.

As hereinbelow explained, the processes and the solutions of the present invention find use in a wide variety of therapeutic applications, such as in electrolyte and fluid replacement, parenteral nutrition, and dialysis.

Various additional objects, aims, purposes, features, advantages, applications, variations, and the like will be apparent to those skilled in the art from the teachings of the present specification taken with the claims.

DETAILED DESCRIPTION

This description is based upon best available information (including theory) known to the inventor. Any misdescription or the like, if such should exist, is not believed to alter the fundamentally correct basis and evidence supporting the present invention.

A. The Redox State

In biological cells, most reactions are catalyzed by enzymes of which an average cell may have of the order of $10^4$. In one classification, enzymes may be grouped in only six functional categories:
(1) dehydrogenases which transfer $H^+$ and $e^-$ from one substrate to another by the use of cofactors, such as $NAD^+$ (nicotinamide adenine dinucleotide), or prosthetic groups, such as FAD (flavin adenine dinucleotide), or others;

(2) kinases or phosphotransferases which effect the group transfer of a phosphate to a substrate usually by using a co-factor, such as ATP or other similar phosphate-containing compounds;

(3) carbon-carbon bond group transferases which either or break carbon-carbon bonds using co-factors of the co-enzyme A type or occur on a solid state substrate, such as a glycogen particle, or the surface of a fatty acid synthase multi-enzyme complex;

(4) isomerases which effect internal rearrangements within a compound;

(5) hydratases which either add or subtract water from a substrate; and (6) peptidases which break C-N bonds or create such bonds again usually taking advantage of a solid state synthetic matrix, such as a ribosome.

A special class of substrates taking part of biological reactions catalyzed by enzymes are called co-factors or co-enzymes. Co-enzymes, such as, for example, NAD, become attached and detached from an enzyme during a catalytic cycle, while prosthetic groups, such as flavin nucleotides or cytochromes, remain firmly attached during the catalytic cycle.

Since co-enzymes take part in multiple intracellular reaction within a given cellular compartment, the chemical potential of the co-enzyme couple becomes of central importance in energy transformation and oxido-reductions occurring in living matter. The thermodynamic characteristics of a particular whole set of oxido-reduction reactions is dependent upon the ratio of the free concentrations (strictly speaking, the activities) of the free [NAD+] and free [NADH]ratio. The ratio [NA(P)D+]/[NAD(P)H], thus represents and defines the redox state, at a given pH, of a particular pyridine nucleotide couple, and this ratio then determines:

(1) the extent and direction of reversible reactions in near-equilibrium with the co-enzyme couple;

(2) the extent to which a co-enzyme couple can be effective as an intracellular reducing agent, for example, in reducing the beta-oxoacyl co-enzyme A to beta-hydroxyacyl-coenzyme A; and (3) the magnitude of the free-energy changes of oxido-reductions in the electron transport chain responsible for the major portion of ATP synthesis.

The term "redox state" as thus used herein can be considered to refer to the oxidation-reduction state of any one or more of the three main pyridine nucleotide couples. Each of these couples are:

(A) The cytoplasmic [NAD+]/[NADH] linked dehydrogenase reactions of: (1) Lactate dehydrogenase (EC 1.1.1.27); (2) Maleate dehydrogenase (EC 1.1.1.37); and (3) Glycerol 3-phosphate Dehydrogenase (EC 1.1.1.8).

(B) The mitochondrial [NAD+]/[NADH] linked dehydrogenase reactions of: (1) Beta hydroxybutyrate dehydrogenase (EC 1.1.1.30); and (2) Glutamate dehydrogenase (EC 1.4.1.3).

(C) The cytoplasmic [NADP+]/[NADPH] linked dehydrogenase reactions of: (1) Isocitrate dehydrogenase (EC 1.1.1.42); (2) 6-Phosphogluconate dehydrogenase (EC 1.1.1.44); and (3) Malic Enzyme (EC 1.1.1.40).

The three pyridine nucleotide couples or pools each achieve different redox potentials because of the chemical energies of the substrates to which they are linked by their respective enzymes since the standard redox potential of [NAD+]/[NADH] is about −0.32 V. Thus, the near-equilibrium NAD-linked dehydrogenases have a Keq of about $10^{-11}$M, the mitochondrial NAD-linked dehydrogenases have a Keq of about $10^{-9}$M, and the cytoplasmic NADP linked dehydrogenases have a Keq of about 1. The differences in pyridine nuclestide redox states within the cell may be considered to result from the fundamental properties of matter. Over time, enzymes have evolved which take advantage of these fundamental properties to organize the chemical reactions of the cell into coherent purposeful sequences we know as metabolism.

The oxidation of lactate anions to pyruvate anions (that is, the loss of $2H^+$ and $2e^-$ from lactate) is accompanied by the reduction of pyridine nucleotide $NAD^+$. That is, $NAD^+$ gains two electrons and one $H+$ with the other $H+$ being liberated into the aqueous media where its activity is indicated and controlled by the $HCO^-_3/CO_2$ couple.

In general, the term "redox state" may also be defined as a ratio of [oxidized substrate]/reduced substrate]. The half or mid point potential Eh is conventionally measured as a potential in volts relative to a standard hydrogen electrode potential in accordance with the Nernst equation. The midpoint potential of the $NAD^+$ system, that is, where the ratio of [NAD+]/[NADH] equals 1 at a pH of 7.0 and a temperature of 25 C. is −0.32 volts under standard conditions. The midpoint potential of $[O^2]/[H_2O]$ is +0.816 volts. The cytoplasmic pyridine nucleotide system accepts $H+$ and $e^-$ from the organic compounds provided to mammalian organisms and transfers them to the mitochondrial pyridine nucleotide system where, by the electron transfer system, the $2H^+ + 2e^-$ $\xrightarrow{reduce}$ $1/2O_2$ to form water while conserving the energy of the oxidation reduction reaction by converting ADP+Pi to ATP. The reaction generates energy and heat. The redox state of cytoplasmic [NAD+]/[NADH] couple is about −0.19 volts, that of the mitochondrial [NAD+]/[NADH] couple is about −0.28 volts while that of the cytoplasmic [NADP+]/[NADPH] couple is about −0.42 volts. The last or $NADP^+$ couple is a much stronger reducing agent than the others and is used for reductive synthesis in the body, such as the making of fatty acids from carbohydrates; (see Krebs and Veech, 1969) in *The Energy Levels and Metabolic Control in Mitochondria* (Papa S., Tager J. R., Quagliariello E. & Slater E. C. eds) pp 329–382, Adriatica Editrice, Bari.

In the case of a living cell, a plurality of oxidation-reduction reactions occur simultaneously. Under normal conditions, these reactions occur in a normal healthy cell in a predictable manner. How these various redox states are regulated has just been described in thermodynamic terms. The normal healthy cell keeps the redox state of its free cytoplasmic [NAD+]/[NADH] redox couple at a ratio of about 500 to 1500 which corresponds to a voltage of about −0.2 volts. In this way, the cytoplasmic pyridine nucleotides can accept the $H+$ and $e^-$ from the substrates or food presented to the cell so that the cell may convert this food or substrate into energy. When the cell is metabolizing very reduced substrates, such as fatty acids, the cytoplasmic [NAD+]/[NADH] is about 400–800. When the cell is metabolizing carbohydrates or amino acids, it is obvious that these compounds are already partially oxidized. Therefore, the free cytoplasmic [NAD+]/[NADH] reflects the oxidation level of its substrate and becomes more oxidized in the range of about 800 to 1500.

The redox state of the free cytoplasmic [NAD+]/[NADH] couple can be determined by various techniques, such as by measuring the ratio of [lactate−]/[pyruvate−] (a) in freeze clamped tissue, (b) in the venous effluent leaving the organ in question, or (c) in the medium bathing the tissue in question. Alternatively [L-malate−]/[oxaloacetate−] or [-glyerophosphate]/[dihydroxyacetone P] ratios in tissue may be measured, if desired. The valve of cytoplasmic [NAD+]/[NADH] can then be calculated.

In healthy living mammals, the ratio of [L-lactate−]/[pyruvate−] is about 6, but can range, under special situations, such as starvation, to about 15–20. A [L-lactate−]/[pyruvate] ratio below about 20, as occurs after ethanol consumption, because of its links to the cytoplasmic [NAD+]/[NADH], is pathologic. A characteristic in all cells having a low [NAD+]/[NADH] ratio is believed to be demonstrable (observable) pathologic consequences, such as tissue swelling, low phosphorylation potential, low plasma membrane voltage, and abnormal electrolyte distribution between intracellular and extracellular $H_2O$.

Similarly, the redox state of the free mitochondrial [NAD+]/[NADH] can be determined by various techniques using tissues such as, for example, kidney or liver, by measuring the ratio of [D-beta-hydroxybutyrate−]/[acetoacetate−] (a) in freeze-clamped tissue, (b) in the venous effluent leaving such tissue, or (c) in the fluid bathing isolated such tissues. A determination of the free mitochondrial [NAD+]/[NADH] in other tissues, such as brain or heart muscle, is more complex, but, in some cases, can be accomplished by measurement in freeze clamped tissue of the [alpha-keto glutarate−] [NH4+]/[glutamate−] ratio (see Miller A. L., Hawkins R. A., and Veech R. L.; *J. Neurochem* 20, 1393–1400, 1973).

The normal ratio of mitochondrial [NAD+]/[NADH] is between about 5 and 20, and the normal ratio of [beta-hydroxybutyrate−]/[acetoacetate−] is about 1.3 to 4. The value of mitochondrial [NAD+]/[NADH] can then be calculated.

The redox state of the free cytoplasmic [NADP+]/[NADPH] couple is, of course, affected by the [$CO_2$] of surrounding fluids. Because of the lack of substrates which are permeable to the cell wall without significant and variable gradients, this redox state cannot at present be directly and totally regulated other than by the intracellular metabolic links with the cytoplasmic and mitochondrial [NAD+]/[NADH]. (See Krebs H. A. and Veech R. L.; "Pyridine Nucleotide Interrelations", 1969 in *The Energy Level and Metabolic Control in Mitochondrial* in Papa S., Tager J. M., Quagliariello E., and Slater E. C., eds. pp 329–383, Adriatica Editrice, Bari). Thus, for instance, because pyruvate reacts in both cytoplasmic [NAD+]/[NADH] and [NADP+]/[NADPH], administration of [$HCO_3^-$]/[$CO_2$] and [L-lactate−][pyruvate−] within certain narrow limits regulates these ratios because:

$$\frac{[NAD^+]_c}{[NADH]_c} = \frac{[NADP^+]_c}{[NADPH]_c} = \frac{K_{malic\ enzyme} \times [malate^{2-}]}{K_{LDH} \times [L\text{-lactate}^-][CO_2]}$$

Pyruvate, L-lactate and $CO_2$ are permeable to cell wall in a simple fashion, as are D-betahydroxybutyrate and acetoacetate, while $malate^{2-}$ and other dicarboxylates are not.

While the importance of redox state to the maintenance and normalization of intracellular metabolic processes and bioenergetics has long been recognized, there has never been previously, so far as is now known, any attempt to regulate or to normalize the redox state in such mammals (including especially human patients) receiving intravenous therapy, in patients undergoing dialysis, or in patients receiving parenteral nutrition. The present invention provides compositions and methods for regulating and/or normalizing the redox state in mammals (including man) treated herewith.

Existing electrolyte fluids make no attempt to maintain or normalize cellular redox potentials in any way whatsoever. In fact, most existing electrolyte fluids actually severely distort or make abnormal the redox balance of the cells, resulting in multiple and definable abnormalities. In this way, existing electrolyte fluids distort, such things as, for example, the rate of fat oxidation, the rate of glucose production, the rate of uric acid excretion, the rate of galactose metabolism in milk fed infants, and the like. All of these abnormalities lead to respectively, accumulation of fat in tissue, such as, for example, liver, production of either hyperglycemia or hypoglycemia, gouty crisis, cataracts, and neurological damage.

B. The Phosphorylation Potential

Just as the [NAD+]/[NADH] ratio is defined as a "redox state", by analogy, it is customary to define the energy state of the adenine nucleotide co-enzyme couple as the "phosphorylation potential". Because in living cells ATP, ADP, and $HPO_4$ exist in several charged forms, and in various complexation states with $Mg^{2+}$, it is customary to define these forms as sigma ATP, sigma ADP, and sigma Pi. The phosphorylation potential is thus defined by the relationship [sigma ATP]/[sigma ADP][sigma Pi].

It is clear that the reaction of oxidative phosphorylation contains both the redox state of mitochondria and the cytoplasmic phosphorylation potential. While the phosphorylation potential cannot apparently be controlled directly by addition of ATP and ADP to fluids contacting cells, since these compounds do not penetrate cell wall, there is, however, another reaction which is in near-equilibrium with the cytoplasmic [sigma ATP]/[sigma ADP][sigma Pi] (see Veech et al. in *J. Biol. Chem.* 254, 6538–6547, 1979). The reaction involves the two most active enzymes in the glycolytic sequence found in nearly all living cells and catalyzed by the enzymes glyceraldehyde 3-phosphate kinase (EC 2.7.2.3). Veech et al. (reference just cited) provide an equation which defines the relationship between the free cytoplasmic [NAD+]/[NADH] or redox state and the cytoplasmic phosphorylation state or [sigma ATP]/[sigma ADP] [sigma Pi]. This relationship is now and accepted by those familiar with this art and is (equation 5):

$$K_{G+G} = \frac{[\text{sigma 3-PG}][\text{sigma ATP}]}{[\text{sigma GAP}][\text{sigma ADP}][\text{sigma Pi}]}.$$

$$\frac{[NADH][H^+]}{[NAD^+]} = 1.83 \times 10^{-4}$$

or $$\frac{K_{G+G}}{K_{LDH}} = \frac{[\text{sigma 3-PG}]}{[\text{sigma DHAP}]/22} \cdot \frac{[\text{sigma ATP}]}{[\text{sigma ADP}][\text{sigma Pi}]}.$$

-continued $$\frac{[\text{l-lactate}]}{[\text{pyruvate}]} = 1.65 \times 10^{+7} M^{-1}$$

Metabolism in any living cell may be considered to be an ordered process whereby [H+] and electrons [e−] are removed from substrates and passed to co-enzyme acceptors which are largely cytoplasmic NAD+. This co-factor thus has a potential in the cell for more oxidation at about −0.19 volts than its standard potential of about −0.32 volts so that it may accept these electrons. The H+ and e− gathered in the cytoplasm, or even created in the mitochondria, may then be transferred to mitochondria by mechanisms involving other substrates to mitochondrial NADH which has a lower potential of about −0.28 volts in most mammalian cells. If e− and H+ are produced with a higher voltage, such as for example, from the oxidation of succinate or fatty acids, they form reduced FADH2 from FAD which has a more oxidized potential and therefore less potential energy. H+ and electrons produced from NADH-linked substrates produce 3 ATP for each ½ O2 consumed while those from flavo-protein (FAD) acceptors produce only 2. This difference in energy is due to the fundamental difference in the chemical reactions involved in producing the H+ and e−.

The fundamental process of cell respiration where NADH is oxidized to form heat and energy is called oxidative phosphorylation. It occurs in cellular organelles called mitochondria in a series of redox reactions called the electron transport chain. The mitochondrial electron transport system takes two electrons [2e−] from substrates and passes them up the chain to reduce ½ O2 forming H2O. The energy realized in this process is conserved in the cell in a chemical form of anhydride bond in the terminal phosphate group of adenosine triphosphate (ATP). The formation of three pyrophosphate bonds of ATP leads to the formation of H2O and requires 3H+ in addition to the formation of the 1H2O formed from NADH plus H+ plus 2 e− taken from the substrates being oxidized by the cell. The reaction of oxidative phosphorylation is a spontaneous one (see Veech et al in cited reference).

The phosphorylation potential of living cells can be measured by determining the cellular contents of the components of certain metabolites (see Veech R. L., in *J. Biol. Chem.* 254, 6538–6547, 1979). In certain tissues, such as brain, heart, or skeletal muscle, measurement of the components of the creatine kinase reaction (EC 2.7.3.2) may be used as the preceding reference describes.

Since on theoretical grounds Veech et al. in *J. Biol. Chem.* 254, 6538–6547, 1979 showed that [creatine]/[creatine-P] is in near equilibrium with the cytoplasmic [sigma ATP]/[sigma ADP], it follows that the phosphorylation potential in skeletal muscle or brain may be evaluated in living human patients by measuring the [sigma CrP]/[Sigma Pi] ratio without resorting to freeze-clamping of organs by the use of $^{31}P$ NMR (nuclear-magnetic residence) as has been done by Chance and others (see Chance B., et al., *Proc. Nat'l. Acad. Sci,* U.S. 78, 6714–6718, 1981). The agreement between the necessarily destructive methods heretofore used in animals by Veech, and the somewhat less precise but non-harmful methods of sigma creatine-P/sigma Pi measurements with $^{31}P$ NMR, demonstrate that the normal value of the phosphorylation potential or [sigma ATP]/[sigma ADP][sigma Pi] as estimated by Veech is essentially correct (as stated above). Further, the increasing availability of $^{31}P$ NMR facilities in academic medical centers ensures that measurements in living human patients can be conducted without harming them.

Because the cytoplasmic [sigma ATP]/[sigma ADP][sigma Pi] or phosphorylation potential is related to the cytoplasmic [NAD+]/[NADH] or redox state by a near-equilibrium reaction catalyzed by glyceraldehyde-3-phosphate dehydrogenase and 3-phosphorglycerate kinase, it is possible to alter and regulate and normalize the phosphorylation potential of a living cell by affecting its redox state (as is believed to be accomplished in the present invention).

If a simple, reliable chemical means are known and/or could be devised to change the intracellular redox state, it would of necessity have to change the other components of the reaction which include the phosphorylation potential and would be of obvious fundamental importance in medicine and in many other related fields of biochemistry, physiology, molecular biology, tissue culture, veterinary medicine, and like endeavors. Such a chemical means is provided by the teachings of the present invention.

C. Redox Active Metabolites

As above indicated, a large portion of metabolism is devoted to energy generation which involves the removal of H+ and e− from substrates in cytoplasm or mitochondria for delivery to mitochondrial electron transport scheme for conversion of 2H+ plus 2e− with ½O2 to yield H2O with the liberation of about 1 volt or 54 Kcal/mole of energy which is conserved in the [sigma ATP]/[sigma ADP][sigma Pi] couple. In mammalian cells, the [sigma ATP]/[sigma ADP][sigma Pi] has a delta G (free energy in kilocalories per mole) of between −13.6 and −14.1 Kcal/mole, the transfer to this H+ and e− is accomplished by a series of cofactors, the major one being NAD (nicotinamide adenine dinucleotide) and its phosphate (called NADP). Oxidation is defined as the removal of electrons, and reduction as the addition of electrons. The removal or addition of e− plus H+ from substrates is catalyzed by enzymes, the major group of which are called dehydrogenases, as indicated above. The enzymes (catalysts) control the rates at which reactions occur, but the extent and the direction of a reaction, and the amount of energy (delta G) which may be liberated by a reaction, is determined by the inherent energy in the chemical bonds (delta G°) and the concentrations of the reactants and products.

Determination of any redox or energy state must always involve a ratio of chemical compounds, [oxidized product]/[reduced reactant] and [oxidized co-factor]/[reduced co-factor]. The overall reaction is thus comprised of two individual redox systems, one of which is oxidized, while the other is reduced.

Those enzymes within a cell which are of sufficiently high activity relative to the flux through the enzyme to catalyze a state of near equilibrium are suitable for controlling the redox state. A reaction may be experimentally determined to be in a state of near-equilibrium by measuring the equilibrium constant (Keq) under conditions which approximate those existing within a cell, that is, where the ionic strength I equals 0.25, the pH equals 7 to 7.2, the temperature equals 38° C., and the free [Mg$^{2+}$] equals 0.5 to 1 mM, and also where I equals ½ sigma molarity of ions times the valence of ions. With knowledge of the value of Keq, the concentration of the reactants in a tissue may be measured in rapidly frozen tissue. If the value of [product]/[reactant] measured, in several different dehydrogenase reactions, gives the same calculated free [NAD(P)+]/[NAD(P)H] ratio, then the reaction is said to be in "near-equilibrium" under in vivo conditions. In the case of near-equilibrium dehydrogenase reactions, addition of a predetermined amount of a ratio of product/reactant allows one to set the [NAD+]/[NADH] ratio within the cell at a predetermined level, provided the reactants penetrate the cell wall freely or in a constant ratio one to another. The redox state or [NAD(P)]+/[NAD(P)H] ratio may be set inside a cell by controlling the [$CO_2$] and the redox state of the cytoplasmic free [NAD+]/[NADH] as described previously. Each of the three couples employed in this invention is a near equilibrium couple.

Various cytoplasmic and mitochondrial NAD-linked dehydrogenases appear to be capable of controlling or setting the [NAD+]/[NADH] ratio in each of cytoplasm and mitochondria. Because of the special permeability of the complete couple of L-lactate$^-$/pyruvate$^-$ for cytoplasm and D-B-hydroxybutyrate$^-$/acetoacetate for mitochondria, these two redox couples are preeminently well suited for the practice of this invention. This is so because: (1) both monovalent anions in the pair distribute themselves equally between plasma and cellular $H_2O$; (2) changes in distribution of anions between extracellular and intracellular $H_2O$ during pathological states will effect both members of the couple equally through preserving the integrity of the given redox state; (3) both couples react with "dead end" branches off the main metabolic sequences; (4) the concentration of these normal transport metabolites can reach very high levels in plasma of normal healthy mammals under physiological conditions; and (5) the members of both couples each contain a charge which can be used to normalize the low Na+:Cl$^-$ milliequivalent ratio characteristic of most I.V. (intravenous) solutions.

The near equilibrium redox active metabolite carboxylate couples employed in the practice of the present invention, specifically, l-lactate$^-$/pyruvate$^-$ and d-betahydroxybutyrate$^-$/acetoacetate$^-$, constitute safe entry points and appear to be unusual in their ability to not only normalize the redox state in cytoplasm through the reaction of l-lactate and pyruvate with LDH, but also to regulate the redox state in the mitochondria through reaction of and d-betahydroxybutyrate and acetoacetate with the enzyme d-betahydroxybutyrate dehydrogenase (EC 1.1.1.30) which is apparently present in most tissues at a high enough activity to maintain near-equilibrium conditions at most times.

As indicated above (see Table 1 and related text), previous attempts to normalize the sodium to chloride milliequivalent mole ratio of about 1.36 were usually done by adding either (d,l) lactate$^-$ or acetate$^-$, or a combination of lactate and acetate, or other inappropriately paired carboxylate anions, leading inevitably in all known instances to severe and measurable pathological consequences.

In the solutions of the present invention, one employs at least one of the above indicated three different near-equilibrium couple mixtures. In each couple mixture, the two member components are employed in a definite milliequivalent ratio relative to one another. Such a ratio is needed in order to control either the plasma pH, or the redox state (and consequently the phosphorylation potential), or both.

Among the possible mixture couples which could be used, these three couples were selected because, for each couple:

1. The distribution of ions between extracellular fluid and intracellular fluid is predictable in all normal and pathological states.
2. It is capable of achieving and regulating a predetermined redox state and phosphorylation potential within most living cells.
3. At least one member thereof contains an anionic charge.
4. It can be given in aqueous solution form so that the total levels administered do not substantially exceed total levels found under normal physiologic conditions in mammalian blood (plasma).
5. Both members thereof constitute safe entry points which enter the metabolic sequence and pathways at a safe entry point and these safe entry points, are at dead end terminals in the metabolic pathways, thus avoiding any possibility of a pathologic buildup of metabolites with the consequence that a disordering of cellular metabolism would consequently result.
6. It need not induce a change in water distribution between intracellular and extracellular space.
7. It may be osmotically neutral in most tissues.
8. Administration permits control of water distribution as a result of changing redox and hence the linked phosphorylation state and the magnitude of the extracellular Na+ Donnan forces generated thereby.

When blood levels of, respectively, l-lactate/pyruvate, d-betahydroxybutyrate/acetoacetate, and bicarbonate/$CO_2$ are maintained within their normal limits, then the redox state, the phosphorylation state, and the plasma pH each tend to be normalized which is achieved as a result of administration of a solution of this invention.

Intracellular concentration of each member of each coupled is achieved through the extracellular fluid because each of the monovalent anions chosen, namely, l-lactate and pyruvate, d-betahydroxybutyrate, and acetoacetate, and also bicarbonate, distribute themselves between plasma water, extracellular water, and intracellular water in concentration ratios or gradients which are the inverse of the hydrogen ion (concentration), thereby achieving a gradient or ratio of about 1.35 between extracellular and intracellular fluid. The non-ionic dissolved $CO_2$ distributes itself substantially equally between extracellular fluid and intracellular fluid.

Those learned in the art realize a redox state must be defined at a certain pH, or [H+] ion concentration. The near-equilibrium couple [$HCO_3^-$]/[$CO_2$] defines the cellular pH or [H+] concentration. This near-equilibrium couple is therefore an integral part of the redox state. Preferably the level of sigma [$HCO_3^-$] plus [$CO_2$] present in any given solution of this invention may vary under normal physiological conditions from about 10 mM/l to 40 mM/l, but in general, is (when present) in the range from about 25 to 35 mM/l. The milliequivalent ratio of [$HCO_3$]/[$CO_2$], of course, in effect, is defined so as to give a [H+] ion concentration, or pH, in the physiological range as defined above.

The redox and phosphorylation states in various tissues in the rat have been given by Veech et al. *J. Biol.*

Chem. 254, 6538–6547, 1979 and for the redox states in Veech, Eggleston and Krebs, *Biochem. J.*, 115, 609–619, 1969. The same general principles are believed to hold for man, but cannot be directly proved since freeze clamping is not possible. NMR measured estimates of the phosphorylation potential in brain and muscle in living humans, however, agree well with these figures derived by freeze clamping procedures.

By the term "plasma" or "blood plasma" as used herein, conventional general reference is had to the liquid part of the blood as distinguished from the corpuscles. Plasma can be prepared by various techniques well known to those familiar with this art typically using centrifugal force to separate a supernatant (which is plasma) after non-coagulated blood is centrifuged.

By the term "extracellular fluid" as used herein conventional general reference is had to all body fluids in extracellular spaces outside of the circulatory system (e.g. the blood) and outside of intracellular fluid in a mammal (typically constituting about 15% of the weight of a mammal).

By the term "intracellular fluid" as used herein conventional general reference is had the fluid within cells which constitutes about 57% of total mammalian body weight.

It is well known that (see Black DAK. *Lancet i*, 305–12 1953) infusions into a mammal of large amounts sodium and chloride in a solution milliequivalent ratio of 1 to 1 lead inherently to hyperchloremic acidoses. This knowledge lead to the development of such well known solutions as lactated Ringers, and also to the compositions used in most dialysis solutions, wherein, in a majority of cases, the sodium to chloride milliequivalent ratio is normalized compared to plasma values by the addition of various organic anions (as described above). These organic anions chosen in the prior art are as described above. In no known prior art case, however, were any solutions with a normalized Na:Cl milliequivalent ratio produced which did not use organic ions in such a way as to inherently lead to severe and measurable metabolic abnormalities and pathologic consequences. Mixtures of redox pairs nor $HCO_3^-$ /$CO_2$ were not generally used to normalize the $Na^+$:$Cl^-$ ratio nor were the reasons known why a choice of near equilibrium matched couples was desirable. Correction of this ratio between sodium cation and chloride anion by the mixture couples as taught by the present invention eliminates the pathologic consequences of all the prior art electrolyte solution compositions. In addition, the solution compositions of this invention tend to normalize plasma inorganic electrolyte composition and to correct the anion gap which in many instances could not be accomplished by prior art electrolyte solutions.

Thus, in summary, the compositions of this invention tend to normalize (a) plasma pH, (b) composition of major plasma inorganic electrolytes, (including the milliequivalent ratio of $Na^+$:$Cl^-$ and the anion gap), (c) the redox state, and (d) the phosphorylation potential. These normalizations are obtained and achieved without the abnormal, pathological consequences inherent in all known prior art solutions. No other man-made solutions are presently known which will accomplish this combination of results.

D. Other Possible Benefits (Theorized)

It is theorized, and there is no intent to be bound by theory herein, that the solutions of the present invention, in addition to the properties above described, further tend to normalize at least one of the following states:

1. Distribution of water between intracellular and extracellular compartments,
2. Distribution of major inorganic electrolytes between intracellular and extracellular fluid,
3. Transmembrane cellular potential, and
4. The degree of organization within the living cell or its entropy.

The ratio of the chemical activity of free water on each side of a typical normal mammalian cell membrane is always unity. Movement of water across such a cell membrane is achieved by the movement of osmotically active substances. Changing the cellular phosphorylation potential, through the NaK ATPase, therefore, inherently effects a change in the steady state level of ions inside and ions outside of a cell with the net result being a change in the level of osmotically active substances on either side of the cell membrane.

The transmembrane cellular potential is herein viewed as a Donnan potential (see Donnan F. G., *Chem. Rev.* 1, 73–90, 1924) resulting from the total amount of the non-diffusible osmotically active substances on either side of the cell membrane, and so is not a function of the so-called electrogenic sodium potassium ATPase, as is commonly held. (See *The Cell* (1983), Alberts B., Bray D., Lewis J., Raff M., Roberts K. and Watson J. D., pp 294, Garland, N.Y.). Rather the Na/K ATPase is viewed as an electroneutral "osmopump" exporting a net of 2 milliosmoles (1 $Na^+$ and 1 $Cl^-$) from intracellular to extracellular space for each ATP by hydrolyzed. The distribution of [$Na^+$], [$K^+$], [$Cl^-$] and [$Ca^{2+}$] in most extracellular and intracellular fluid is thus viewed as a function of the phosphorylation potential and the state of internal cellular order or entropy. The NaK ATPase is thus viewed as the near-equilibrium link between intra and extracellular electrolytes in the manner given in equation 7. The magnitude of the extracellular fluid $Na^+$ Donnan is therefore a function of the cellular phosphorylation state. (See Leaf A. *Biochem J.* 62: 241–248, 1956)

Cellular water volume can be measured by known (e.g. conventional) techniques involving the distribution of inulin and tritiated water.

Distribution of major inorganic electrolytes between intracellular and extracellular fluid can be measured by known (e.g. conventional) techniques, such as flame photometry, atomic absorption spectroscopy, van Slyke gas analysis, and the like.

Transmembrane cellular potential can be measured by known (e.g. conventional) techniques; such as with electrodes or probes, and the like. Calculation of such cellular voltage can be achieved from a measurement of the distribution of chloride ions between intracellular and extracellular fluid following Nernst's law.

A quantitative relationship is theorized to exist involving redox state, phosphorylation potential and the above referenced three states. This relationship may be expressed by the following equation:

$$\Delta G = 0 = \Delta G°_{ATPase} + \Delta G° \frac{[Na^+]\ldots}{[Na^+]\ldots} + \quad (7.)$$

$$RT \ln \frac{[\Sigma ADP][\Sigma Pi]}{[\Sigma ATP]} +$$

-continued $$RT \ln \frac{[Na^+]_o^3 [K^+]_i^2 [Cl^-]_o}{[Na^+]_i^3 [K^+]_o^2 [Cl^-]_i} + T\Delta S$$

wherein

The values of the various terms in the foregoing equation of are given as follows (for muscle and brain):

$$\Delta G = 0 = -7.73 \text{ kcal/mol} + 0 + (-6.3 \text{ kcal/mol}) + 8.4 \text{ kcal/mol} + 5.6 \text{ kcal/mol} \quad (7.1)$$

In the foregoing equation, the phosphorylation potential is shown to be in a state of near equilibrium with the substrates of the sodium potassium ATPase. Since the chloride ion is cell wall permeable, this ion distributes itself in conformity with the transmembrane cellular potential. Movement of three sodium ions out of the cell and two potassium ions into the cell across the cell membrane necessarily results, from the law of electrical neutrality, in the movement of one chloride ion from inside the cell to outside the cell across the cell membrane. This makes the sodium potassium ATPase, in effect, an osmopump resulting in the export of two milliosmoles per ATP hydrolyzed. This pump is electro-neutral.

The T delta S term, which is approximately 5.6 kilocalories per mole of ATP hydrolyzed, is an entropy term. It, therefore, refers the state of randomness within the cell. The positive nature of this entropy term indicates that a high degree of order is imposed on the intracellular environment. In terms of quantum and statistical mechanics, the number of ways of achieving a certain energy state is called its degeneracy ($\Omega$). The Boltzmann equation defines S (or entropy) as $S = K_B \ln \Omega$, where Boltzmann's constant (which relates the gas constant to Avogadro's number), or $K_B = 1.38 \times 10^{-23}$ J/°K.

It follows from the foregoing equation 7, above, that the distribution of calcium inside the cell is a function of the cube of the respective sodium concentrations inside and outside of the cell because of the action of the high-activity sodium-calcium exchange enzyme. The following equation shows the relationship:

$$K_{Na/Ca} = \frac{[Na^+]_i^3 [Ca^{2+}]_o [Cl^-]_i}{[Na^+]_o^3 [Ca2+]_i [Cl^-]_o}$$

where:

[ ]$_i$~intracellular concentration in cytoplasmic H$_2$O
[ ]$_o$~concentration in extracellular H$_2$O.

Unlike the simple NaK ATPase which moves 2 mOsmoles out of the cell thus moving H$_2$O with it, the result of moving Ca$^{2+}$ out of the cell by the Na-Ca exchanger is to move a net of 3 mOsmoles into the cell, thus increasing the cells water content. The NaK ATPase must then operate again to move the excess sodium out in exchange for K$^+$ to restore osmotic equilibrium between extracellular space H$_2$O and cell H$_2$O.

The net result of the foregoing equation (7) is that the water of both intracellular and extracellular fluid is a function of the sodium/potassium ATPase (EC 3.6.1.3) and also of the phosphorylation potential.

It can be empirically seen that the voltage across a cell membrane is inversely related to the chloride distribution and the phosphorylation potential.

Correlation between phosphorylation potential, intracellular chloride and transmembrane cellular potential for various mammalian tissues is illustrated in Table II below:

TABLE IIa

Correlation between Phosphorylation Potential, Intracellular Chloride and Transmembrane Cellular Potential.

|  | $\frac{[\Sigma \text{ ATP}]}{[\Sigma \text{ ADP}][\Sigma \text{ Pi}]}$ | $[Cl^-]_i$ mEq/l | $\Delta E$ mV |
|---|---|---|---|
| red cell | 7,000 | 90 | −9 |
| liver | 15,000 | 40 | −40 |
| brain or muscle | 30,000 | 7-9 | −70 |

From Table II, it is seen that low phosphorylation potential correlates with a high intracellular chloride, and a low transmembrane cellular potential correlates with the inherent setting of the potential as a function of the Donnan-active material within the cell with the phosphorylation potential merely overcoming the Donnan forces so as to export two milliosmoles, as described in equation 7.

Because of the voltage dependent permeant nature of chloride ion to most non-epithelial tissues (Ho MK, Guidotti G. *J Biol Chem* 250: 675–683, 1975) the induction of high extra cellular chloride, such as occurs, for example, in current intravenous electrolyte therapy, must have profound pathological consequences for the metabolism of the cell, even though the purpose of such intravenous and dialysis therapy is to normalize the water and electrolyte concentrations of the various mammalian body cellular compartments. This is so because the ratio $$\frac{[Na^+]_o^3 [K^+]_i^2 [Cl^-]_o}{[Na^+]_i^3 [K^+]_o^2 [Cl^-]_i}$$

and the T$\Delta$S term link the cellular phosphorylation and the cellular redox states to intracellular and extracellular water and the electrolyte concentrations of Na$^+$, K$^+$, Cl$^-$ and also Ca$^{2+}$.

E. Electrolyte Solution Preparation

The electrolyte solutions of the present invention can be prepared by any convenient or conventional procedure.

As a matter of accuracy, the compositions of this invention can be described in terms of their ion contents which can be expressed either in terms of millimoles per liter of solution, or milliequivalents per liter of solution. It is standard practice in this art in describing a given solution to separate anions from cations, and nonionics from ionic materials; this practice is followed herein in the main. As those skilled in the art will readily appreciate, a translation or conversion of millimoles per liter of solution, or of milliequivalents per liter of solution, into grams of a given salt added per liter of water is routine and is given in any standard text book in the field, such as, for example, "Data For Biochemical Research" (1969) (Dawson R. M. C., Elliott W. H., Jones K. M., Eds.) Clarendon Press, Oxford at pages 507 and 508. This reference illustrates not only the salt starting materials, but also the order of addition of same in the preparation of certain illustrative prior art electrolyte solutions shown therein. Solutions of this invention are readily prepared by this type of procedure. The particular salt combination used for a given solution may change from time to time in a manufacturing operation as those skilled in the art well know. The significant factor is that the final concentrations of respective component ions in any given solution remain as specified or desired. In view of the developed state of this art, no detailed description of electrolyte solution preparation procedure is believed to be necessary or desirable herein.

The solutions of this invention, and the component materials incorporated thereinto, are, in general, formulated, so as to contain a combination of a the desired physiological $Na^+$:$Cl^-$ milliequivalent ratio normality, one or more of these three near-equilibrium couple(s), and other components.

Thus, various initially existing pathological conditions can be ameliorated by practice of the processes and the compositions of the present invention, depending upon the particular solution used and the particular use conditions and circumstances in any given use situation. Thus, by this practice of this invention, one can accomplish in a physiologically acceptable manner the removable of metabolic products from cellular water, the replacement of body fluids and electrolytes, and the administration of nutrients, and the like, as desired. The solutions may be administered in any fashion desired so long as they contact living mammalian tissue. Administration can be accomplished by any convenient technique, such as for examples, intravenously, intraarterially, intradermally, intrathecally, orally (especially when the solution contains the non-bicarbonate containing couples), across a semi-permeable membrane, or the like, as those skilled in the art will readily appreciate. The solutions of this invention as prepared are, in general, well suited for the administration of therapeutic agents to living mammals.

When bicarbonate anions are not present, then the level of combined (or sigma) l-lactate/pyruvate and/or d-betahydroxybutyrate/acetoacetate present in a solution of this invention is optionally greater than when bicarbonate is present in order to achieve the desired milliequivalent ratio of sodium to chloride, as indicated. The concentration of either sigma l-lactate/pyruvate and/or of d-betahydroxybutyrate/acetoacetate in a given solution of this invention can thus range up to the full maximum quantity desired (within the limits described herein). It is presently preferred, particularly when no bicarbonate is present, to employ a mixture of l-lactate/pyruvate with a mixture of d-betahydroxybutyrate/acetoacetate.

Those skilled in the art will realize that in any given solution of this invention one can incorporate an excess of one or more individual members of any one mixture couple of this invention so that (a) the ratio of one member to the other of any given couple and (b) the total quantity of both mixtures or members lies outside of the ranges hereinabove described without departing from the spirit or scope of the invention. Such a single member excess is not recommended when practicing the present invention. However, if such a single member excess does occur, the amount of the excess can be calculated by determining the maximum ratio of one couple member to the other which can be present in accord with the above teachings, and then the quantity of one couple member remaining (or present) which is outside of this ratio range may be considered to constitute an excess. The effect of such an excess is evidently merely to cut down, but not to eliminate, the efficacy of what effect would otherwise be obtained by using only a solution which contains mole ratios and quantities of respective mixture couples within the spirit and scope teachings of this invention.

In the making of solutions of this invention, it is preferred to employ the optically active l-lactate salts or l-lactic acid (which will make the desired l-lactate anions in solution), and also similarly to employ d-betahydroxybutyric acid or d-betahydroxybutyrate salts (which will make the desired d-betahydroxybutyrate anions in solution. Choice of particular salt or acid (or mixture) used in any given case depends among various factors, such as upon the other starting inorganic salts which a formulator desires to use (based upon availability, cost, and like factors), all as will be readily appreciated by those skilled in the art. Racemic (d-l) mixtures could be used, but their use is preferably avoided since these unnatural isomers are known to be associated with specific toxic effects. Racemates can be metabolized. If such are used, the ratios of one member to another in the respective near equilibrium couples involved should be based upon the quantity of particular optically active form present (e.g. either [l-lactate$^-$] or [d-betahydroxybutyrate$^-$], as the case may be.

In the solutions of this invention at the pH ranges described, not all couple member material of any given couple will be in an ionized (anionic or dissociated) form; a portion of this material will be in an un-ionized (undissociated) form. Typically, the quantity of undissociated material (such as l-lactate acid, pyruvic acid, d-betahydroxybutyric acid, acetoacetic, sodium bicarbonate, carbonic acid, or the like) is not more than about 0.1% of the total quantity of all material of any given species (e.g. l-lactate, pyruvate, d-betahydroxybutyrate, acetoacetate, or bicarbonate). For purposes of calculating a milliequivalent ratio, molar concentration, or the like, it is preferred to base computations upon the total material of any given species which is present in a solution of this invention.

The carbon dioxide, when used, can be introduced either as a gas, preferably using conventional aeration apparatus to effect a solubilization of $CO_2$ in a solution, or it can be generated in situ from a dissolved metal (such as sodium preferred), potassium, calcium or magnesium) salt of bicarbonate in combination with a dissolved acid (lactic, pyruvic, betahydroxybutyric, or acetoacetic) in respective proportions of each such that the total quantity of dissolved carbon dioxide so generated is within the ranges described herein for use in a solution of this invention.

As elsewhere indicated herein, if desired, a solution of this invention can also contain various known additives in concentrations taught by this art, but it is presently preferred not to employ anions and nonionics which will not be safe entry points.

In general, a solution of this invention should contain as a minimum of total of sigma (lactate/pyruvate and/or sigma betahydroxybutyrate/acetoacetate) and/or sigma bicarbonate/carbon dioxide which is at least about 0.5 millimoles per liter as indicated. Below these levels, benefits in normalization of body metabolism as explained above are apparently achievable, but such benefits become increasingly difficult to demonstrate and prove by state of the art techniques of measurement. Consequently, it is preferred to avoid, if possible, homeopathic possibilities by using minimum concentrations as above indicated.

When bicarbonate is present, the total quantity of sigma (lactate/pyruvate and/or betahydroxybutyrate/acetoacetate) used can generally be reduced which is now believed to be desirable. Thus, when bicarbonate is present, the total sigma (l-lactate/pyruvate and/or d-betahydroxybutyrate/acetoacetate) is preferably about 2 to 17 millimoles per liter.

When a solution of this invention contains at least one osmotically active substance (preferably metabolizable and nonionic), it is added to provide nutritional or osmotic requirements. Since it is uncharged, it does not therefore contribute to normalizing the $Na^+:Cl^-$ ratio or to correcting the anion gap.

F. Classification and Usage of Electrolyte Solutions

All of the formulations of this invention from a composition viewpoint fall into what can be regarded generally as being either one of two distinct classes:

Class I which comprises fluids containing at least one and not more than two metallic cations selected from the group consisting of sodium, potassium, calcium and magnesium, while Class II which comprises solutions containing at least three and typically not more than four metallic cations selected from the same group.

Class I fluids are typically administered at dose levels which are not greater than about 1 liter per human adult patient per 24 hour day, one typical dose level being 500 ml per such patient per 24 hour day.

Class II fluids are typically administered at dose levels chosen by the physician, and these levels can range from 0 to greater than 100 liters per human adult patient per 24 hour day, depending upon circumstances.

Each of the inorganic electrolytes present in a solution of this invention is typically present in an amount of at least about 0.5 mM/l thus clearly qualifying them as "electrolytes" as such rather than as trace metals, such as is associated with levels of iron, manganese, zinc and the like in normal plasma and which trace metals can be present in normal plasma at levels less than about 0.4 mM/l. If desired, of course, trace materials can be added to solutions of this invention.

Each of the cations sodium, potassium, calcium, and magnesium and each of the anions bicarbonate, chloride, and phosphate are normally found in the plasma and tissue of mammals at concentration levels greater than or equal to about 1 millimolar per liter of body fluid (see Table I). The solutions of this invention, in general, contain respective inorganic electrolyte concentrations which resemble the corresponding concentrations of such electrolytes in plasma (when any one of such electrolytes is present in any given solution of this invention).

Class I solutions are useful as intravenous solutions for electrolyte and fluid therapy especially where no more than about 10% of total blood volume (about 500 ml in an adult human) is to be administered over a 24 hour day. Solutions of this type have been used in the treatment of hemorrhagic shock where 2400 mOsmolar NaCl solutions have been advocated. (See Velosco IT, Pontieri V, Rocha M, Silva E, Lopes OU. *Am J Physiol* 239: H664-673, 1980).

Class II solutions find use in intravenous applications where over 10% of total blood volume (about 500 ml in an adult human) is needed to be given to a human adult over a 24 hour day. Administration can be made, for example, to a normal human with an impairment or injury, such as loss of limb or the like, or to a human with impaired rental excretion: Class II solutions can be used as a improvement for lactated Ringer's solution.

Class II solutions also are useful in dialysis, peritoneal, ambulatory peritoneal dialysis or hemodialysis, where perhaps 120-160 liters per hemodialysis day per patient are used. Such solutions can be used improve existing acetate or lactate containing solutions, but use of acetate is not desired in the practice of this invention.

Given the solutions of this invention, a physician may henceforth wish to administer normal or hypertonic saline solution only to correct a condition of metabolic alkalosis since giving $Na^+:Cl^-$ in a 1:1 milliequivalent ratio causes acidosis and other disturbances recognized herein. The solutions described herein improve normal saline solution.

Solutions of Class II can be used as such, or can be employed as diluent for plasma extenders or for reconstituted frozen blood. For example, dehydrated plasma can be dissolved and dispersed in a solution of Class II so as to produce an injectable solution, as those familiar with the art will appreciate.

Each one of these Class I and II solutions can be considered to be characteristically comprised of four subgroups which can be stated briefly as follows:

A. Solutions containing only inorganic ions and one or more of our near-equilibrium couples of organic anions pairs with which chloride anions are included.

B. Solutions containing in addition to such inorganic ions and organic ion pairs a mixture of bicarbonate and carbon dioxide.

C. Solutions containing such inorganic ions and organic ion pairs plus non ionic materials.

D. Solutions containing in addition to the inorganic ionic material both mixtures of bicarbonate and carbon dioxide (as characterized in B above) plus other nonionics (of the type characterized in C above).

As indicated above, avoidance of substances in solutions of this invention which do not constitute safe entry points is preferred. For example, use of such nonionic osmotically active substances as fructose and glycerol are preferably avoided and are not recommended for use in the practice of this invention. Also, avoidance of the organic anions used in the prior art which are not safe entry points is recommended, including use of lactate alone, acetate alone, lactate and acetate together, gluconate, citrate, and the like.

Prior art in dialysis fluids shows that the composition of the fluids now commercially used evidently is intended to approximate that of plasma with the proviso that the anion gap is typically corrected with abnormal amounts of typically acetate or lactate. The suggestion has also been made in the prior art dialysis fluid composition should approximate the composition of interstitial (extracellular) fluid. While such compositional approximations now appear to be essentially incorrect especially from the standpoint of achieving dialysis fluids of maximal safety and utility and patient benefit, it is submitted that such approximations can be substantially benefited by compounding dialysis solutions in accord with the teachings of the present invention (both for hemo- and peritoneal dialysis).

Solution compositions of the present invention of Class I and Class II are generically characterized herein above. The following Table III summarizes preferred solutions of this invention in terms of composition at the time of administration (e.g., water having dissolved therein each of the indicated components in the respective amounts indicated).

With regard to the term "nonionics" in a solution or process of this invention, those skilled in the art will appreciate that this term connotes no net charge on the molecule involved at the particular solution pH specified.

Solutions of this invention can be prepared as concentrates which at 0.8 molar solutes or greater will inhibit bacterial growth, as those skilled in the art will appreciate, and such concentrates can then be diluted with water before administration to prepare compositions of this invention.

In general, solutions of this invention are believed to be preparable so as to be storage stable for periods of time at least sufficient to permit packaging, intermediate storage in sealed containers, followed by administration.

TABLE III

Generic Compositions of Class I and Class II Solutions

| Component | Composition of time of Administration Quantity Range (millimoles per liter) | |
|---|---|---|
| | broad | preferred |
| Total cations (mEq/L) | 1 to about 2400 | 130 to 170 |
| (1) sodium$^+$ | 1 to about 2400 | 130 to 165 |
| (2) potassium$^+$ | 0 to about 90 | 0 to 5 |
| (3) calcium$^{++}$ | 0 to about 60 | 0 to 1.5 |
| (4) magnesium$^{++}$ | 0 to about 15 | 0 to 1 |
| Total anions (mEq/L) | about 1 to 2400 | 130 to 170 |
| (5) chloride$^-$ | 0.6 to about 1940 | 80 to 130 |
| (6) bicarbonate$^-$ | 0 to about 465 | 0 to 60 |
| (7) sigma l-lactate$^-$/ plus pyruvate$^-$ | 0 to about 465 | 0 to 60 |
| (8) sigma d-betahydroxy- butyrate$^-$/plus acetoacetate$^-$ | 0 to about 465 | 0 to 60 |
| (9) sigma (6 + 7 + 8) | 0.1 to about 465 | 25 to 65 |
| Total nonionics | 0 to about 2400 | 0 to 305 |
| (10) carbon dioxide | 0 to about 25 | 1 to 5 |
| (11) osmotically active substances* | 0 to about 2400 | 0 to 300 |
| In Table III solutions the component interrelationships are always such that the following holds: | | |
| (12) mEq. ratio of bicarbonate$^-$/ $CO_2$ | about 0.1/1 to 55/0.1 | 0.1 to 55/0.1 |
| (13) mEq. ratio of l-lactate$^-$/ pyruvate$^-$ | about 20/1 to 1/1 | 10/1 to 5/1 |
| (14) mEq. ratio of d-betahydroxy- butyrate$^-$/ acetoacetate$^-$ | about 6/1 to 0.5/1 | 3/1 to 1.5/1 |
| (15) mEq. ratio of Na:Cl | about 1.24 to 1.60 | 1.24 to 1.6 |
| (16) Osmolarity of Solution | about 260 to 5000 | 280 to 545 |
| (17) pH of Solutions | about 5 to 9 | 5 to 9 |

*Glucose preferred

Optionally, solutions of this invention as shown in Table III can additionally contain:
 (a) from 0 to about 25 millimoles per liter of sigma inorganic phosphate (e.g. all inorganic phosphate, including mono-, di-, and trivalent phosphate ions), and
 (b) from 0 to about 2 millimoles per liter of sigma inorganic sulfate (e.g. all inorganic sulfate including non ionized dissolved salts).

The electrolyte solutions of such Table III, as indicated above, are useful in such applications as intravenous administration for replacement of electrolytes and fluids, for parenteral nutrition, for dialysis, and the like. For a particular field of use and/or end use applications, the formulation of any given solution can be optimized in accord with the desires of the formulator. Thus, in general, the present invention provides in one aspect an in vivo process which
 (a) tends to maintain a normal plasma milliequivalent ratio of sodium cations to chloride anions,
 (b) tends to maintain normal plasma and cellular pH, and
 (c) tends to maintain normal cellular cofactor ratios (that is, tends to maintain and regulate a normal cellular redox state and a normal cellular phosphorylation potential).

This process is practiced by introducing into a living mammal a physiologically effective amount of an aqueous solution as above characterized. Introducing can be accomplished by any known procedure as herein indicated. The physiologically effective amounts are as herein indicated.

Class I solutions which are particularly suited for electrolyte and fluid therapy are subgenerically characterized in Table IV below. Each Table IV solution comprises water which has dissolved therein each of the indicated components in the respective amount indicated. In this Table IV the "preferred" class of embodiments (so identified) can be regarded as being usable either as such, or as concentrates which can be further diluted so long as nonionic material is included to keep the final osmolarity above about 260/mOsmoles/L. In the latter case, the diluted solutions should contain added dissolved nonionic material (preferably glucose) with care being taken to preserve in the product diluted solution the various ratios, osmolarity and pH values, all as shown in such Table IV.

Such Class I solutions are used, in accord with this invention, in an in vivo process for accomplishing electrolyte and fluid therapy in a mammal. This process:
 (a) tends to maintain a normal plasma milliequivalent ratio of sodium cations to chloride anions,
 (b) tends to maintain normal plasma and cellular pH, and
 (c) tends to maintain normal cellular cofactor ratios.

This process comprises introducing intravenously into a mammal at a physiologically effective rate a quantity of such a solution in an amount which is not more than about 1 liter per 70 kilograms of mammal body weight per 24 hour day.

TABLE IV

Class I Solutions Particularly Suited for Electrolyte and Fluid Therapy

| Component | Composition at time of Administration Quantity Range (millimoles per liter) | |
|---|---|---|
| | broad | preferred |
| Total cations (mEq/L) | 1 to about 2400 | 130 to 170 |
| (1) sodium$^+$ | 1 to about 2400 | 130 to 165 |
| (2) potassium$^+$ | 0 to about 90 | 0 to 10 |
| (3) calcium$^{++}$ | 0 to about 60 | 0 to 5 |
| (4) magnesium$^{++}$ | 0 to about 15 | 0 to 3 |
| Total anions (mEq/L) | 1 to about 2400 | 130 to 170 |
| (5) chloride$^-$ | 0.6 to about 1935 | 80 to 130 |
| (6) bicarbonate$^-$ | 0 to about 465 | 0 to 60 |
| (7) sigma l-lactate/ plus pyruvate$^-$ | 0 to about 465 | 0 to 60 |
| (8) sigma d-betahydroxy- butyrate$^-$ plus acetoacetate$^-$ | 0 to about 465 | 0 to 60 |
| (9) sigma (6 + 7 + 8) | 0.4 to about 465 | 25 to 60 |
| Total nonionics | 0 to about 2400 | 0 to 300 |
| (10) carbon dioxide | 0 to about 25 | 0 to 5 |
| (11) osmotically active substances* | 0 to about 2400 | 0 to 300 |

In Table IV solutions, the component interrelationships are

TABLE IV-continued
Class I Solutions Particularly Suited for Electrolyte and Fluid Therapy

| Component | Composition at time of Administration Quantity Range (millimoles per liter) | |
|---|---|---|
| | broad | preferred |
| | always such that: | |
| (12) mEq. ratio of $HCO_3^-$/ $CO_2$ | about 0.1/1 to 55/0.1 | 12/1 to 85/1 |
| (13) mEq. ratio of l-lactate$^-$/ pyruvate$^-$ | about 20/1 to 1/1 | 10/1 to 5/1 |
| (14) mEq. ratio of d-betahydroxy butyrate$^-$/ acetoacetate$^-$ | about 6/1 to 0.5/1 | 3/1 to 1.5/1 |
| (15) mEq. ratio of Na:CL | about 1.24 to 1.6 | 1.26 to 1.6 |
| (16) Milliosmolarity of Solution | about 260 to 5000 | 260 to 540 |
| (17) pH of Solution | about 5 to 9 | 7 to 8 |

*glucose preferred

Class II solutions which are particularly suited for electrolyte and fluid therapy are subgenerically characterized in Table V below. As before, each Table V solution comprises water which has dissolved therein the indicated components in the respective amount indicated. In this Table V, the "preferred" class of embodiments (so identified) can be regarded as being representative of compositions which are now believed to be suitable for usage for example by hospitals and the like. In making and using all these solutions care should be taken to preserve the various ratios, osmolarity, and pH values, all as shown in such Table V.

Such Class II solutions are used, in accord with this invention in an in vivo process for accomplishing electrolyte and fluid therapy in a mammal. Parenteral nutrition optionally can be concurrently accomplished (depending upon the content of nutrients, such as nonionic osmotically active substances (like glucose, or other conventional additives, including amino acids). As with the process involving Class I solutions, this process:

(a) tends to maintain the normal plasma milliequivalent ratio of sodium cations to chloride anions, and
(b) tends to maintain normal plasma and cellular pH ratios, and
(c) tends to maintain normal cofactor ratios.

This process comprises intravascularly introducing into the blood of a mammal a physiologically effective amount of such a solution. The quantity introduced can vary per 24 hour day per patient depending upon the circumstances, patient condition, physicians purpose, and the like. No minimum or maximum definite limit on safe usage quantity is now known or believed to exist.

TABLE V
Generic Composition of Class II Solutions For Electrolyte and Fluid Therapy

| Component | Composition at time of Administration Quantity Range (millimoles per liter) | |
|---|---|---|
| | broad | preferred |
| Total cations (mEq/L) | 1 to about 170 | 136 to 170 |
| (1) sodium$^+$ | 1 to about 170 | 130 to 160 |
| (2) potassium$^+$ | 0 to about 10 | 3 to 5 |
| (3) calcium$^{++}$ | 0 to about 5 | 1 to 1.5 |
| (4) magnesium$^{++}$ | 0 to about 5 | 0.5 to 1.0 |
| Total anions | 1 to about 170 | 136 to 170 |

TABLE V-continued
Generic Composition of Class II Solutions For Electrolyte and Fluid Therapy

| Component | Composition at time of Administration Quantity Range (millimoles per liter) | |
|---|---|---|
| | broad | preferred |
| (5) chloride$^-$ | 0.6 to about 137 | 81 to 129 |
| (6) bicarbonate$^-$ | 0 to about 64 | 0 to 51 |
| (7) sigma l-lactate$^-$/ and pyruvate$^-$ | 0 to about 64 | 0 to 51 |
| (8) sigma d-betahydroxy-butyrate$^-$/and acetoacetate$^-$ | 0 to about 64 | 0 to 51 |
| (9) sigma (6 + 7 + 8) | 0.4 to about 64 | 25 to 51 |
| Total nonionics | about 0 to 625 | 0 to 305 |
| (10) carbon dioxide | about 0 to 25 | 0 to 5 |
| (11) osmotically active substances* | about 0 to 600 | 0 to 300 |
| In Table V solutions the component interrelationships are always such that: | | |
| (12) mEq. ratio of $HCO_3^-$/ $CO_2$ | about 0.1/1 to 55/0.1 | 0.1/1 to 55/0.1 |
| (13) mEq. ratio of l-lactate$^-$/ pyruvate$^-$ | about 20/1 to 1/1 | 10/1 to 5/1 |
| (14) mEq. ratio of d-betahydroxy-butyrate$^-$/ acetoacetate$^-$ | about 6/1 to 0.5/1 | 3/1 to 1.5/1 |
| (15) mEq. ratio of Na:Cl | about 1.24 to 1.6 | 1.24 to 1.6 |
| (16) Milliosmolarity of Solution | about 260 to 950 | 260 to 550 |
| (17) pH of Solution | about 5 to 9 | 5 to 9 |

*glucose preferred

Class II solutions which are particularly suited for use in dialysis (whether hemo- or peritoneal) are subgenerically characterized in Table VI below.

TABLE VI
Class II Solutions Particularly Suited for Dialysis (Hemo- & Peritoneal)

| Component | Composition at Time of Administration Quantity Range (millimoles per liter) | |
|---|---|---|
| | broad | preferred |
| Total cations (mEq/L) | about 130 to 170 | 136 to 155 |
| (1) sodium$^+$ | about 130 to 155 | 135 to 145 |
| (2) potassium$^+$ | 0 to about 5 | 0 to 4 |
| (3) calcium$^{++}$ | 0 to about 3 | 0 to 1.7 |
| (4) magnesium$^{++}$ | 0 to about 2 | 0.3 to 1 |
| Total anions (mEq/L) | about 130 to 170 | 136 to 155 |
| (5) chloride$^-$ | about 81 to 125 | 86 to 104 |
| (6) bicarbonate$^-$ | 0 to about 60 | 25 to 45 |
| (7) sigma l-lactate$^-$/plus pyruvate$^-$ | 0 to about 60 | 2 to 10 |
| (8) sigma d-betahydroxy-butyrate$^-$/plus acetoacetate$^-$ | 0 to about 60 | 1 to 5 |
| (9) sum (6 + 7 + 8) | about 25 to 60 | 27 to 55 |
| Total nonionics | 0 to about 525 | 11 to 280 |
| (10) carbon dioxide | 0 to about 25 | 0.5 to 2 |
| (11) osmotically active substance* | 0 to about 500 | 10 to 280 |
| In Table VI Solutions, the component interrelationships are always such that: | | |
| (12) mEq. ratio of $HCO_3^-$/ $CO_2$ | about 0.1/1 to 55/0.1 | 19/1 to 8/1 |
| (13) mEq. ratio of L-lactate$^-$/ pyruvate$^-$ | about 20/1 to 1/1 | 10/1 to 5/1 |
| (14) meq/ratio of D-beta hydroxybutyrate$^-$/ acetoacetate$^-$ | about 6/1 to 0.5/1 | 3/1 to 1.5/1 |

TABLE VI-continued

Class II Solutions Particularly Suited for Dialysis (Hemo- & Peritoneal)

| Component | Composition at Time of Administration Quantity Range (millimoles per liter) | |
|---|---|---|
| | broad | preferred |
| (15) mEq. ratio of Na:Cl | about 1.24 to 1.6 | 1.36 to 1.5 |
| (16) Milliosmolarity of Solution | about 260 to 850 | 280 to 320 |
| (17) pH of Solutions | about 5 to 9 | 7.35 to 8 |

*glucose preferred

Clase II solutions which are within the scope of Table VI above and which are particularly suited for hemodialysis are subgenerically characterized in Table VII below. As before, each Table VII solution comprises water which as dissolved therein the indicated components in the respective amounts indicated.

Such Class II solutions of Table VII are suitable for use in a hemodialysis process of the generally known and conventional type where renal function of a living mammal is replaced in whole or in part by dialysis. In hemodialysis, portions of the blood of such mammal are continuousy passed over one face of a dialysis membrane (which is incorporated preferably a high surface area cartridge-like structure) while the opposed face of such membrane is contacted with a dialysis fluid, thereby to achieve a change in the chemical composition of the body fluids after the so dialyzed blood is returned to the mammal's vascular system. Duration of a conventional hemodialysis can vary, depending upon equipment, conditions, patient condition, and the like, but typically can extend for a time of from about 3 to 5 hours. Optionally, but preferably, the dialysis membrane used in combination with the associated apparatus is such that the blood so passed over such membrane can be pressurized during such passage (typically and conventionally up to about 300 grams per cubic centimeter), thereby to produce what is known in the dialysis art as "ultrafiltration". In the conventional hemodialysis procedure, the dialysis fluid is an aqueous solution which contains dissolved therein the same principal inorganic electrolytes at respective individual concentration levels which approximate such major plasma electrolytes and their concentrations.

In the present hemodialysis one substitutes for the conventional dialysis fluid a solution of the present invention as above characterized in Table VII. Conventional dialysis equipment can be used, but a deaerator, such as might tend to eliminate dissolved carbon dioxide from a dialysis solution of this invention, should not be present. During use in peritoneal dialysis, a solution of this invention:

(a) tends to maintain a normal equivalent ratio of sodium cations to chloride anions, and
(b) tends to maintain normal cellular and plasma pH, and
(c) tends to maintain normal cofactor ratios.

The total quantity of such solution of this invention used in a given hemodialysis is comparable to the quantities used in prior art fluids employed under the same conditions (typically from about 35 to 160 liters of dialysis fluid per hemodialysis per man).

TABLE VII

Class II Solutions Particularly Suited for Hemodialysis

| Component | Composition at Time of Administration Quantity Range (millimoles per liter) | |
|---|---|---|
| | broad | preferred |
| Total cations (mEq/L) | about 130 to 170 | 134 to 154 |
| (1) sodium$^+$ | about 130 to 155 | 132 to 145 |
| (2) potassium$^+$ | 0 to about 5 | 0 to 4 |
| (3) calcium$^{++}$ | 0 to about 3 | 1 to 1.75 |
| (4) magnesium$^{++}$ | 0 to about 2 | 0.3 to 0.75 |
| Total anions (mEq/L) | about 130 to 170 | 134 to 154 |
| (5) chloride$^-$ | 84 to about 125 | 93 to 115 |
| (6) bicarbonate$^-$ | 0 to about 55 | 25 to 35 |
| (7) sigma L-lactate$^-$/ pyruvate$^-$ | 0 to about 55 | 0 to 12 |
| (8) sigma D-betahydroxy-butyrate$^-$/ acetoacetate$^-$ | 0 to about 55 | 0 to 5 |
| (9) sigma (6 + 7 + 8) | about 25 to 55 | 36 to 42 |
| Total nonionics* | about 0 to 525* | 0 to 12 |
| (10) carbon dioxide | about 0 to 25 | 0 to 2 |
| (11) osmotically active substance** | about 0 to 500* | 0 to 10 |
| In Table VII, the component interrelationships are always such that: | | |
| (12) mEq. ratio of bicarbonate$^-$/ CO$_2$ | about 0.1/1 to 55/0.1 | 18/1 to 35/0.5 |
| (13) mEq. ratio of L-lactate$^-$/ pyruvate$^-$ | about 20/1 to 1/1 | 10/1 to 5/1 |
| (14) mEq. ratio of D-beta-hydroxybutyrate$^-$/ acetoacetate$^-$ | about 6/1 to 0.5/1 | 3/1 to 1.5/1 |
| (15) mEq. ratio of Na:Cl | about 1.24 to 1.6 | 1.26 to 1.55 |
| (16) milliosmolarity of Solution | about 260 to 800 | 260 to 350 |
| (17) pH of Solution | about 5 to 9 | 7.35 to 8 |

*This upper limit used when the solution is being employed in an old type Kolff kidney where pressure cannot be exerted on the dialysis membrane. In a pressurized dialysis system the limit is about 0 to 11 mMol/l for glucose; if other nonionics are added, then preferred limit would be below about 20 mMol/l total.
**glucose preferred Class II solutions which are within this scope of Table VI above and which are particularly suited for peritoneal dialysis are subgenerically characterized in Table VIII below.

Such Class II solutions of Table VIII are suitable for use in a peritoneal dialysis process of the generally known and conventional types when renal function of a living mammal is replaced in whole or in part by dialysis. In peritoneal dialysis a quantity of a dialysis fluid is charged into the peritoneal cavity of such mammal for a time sufficient to achieve a change in the chemical composition of body fluids, after which the dialysate is drained or otherwise removed from the peritoneal cavity. Typical residence times for fluid in the peritoneal cavity range from about ½ to 1 hour, although longer and shorter times can be employed. Typically, peritoneal dialysis sessions last 4½ hours, but continuous ambulatory peritoneal dialysis has recently been advocated. The patient's own peritoneum serves as a dialysis membrane. In the conventional peritoneal dialysis procedure, the dialysis fluid is, as in the case of a hemodialysis fluid, an aqueous solution which contains dissolved therein the same principal inorganic electrolytes and at respective individual concentration levels which approximate those of major plasma electrolytes and their concentrations, except that in the case of peritoneal dialysis fluids a higher concentration of nonionics, such as glucose, is typically employed in order to provide as osmolarity which is greater than that of mammalian plasma, thereby to promote ion and water transfer through the peritoneum, all as known to those skilled in the art. Chronic, so called "ambulatory" peritoneal dialysis may also benefit from these solutions.

In the present invention, one substitutes for the conventional dialysis fluid a solution of the present invention as above characterized in Table VIII. During use in peritoneal dialysis, a solution of this invention:

(a) tends to maintain a normal equivalent ratio of sodium cations to chloride anions,
(b) tends to maintain normal plasma and cellular pH,
(c) tends to maintain normal cofactor ratios.

The quantity of such solution employed is comparable to the quantity used in prior art peritoneal dialysis as is the residence time in the peritoneal cavity.

TABLE VIII

Class II Solutions Particularly Suited for Peritoneal Dialysis

| | Compositions at Time of Administration Quantity Range (millimoles per liter) | |
|---|---|---|
| Component | broad | preferred |
| Total cations | about 130 to 170 | 135 to 150 |
| (1) sodium$^+$ | about 130 to 165 | 130 to 145 |
| (2) potassium$^+$ | about 0 to 5 | 0 to 4 |
| (3) calcium$^{++}$ | about 0 to 2 | 1 to 1.5 |
| (4) magnesium$^{++}$ | about 0 to 1.5 | 0.3 to 1 |
| Total anions | about 130 to 170 | 135 to 150 |
| (5) chloride$^-$ | about 81 to 130 | 93 to 102 |
| (6) bicarbonate$^-$ | about 0 to 55 | 25 to 30 |
| (7) sigma L-lactate$^-$/plus pyruvate$^-$ | about 0 to 55 | 2 to 12 |
| (8) sigma D-betahydroxybutyrate$^-$/acetoacetate$^-$ | about 0 to 55 | 1 to 5 |
| (9) sigma (6 + 7 + 8) | about 26 to 55 | 36 to 50 |
| Total nonionics* | about 40 to 252 | 84 to 238 |
| (10) carbon dioxide | about 0 to 25 | 0 to 2 |
| (11) osmotically active substance | about 40 to 250 | 83 to 237 |
| In Table VIII, the component interrelationships are always such that: | | |
| (12) mEq. ratio of HCO$_3^-$/CO$_2$ | about 0.1/1 to 160/1 | 19/1 to 21/1 |
| (13) mEq. ratio of L-lactate$^-$/pyruvate$^-$ | about 20/1 to 1/1 | 10/1 to 5/1 |
| (14) mEq. ratio of D-beta-hydroxybutyrate$^-$/acetoacetate$^-$ | about 6/1 to 0.5/1 | 3/1 to 1.5/1 |
| (15) mEq. ratio of Na:Cl | about 1.24 to 1.6 | 1.36–1.42 |
| (16) Milliosmolarity of Solution | about 310 to 615 | 350 to 520 |
| (17) pH of Solution | about 5 to 8 | 7.36 to 7.6 |

*glucose preferred

EMBODIMENTS

The following examples are merely illustrative of the present invention and are not intended as a limitation upon the scope thereof.

EXAMPLES 1 THROUGH 27

The following compositions of this invention illustrate electrolyte solutions of Class I (above identified) which are suitable for intravenous administration to replace electrolytes and fluid in a human adult patient at dose rates of, for example, 500 ml/patient/24 hour day. Each solution consists of water which has dissolved therein each of the identified in the respective specific per liter quantity shown components in the following Table IX.

Each solution is here prepared by dissolving substantially pure selected salt and nonionic material following the teaching of "Date for Biochemical Research", 1969, pp. 507–508. Each solution can be made from many different materials depending upon manufacturing convenience, ease of sterilization, cost of raw materials, and the like; the only requirement is that the final ionic composition of each solution should be as described.

The footnote for each example in Table IX characterizes the composition and provides a suggested application or use.

Also shown in Table IX are further examples of prior art solutions. All solutions are listed as Type 1 a, b, c, and d, in conformity with the classification herein developed.

TABLE IX

Case 1

Class 1a

Solutions Containing 1 or 2 Cations from Among Na$^+$, K$^+$, Mg$^{2+}$ or Ca$^{2+}$ with no Nutrients (Glucose) and No HCO$_3^-$/CO$_2$

| Units mmoles L fluid | Normal Plasma N.E.J.M. 283, 1285 1970 | 1 a 1 "Normal" 0.9% NaCl U.S. | 1 a 2 "Normal" 0.95% NaCl U.K. | 1 a 3 Isotonic NaLactate Salt | 1 1 a 4 Isotonic NaLact/Pyr Salt | 2 1 a 5 Isotonic NaLact/Pyr-BHB/acac | 3 1 a 6 Isotonic Na BHB/acac Salt |
|---|---|---|---|---|---|---|---|
| Na | 136–145 | 155 | 162.5 | 160.3 | 153 | 155 | 152.5 |
| K | 3.5–5.0 | | | | | | 2.5 |
| Ca | 2.1–2.6 | | | | 1 | | |
| free [Ca$^{2+}$] | [1.06] | | | | | | |
| Mg | 0.75–1.25 | | | | | | |
| free [Mg$^{2+}$] | [0.53] | | | | | | |

TABLE IX-continued

Case 1

| | | | | | | | |
|---|---|---|---|---|---|---|---|
| Σ mEq Cations | 142.7–153.2 | 155 | 162.5 | 160.3 | 155 | 155 | 155 |
| Cl | 100–106 | 155 | 162.5 | 108.3 | 106 | 106 | 106 |
| $HCO_3$ | 26–28 | | | | | | |
| ΣPi | 1–1.45 | | | | | | |
| $SO_4$ | 0.32–0.94 | | | | | | |
| L - lactate | 0.6–1.8 | | | 52 (d,l) | 44 | 38 | |
| pyruvate | | | | | 5 | 5 | |
| Lact/pyr | | | | ∞ | 8.8 | 9.5 | |
| D B OHbutyrate | | | | | | 4.7 | 35 |
| acetoacetate | | | | | | 2.3 | 14 |
| B HB/acac | | | | | | 2.0 | 2.5 |
| acetate | | | | | | | |
| Other | | | | | | | |
| Σ mEq anions | 128.7–139.4 | 155 | 162.5 | 160.3 | 155 | 155 | 155 |
| Na/Cl | 1.28–1.45 | 1.00 | 1.00 | 1.48 | 1.44 | 1.46 | 1.44 |
| Glucose or others | 3.9–5.6 | | | | | | |
| $CO_2$ | 0.99–1.39 | | | | | | |
| pH | 7.35–7.45 | ~5.5–6.5 | ~5.5–6.5 | ~6.5 | ~6.5 | ~6.5 | ~6.5 |
| Σ mOsm | 285–295 | 310 | 325 | 321 | 310 | 310 | 310 |
| Use: | | I.V. electrolyte replacement | same as 1a1 | Used to prevent acidosis | Improves 1a1, 1a2 1a3 with $Ca^{2+}$ | Redox control of cytoplasm & mitochondria | Alternative to 1a4 with K |

1.a.1. Most common electrolyte solution given in U.S. Tends of cause hyperchloremic acidosis because of abnormal Na/Cl ratio. See Black DAK. Lancet i, 353, 1952.
1.a.2. Used in U.K. and Canada.
1.a.3. Darrow et al. J Am Med Ass 143: 365, 432, 1944. Causes redox imbalance.
1.a.4. | |- Solutions in boxes are new in this disclosure.

Class 1b
Solutions Containing 1 or 2 Cations from Among $Na^+$, $K^+$, $Mg^{2+}$, $Ca^{2+}$ with $HCO_3^-$ or $HCO_3^-/CO_2$ and No Nutrients

| Units mmoles L fluid | Normal Plasma N.E.J.M. 283, 1285 1970 | 1 b 1 Isotonic $NaHCO_3^-$ Salt | 4 1 b 2 Isotonic $NaHCO_3/CO_2+$ Lact/Pyr | 5 1 b 3 Isotonic NaLact/pyr+ NaCl + Ca | 6 1 b 4 Isotonic NaL/P-B/A- $HCO_3/CO_2$ | 7 1 b 5 1 b 4 with $K^+$ |
|---|---|---|---|---|---|---|
| Na | 136–145 | 160.3 | 155 | 153 | 155 | 152 |
| K | 3.5–5.0 | | | | | 3 |
| Ca | 2.1–2.6 | | | 1 | | |
| free [$Ca^{2+}$] | [1.06] | | | | | |
| Mg | 0.75–1.25 | | | | | |
| free [$Mg^{2+}$] | [0.53] | | | | | |
| Σ mEq Cations | 142.7–153.2 | 160.3 | 155 | 155 | 155 | 155 |
| Cl | 100–106 | 108.3 | 106 | 106 | 106 | 106 |
| $HCO_3$ | 26–28 | 52 | 27 | 27 | 27 | 27 |
| ΣPi | 1–1.45 | | | | | |
| $SO_4$ | 0.32–0.94 | | | | | |
| L - lactate | 0.6–1.8 | | 19 | 19 | 13 | 13 |
| pyruvate | | | 3 | 3 | 2 | 2 |
| Lact/pyr | | | 6.3 | 6.3 | 6.5 | 6.5 |
| D B OHbutyrate | | | | | 5 | 4 |
| acetoacetate | | | | | 2.5 | 3 |
| B HB/acac | | | | | 2.5 | 1.3 |
| acetate | | | | | | |
| Other | | | | | | |
| Σ mEq anions | 128.7–139.4 | 160.3 | 155 | 155 | 155 | 155 |
| Na/Cl | 1.28–1.45 | 1.48 | 1.46 | 1.44 | 1.46 | 1.43 |
| Glucose or others | 3.9–5.6 | | | | | |
| $CO_2$ | 0.99–1.39 | — | 1.3 | 1.3 | 1.3 | 1.3 |
| pH | 7.35–7.45 | 8.6 | 7.35 | 7.35 | 7.35 | 7.35 |
| Σ mOsm | 285–295 | 321 | 311 | 311 | 311 | 311 |

TABLE IX-continued

Case 1

Use:

1 b 1 Darrow et al J Am Med Ass 143: 365, 432, 1944, abnormal pH. Incompatible with $Mg^{2+}$ and $Ca^{2+}$.

Class 1c
Solutions Containing 1 or 2 Cations from Among $Na^+$, $K^+$, $Mg^{2+}$ or $Ca^{2+}$ with Non-Ionic Nutrients*

| Units mmoles L fluid | Normal Plasma N.E.J.M. 283, 1285 1970 | 1 c 1 5% Dextrose + $H_2O$ U.S. | 1 c 2 5.25% Glucose U.K. | 1 c 3 Isotonic Glucose 2+ NaCl 1 | 1 c 4 Glucose NaLactate- NaCl | 8 1 c 5 Glucose NaLact/Pyr- NaCl | 9 1 c 6 Glucose + Ketones + NaCl | 10 1 c 7 Redox Balanced 2 Gluc + 1 NaCl |
|---|---|---|---|---|---|---|---|---|
| Na | 136–145 | | | 54.1 | 53.4 | 53.4 | 52.4 | 53.4 |
| K | 3.5–5.0 | | | | | | | |
| Ca | 2.1–2.6 | | | | | | | |
| free [$Ca^{2+}$] | [1.06] | | | | | | | |
| Mg | 0.75–1.25 | | | | | | 0.5 | |
| free [$Mg^{2+}$] | [0.53] | | | | | | | |
| mEq Cations | 142.7–153.2 | 0 | 0 | 54.1 | 53.4 | 53.4 | 53.4 | 53.4 |
| Cl | 100–106 | | | 54.1 | 36.1 | 36.1 | 36.1 | 36.1 |
| $HCO_3$ | 26–28 | | | | | | | |
| Pi | 1–1.45 | | | | | | | |
| $SO_4$ | 0.32–0.94 | | | | | | | |
| L - lactate | 0.6–1.8 | | | | 1.73 (d,l) | 15.3 | | 10 |
| pyruvate | | | | | | 2 | | 2 |
| Lact/pyr | | | | | ∞ | 7.7 | | 5 |
| D B OHbutyrate | | | | | | | 12 | 3.3 |
| acetoacetate | | | | | | | 5.3 | 2 |
| B HB/acac | | | | | | | 2.3 | 1.65 |
| acetate | | | | | | | | |
| Other | | | | | | | | |
| mEq anions | 128.7–139.4 | 0 | 0 | 54.1 | 53.4 | 53.4 | 53.4 | 53.4 |
| Na/Cl | 1.28–1.45 | — | — | 1.00 | 1.48 | 1.48 | 1.45 | 1.48 |
| Glucose or others | 3.9–5.6 | 278 | 292 | 195 | 195 | 195 | 195 | 195 |
| $CO_2$ | 0.99–1.39 | | | | | | | |
| pH | 7.35–7.45 | ~6.5 | ~6.5 | ~6.5 | ~6.5 | ~6.5 | ~6.5 | ~6.5 |
| mOsm | 285–295 | 278 | 292 | 301 | 302 | 302 | 302 | 302 |
| Use: | | fluid replacement + nutrients | same as 1 c 2 | NaCl, $H_2O$ replacement + calories | Prevent hyperchloremia | Corrects redox imbalance in 1 c 4 | Alternative also for status epilepticus | Improves 1 c 5 |

*Common non-ionic nutrients are 5%, 2.5%, 10% glucose. Additional similar fructose and glycerol solutions in over 20 mM amounts are approved by FDA, but not recommended here. (See "Safe Entry Points")

1 c 1 - Most common I.V. fluid given. Merck Handbook 1966, p 1867. This is combined with isotonic NaCl in many proportions.

1 c 2 - Used in the U.K. and Canada where "isotonic" is different than in the U.S. - presumably. See Geigy Handbook, 1970, p 334.

1 c 3 - 2 parts isotonic glucose plus 1 part isotonic NaCl - Geigy Handbook 1970, p 334.

1 c 4 - Prevents hyperchloremia but causes redox imbalance. Geigy Handbook 1970, p 334.

| Units mmoles L fluids | Normal Plasma N.E.J.M. 283, 1285 1970 | 11 1 c 8 2L D5W + 0.5L Normal Saline + Redox Balance | 12 1 c 9 11 with K | 1 c 10 D 5 W + 0.9% NaCl | 1 c 11 10% Glucose + 0.9% NaCl | 1 c 12 2.5% Glucose + 0.45% NaCl | 13 1 c 13 D5W + L/P Saline | 14 1 c 14 D10W + BHB/Acac + Saline | 15 1 c 15 D5W + Redox Balance |
|---|---|---|---|---|---|---|---|---|---|
| Na | 136–145 | 31 | 31 | 154 | 154 | 77 | 154 | 154 | 154 |
| K | 3.5–5.0 | | 5.0 | | | | | | |
| Ca | 2.1–2.6 | | | | | | | | |
| free [$Ca^{2+}$] | [1.06] | | | | | | | | |
| Mg | 0.75–1.25 | | | | | | | | |
| free [$Mg^{2+}$] | [0.53] | | | | | | | | |

TABLE IX-continued

Case 1

| | | | | | | | | | |
|---|---|---|---|---|---|---|---|---|---|
| Σ mEq Cations | 142.7–153.2 | 31 | 36 | 154 | 154 | 77 | 154 | 154 | 154 |
| Cl | 100–106 | 22 | 22 | 154 | 154 | 77 | 105 | 105 | 105 |
| $HCO_3$ | 26–28 | | | | | | | | |
| ΣPi | 1–1.45 | | | | | | | | |
| $SO_4$ | 0.32–0.94 | | | | | | | | |
| | | | | | | | | | |
| L - lactate | 0.6–1.8 | 7 | 10 | | | | 43 | | 36 |
| pyruvate | | 1 | 1.43 | | | | 6 | | 6 |
| Lact/pyr | | 7 | 7 | | | | 7.2 | | 7 |
| D B OHbutyrate | | 0.66 | 1.57 | | | | | 29 | 4 |
| acetoacetate | | 0.33 | 1.00 | | | | | 20 | 3 |
| B HB/acac | | 2 | 1.6 | | | | | 1.5 | 1.3 |
| acetate | | | | | | | | | |
| Other | | | | | | | | | |
| | | | | | | | | | |
| Σ mEq anions | 128.7–139.4 | 31 | 36 | 154 | 154 | 77 | 154 | 154 | 154 |
| Na/Cl | 1.28–1.45 | 1.41 | 1.41 | 1.00 | 1.00 | 1.00 | 1.47 | 1.47 | 1.47 |
| Glucose or others | 3.9–5.6 | 222.4 | 222.4 | 278 | 556 | 139 | 278 | 556 | 278 |
| $CO_2$ | 0.99–1.39 | | | | | | | | |
| pH | 7.35–7.45 | ~6.5 | ~6.5 | ~5.5–6.5 | ~5.5–6.5 | ~5.5–6.5 | ~5.5–6.5 | ~5.5–6.5 | ~5.5–6.5 |
| Σ mOsm | 285–295 | 284 | 284 | 561 | 813 | 293 | 561 | 864 | 561 |
| | | | | | | | | | |
| Use: | | | | | | | Improves 1 c 10 with Redox & Na/Cl Balance | Improves 1 c 11 | Improves 1 c 13 |

1 c 8. Improves with normal Na/Cl ratio and redox balance the most common routine I.V. order in the U.S.

1 c 9. Replaces 12.5 mEq of the 40 mEq of $K^+$ lost/day when given at the usual rate of 2.5L/day.

1 c 10. Facts and Comparisons Oct. 81, p. 51, Lippincott, St Louis 1 c 11. Facts and Comparisons Oct. 81, p. 51, Lippincott, St Louis 1 c 12. Facts and Comparisons Oct. 81, p. 51, Lippincott, St Louis

Class 1d
Solutions Containing 1 or 2 Cations from Among $Na^+$, $K^+$, $Mg^{2+}$, or $Ca^{2+}$ plus Non-ionic Nutrients Plus $HCO_3^-/CO_2$

| Units mmoles L fluid | Normal Plasma N.E.J.M. 283, 1285 1970 | 16 1 d 1 $HCO_3^-/CO_2$ Saline | 17 1 d 2 $HCO_3^-/CO_2$ Saline + K | 18 1 d 3 $HCO_3^-/CO_2$ Saline + Mg | 19 1 d 4 $HCO_3^-/CO_2$ Saline + Ca | 20 1 d 5 L/P $HCO_3/CO_2$ Saline | 21 1 d 6 L/P $HCO_3/CO_2$ Saline + K | 22 1 d 7 Redox Bal. Saline $HCO_3$ + 5% Gluc. | 23 1 d 8 Redox Bal. Saline $HCO_3$ + 2.5% Gluc |
|---|---|---|---|---|---|---|---|---|---|
| Na | 136–145 | 155 | 155 | 155 | 155 | 145 | 145 | 141 | 140 |
| K | 3.5–5.0 | | 5 | | | | 4 | | 4 |
| Ca | 2.1–2.6 | | | | | | | | |
| free $[Ca^{2+}]$ | [1.06] | | | | 1.5 | | | | |
| Mg | 0.75–1.25 | | | 1.0 | | | | | |
| free $[Mg^{2+}]$ | [0.53] | | | | | | | | |
| | | | | | | | | | |
| Σ mEq Cations | 142.7–153.2 | 155 | 160 | 156 | 158 | 145 | 149 | 141 | 144 |
| Cl | 100–106 | 107 | 107 | 107 | 107 | 106 | 106 | 100 | 104 |
| $HCO_3$ | 26–28 | 48 | 53 | 49 | 51 | 29 | 29 | 29 | 29 |
| ΣPi | 1–1.45 | | | | | | | | |
| $SO_4$ | 0.32–0.94 | | | | | | | | |
| | | | | | | | | | |
| L - lactate | 0.6–1.8 | | | | | 8.8 | 12.5 | 7 | 7 |
| pyruvate | | | | | | 1.2 | 1.5 | 1 | 1 |
| Lact/pyr | | | | | | 7.3 | 8 | 7 | 7 |
| D B OHbutyrate | | | | | | | | 2 | 2 |
| acetoacetate | | | | | | | | 1 | 1 |
| B HB/acac | | | | | | | | 2 | 2 |
| acetate | | | | | | | | | |
| Other | | | | | | | | | |

TABLE IX-continued

Case 1

| | | | | | | | | | |
|---|---|---|---|---|---|---|---|---|---|
| Σ mEq anions | 128.7–139.4 | 155 | 160 | 156 | 158 | 145 | 149 | 141 | 144 |
| Na/Cl | 1.28–1.45 | 1.45 | 1.45 | 1.45 | 1.45 | 1.37 | 1.37 | 1.41 | 1.35 |
| Glucose or others | 3.9–5.6 | 10 (optional) | 10 | 10 | 10 | 10 | 10 | 278 | 139 |
| $CO_2$ | 0.99–1.39 | 2.7 | 2.75 | 2.71 | 2.74 | 1.45 | 1.45 | 1.45 | 1.45 |
| pH | 7.35–7.45 | 7.35 | 7.35 | 7.35 | 7.35 | 7.4 | 7.4 | 7.4 | 7.4 |
| Σ mOsm | 285–295 | 320 | 330 | 322 | 328 | 290 | 298 | 560 | 427 |
| Use: | | Improves normal NaCl leaves patient alkolotic | Replaces K loss | $Mg^{2+}$ does not precipitate | $Ca^{2+}$ does not ppt. as with $HCO_3^-$ alone. | | | | |

Class 1d
Solutions Containing 1 or 2 Cations, to which is added $HCO_3^-/CO_2$ and Non-ionic Nutrients

| | Normal Plasma N.E.J.M. | 24<br>1 d 9<br>2L D5W<br>+ 0.5L R.B.<br>Saline | 25<br>1 d 10<br>2L D5W<br>+ 0.5L R.B.<br>Saline + K | 26<br>1 d 11<br>R.B. Saline with K & 2.5% Gluc. & No added $CO_2$ | 27<br>1 d 12<br>Like 1d11 but BHB acid added to make $CO_2$ in situ |
|---|---|---|---|---|---|
| Units | | | | | |
| mmole | 283, 1285 | | | | |
| L fluid | 1970 | | | | |
| Na | 136–145 | 28.2 | 28.2 | 140 | 140 |
| K | 3.5–5.0 | | 5 | 4 | 4 |
| Ca | 2.1–2.6 | | | | |
| free [$Ca^{2+}$] | [1.06] | | | | |
| Mg | 0.75–1.25 | | | | |
| free [$Mg^{2+}$] | [0.53] | | | | |
| Σ mEq Cations | 142.7–153.2 | 28.2 | 33.2 | 144 | 144 |
| Cl | 100–106 | 20 | 20 | 104 | 104 |
| $HCO_3$ | 26–28 | 5.8 | 10.8 | 29 | 29 |
| ΣPi | 1–1.45 | | | | |
| $SO_4$ | 0.32–0.94 | | | | |
| L - lactate | 0.6–1.8 | 1.4 | 1.4 | 5 | 7 |
| pyruvate | | 0.2 | 0.2 | 1 | 1 |
| Lact/pyr | | 7 | 7 | *7 | 7 |
| D B OHbutyrate | | 0.4 | 0.4 | 2 | * |
| acetoacetate | | 0.2 | 0.2 | 1 | 1 |
| B HB/acac | | 2 | 2 | 2 | 2 |
| acetate | | | | | |
| Other | | | | *2 Hlactate | *2 d B hydroxybutyric acid |
| Σ mEq anions | 128.7–139.4 | 28.2 | 33.2 | 144 | 144 |
| Na/Cl | 1.28–1.45 | 1.41 | 1.41 | 1.35 | 1.35 |
| Glucose or others | 3.9–5.6 | 222.4 | 222.4 | 139 | 139 |
| $CO_2$ | 0.99–1.39 | 0.29 | 0.54 | *— | *— |
| pH | 7.35–7.45 | 7.4 | 7.4 | ~7.4 | ~7.4 |
| Σ mOsm | 285–295 | 279 | 289 | 427 | 427 |
| Use: | | Replaces 2l D5W & 0.5l Normal Saline | & Replaces K loss | | |

1 d 11 *L Lactic acid is added instead of $CO_2$ to generate $CO_2$ in situ.
1 d 12 *D B Hydroxybutryric acid is added to generate $CO_2$ in situ.

EXAMPLES 28 THROUGH 41

The following compositions of this invention illustrate electrolyte solutions of Class II (above identified) which are suitable for (a) intravenous use to replace electrolytes and fluid (b) providing parenteral nutrition in a human adult patient, (c) peritoneal dialysis, and (d) hemodialysis. Dose rates can vary. Each solution consists of water which has dissolved therein each of the identified components in the respective specified concentrations per liter quantity shown in the following Table X. Each solution is prepared by conventional procedures. (See text of Examples 1 through 27).

The footnote for each sample in Table X characterizes the composition and provides a suggested application or use.

These compositions demonstrate, as do Tables V through VIII (above), that there is no essential compositional difference between these various solutions.

Table XI shows prior art hemodialysis fluids for comparison purposes in dialyzing a human adult patient using, for example, an apparatus as described by Miller J. H., Schinaberger J. H., Kraut J. A., and Gardner P. S., *Trans. Am. Soc. Artif. Intern. Organs* 25, 404–408, 1979.

In these solutions which contain dissolved $CO_2$, no deaerator should be used on the dialysis equipment.

TABLE X

Class 2a Electrolyte Fluids Containing 3 or 4 Cations Suitable for Contacting Cells, Containing No $HCO_3^-/CO_2$ and No Glucose; eg. after S. J. Ringer, Physiol 4: 29, 223, 1883, and 7: 291, 1886.

| Units mmoles L fluid | Normal Plasma N.E.J.M. 283, 1285 1970 | 2. a. 1. Ringer's Injection U.S. | 2. a. 2. Lactated Ringer's | 2. a. 3. Lactated Ringer's (Commercial) | 2. a. 4. Acetated Ringer's U.S. | 2. a. 5. Lact/Acet Ringer's | 28 2. a. 6. Lact/Pyr Ringer's | 29 2. a. 7. dB-HB/acac Ringer's | 30 2. a. 8. Redox Balanced Ringer's |
|---|---|---|---|---|---|---|---|---|---|
| Na | 136–145 *(137–145) | 147 | 129.8 | 130 | 130 | 140 | 130 | 130 | 130 |
| K | 3.5–5.0 | 4 | 5.4 | 4 | 4 | 10 | 4 | 4 | 4 |
| Ca free [Ca2+] | 2.1–2.6 [1.06] | 2.5 | 0.9 | 1.5 | 1.5 | 2.5 | 1.5 | 1.5 | 1.5 |
| Mg free [Mg2+] | 0.75–1.25 [0.53] | | 1.0 | | | 1.5 | | | |
| ΣmEq Cations | 142.7–153.2 | 156 | 139 | 137 | 137 | 158 | 137 | 137 | 137 |
| Cl | 100–106 *(100–110) | 156 | 111.8 | 109 | 109 | 103 | 96 | 96 | 96 |
| $HCO_3$ | 26–28 | | | | | | | | |
| ΣPi | 1–1.45 | | | | | | | | |
| $SO_4$ | 0.32–0.94 | | | | | | | | |
| L-lactate | 0.6–1.8 | | 27.2 (d,l) | 28 (d,l) | | 27.5 (d,l) | 35.9 | | 30 |
| pyruvate | | | | | | | 5.1 | | 4 |
| Lact/pyr | | | oo | oo | | oo | 7 | | 7.5 |
| D B OHbutyrate | | | | | | | | 27.3 | 5 |
| acetoacetate | | | | | | | | 13.7 | 2 |
| B HB/acac | | | | | | | | 2 | 2.5 |
| acetate | | | | | 28 | 27.5 | | | |
| Other | | | | | | | | | |
| ΣmEq anions | 128.7–139.4 | 156 | 139 | 137 | 137 | 158 | 137 | 137 | 137 |
| Na/Cl | 1.28–1.45 *(1.245–1.45) | 0.94 | 1.16 | 1.19 | 1.19 | 1.36 | 1.35 | 1.35 | 1.35 |
| Glucose or others | 3.9–5.6 | | | | | | | | |
| $CO_2$ | 0.99–1.39 | | | | | | | | |
| pH | 7.35–7.45 | | | | | | | | |
| ΣmOsm | 285–295 | 309 | 276 | 272 | 272 | 312 | 272.5 | 272.5 | 272.5 |
| Use: | | I.V. fluid | I.V. fluid | I.V. fluid | I.V. fluid | I.V. fluid | Improves 2 a 3. | Improves 2 a 4 | Improves 2 a 3, 2 a 6, 2 a 7. |

*N.I.H. Path & Blood Bank Guide, Revised Nov 1, '82.
2. a. 1. Facts and Comparisons p50, Oct '81, Lippincott
2. a. 2. Hartmann A F. J. Am. Med. Ass. 103: 1349, 1934.
2. a. 3. Facts and Comparisons p50, Oct '81, Lippincott. Widely used in blood product administration and surgery
2. a. 4. Facts and Comparisons p50, Oct '81, Lippincott.
2. a. 5. Fox et al. J. Am. Med. Ass. 148: 827, 1952. Corrects abnormal Na/Cl ratio but by use of pathogenic organic anions.

Solutions with Bold numbers and in boxes are new disclosures.

| Units mmoles L fluid | Normal Plasma N.E.J.M. 283, 1285 1970 | 31 2 a 9 Redox Balanced Ringer's & High K | 2 a 10 Ionosol D-CM (Abbott) | 2 a 11 Plasmalyte (Travenol) | 2 a 12 Isolyte S (McGaw) | 2 a 13 PolyonicR148 (Cutter) | 2 a 14 Delbecco's Pi Buffered Saline | 2 a 15 Krebs Ringer Phosphate |
|---|---|---|---|---|---|---|---|---|
| Na | 136–145 | 140 | 138 | 140 | 140 | 140 | 152 | 150.76 |
| K | 3.5–5.0 | 10 | 12 | 10 | 5 | 10 | 4.17 | 5.92 |
| Ca free [Ca2+] | 2.1–2.6 [1.06] | 1.0 | 2.5 | 2.5 | | 2.5 | 0.9 | 2.54 |

TABLE X-continued

| | | | | | | | | |
|---|---|---|---|---|---|---|---|---|
| Mg | 0.75–1.25 | 0.5 | 1.5 | 1.5 | 1.5 | 1.5 | 0.45 | 1.18 |
| free [Mg2+] | [0.53] | | | | | | | |
| ΣmEq Cations | 142.7–153.2 | 153 | 158 | 158 | 148 | 158 | 159.15 | 164.12 |
| Cl | 100–106 | 103 | 108 | 103 | 98 | 103 | 140.5 | 131.51 |
| HCO3 | 26–28 | | | | | | | |
| ΣPi | 1–1.45 | | | | | | 9.8 | 17.38 |
| SO4 | 0.32–0.94 | | | | | | 0.45 | 1.18 |
| L-lactate | 0.6–1.8 | 38 | 50 (d,l) | 8 (d,l) | | | | |
| pyruvate | | 5 | | | | | | |
| Lact/pyr | | 7.6 | oo | oo | | | | |
| D B | | 5 | | | | | | |
| OHbutyrate | | | | | | | | |
| acetoacetate | | 2 | | | | | | |
| B HB/acac | | 2.5 | | | | | | |
| acetate | | | 47 | 27 | 49 | | | |
| Other | | | | 23 gluconate | 4 citrate | | | |
| ΣmEq anions | 128.7–139.4 | 153 | 158 | 158 | 148 | 158 | 159.18 | 163.97 |
| Na/Cl | 1.28–1.45 | 1.36 | 1.28 | 1.36 | 1.43 | 1.40 | 1.08 | 1.15 |
| Glucose or others | 3.9–5.6 | | | | | | | |
| CO2 | 0.99–1.39 | | | | | | | |
| pH | 7.35–7.45 | | | | | | 7.4 | 7.4 |
| ΣmOsm | 285–295 | 304.5 | 312 | 312 | 294 | 315 | 308.3 | 311.65 |
| Use: | | Improves 2 a 5, lowers Ca & Mg to normal | I.V. electrolyte therapy | Same as 2 a 10 redox imbalance | Same as 2 a 10 PPi accumulation | Same as 2 a 10 imbalance of NADP/NADPH | Tissue culture salt mix | Biochemical experiments |

2 a 10. Facts and Comparisons Oct '81, p50
2 a 11. Facts and Comparisons Oct '81, p50
2 a 12. Facts and Comparisons Oct '81, p50
2 a 13. Facts and Comparisons Oct '81, p50
2 a 14. Delbecco R, Vogt M. J Exp Med 99: 167–182, 1954
2 a 15. Krebs H A. Hoppe-Seyle's Z Physiol Chem 217: 193, 1933

Class 2b Electrolyte Fluids Containing 3 to 4 Cations Suitable for Contacting Cells Also Containing $HCO_3^-/CO_2$ and No Glucose after Krebs H A & Henseleit K A, Hoppe-Seyler's Z Physiol Chem 210: 33–66, 1932.

| Units mmoles L fluid | Normal Plasma N.E.J.M. 283, 1285 1970 | 2 b 1 Krebs Henseleit | 32 2 b 2 Redox Balanced Ringer's $HCO_3/CO_2$ | 33 2 b 3 Redox Balanced Ringer's & $HCO_3/CO_2$ & Mg | 34 2 b 4 High $HCO_3$ Ringer sine Redox Balance | 35 2 b 5 L/P Ringer's Lactate $HCO_3/CO_2$ | 36 2 b 6 Ringer's Ketones $HCO_3/CO_2$ |
|---|---|---|---|---|---|---|---|
| Na | 136–145 | 143 | 130 | 136 | 136 | 130 | 130 |
| K | 3.5–5.0 | 5.9 | 4 | 4 | 4 | 4 | 4 |
| Ca | 2.1–2.6 | 2.5 | 1.5 | 1 | 1 | 1.5 | 1.5 |
| free [Ca2+] | [1.06] | | | | | | |
| Mg | 0.75–1.25 | 1.2 | | 0.5 | 0.5 | | |
| free [Mg2+] | [0.53] | | | | | | |
| ΣmEq Cations | 142.7–153.2 | 156.3 | 137 | 143 | 143 | 137 | 137 |
| Cl | 100–106 | 127.8 | 96 | 100 | 100 | 96 | 96 |
| HCO3 | 26–28 | 25 | 29 | 29 | 43 | 29 | 29 |
| ΣPi | 1–1.45 | 1.18 | | | | | |
| SO4 | 0.32–0.94 | 1.2 | | | | | |
| L-lactate | 0.6–1.8 | | 7 | 9 | | 10.5 | |
| pyruvate | | | 1 | 1 | | 1.5 | |
| Lact/pyr | | | 7 | 9 | | 7 | |
| D B | | | 3 | 3 | | | 8 |
| OHbutyrate | | | | | | | |
| acetoacetate | | | 1 | 1 | | | 4 |
| B HB/acac | | | 3 | 3 | | | 2 |
| acetate | | | | | | | |
| Other | | | | | | | |

TABLE X-continued

| | | | | | | | |
|---|---|---|---|---|---|---|---|
| ΣmEq anions | 128.7–139.4 | 157.3 | 137 | 143 | 143 | 137 | 137 |
| Na/Cl | 1.28–1.45 | 1.12 | 1.35 | 1.36 | 1.36 | 1.35 | 1.35 |
| Glucose or others | 3.9–5.6 | | | | | | |
| $CO_2$ | 0.99–1.39 | 1.24 | 1.5 | 1.5 | 2.46 | 1.5 | 1.5 |
| pH | 7.35–7.45 | | 7.4 | 7.4 | 7.4 | 7.4 | 7.4 |
| ΣmOSm | 285–295 | 308 | 274 | 286 | 286 | 274 | 274 |
| Use: | | Tissue incubation, organ perfusion | To replace all previous Lactated Ringer's | For blood replacement | For Rx of acidosis | Alternate to 2 b 2 | Alternate to 2 b 5 |

2 b 2 to 2 b 6. All these solutions would be suitable, given added glucose, for peritoneal dialysis, ie like class 2 c. As it is, these solutions would improve existing hemodialysis.

Class 2c Electrolyte Fluids Containing 3 or 4 Cations Suitable for Contacting Cells Containing No $HCO_3^-/CO_2$ to which are Added Non-ionic nutrients such as Glucose, Fructose, Glycerol etc.

| Units mmoles L fluid | Normal Plasma N.E.J.M. 283,1285 1970 | 2 c 1 Lactated Ringer's 5% Glucose | 2 c 2 ½ Strength Lactated Ring + 2.5% Gl | 2 c 3 Acetated Ringers & 5% Glucose | 2 c 4 Ionosol B & 5% Glucose (Abbott) | 2 c 5 Dianeal & 1.5% Glucose (Travenol) | 2 c 6 Peritoneal Dialysis 4.25% Gluc (Am. McGaw) | 2 c 7 Dianeal K-141 & 4.25% Glucose (Travenol) |
|---|---|---|---|---|---|---|---|---|
| Na | 136–145 | 130 | 65 | 130 | 57 | 141 | 141.5 | 132 |
| K | 3.5–5.0 | 4 | 2 | 4 | 25 | | | 4 |
| Ca | 2.1–2.6 | 1.5 | 0.75 | 1.5 | | 1.75 | 2.0 | 1.875 |
| free [Ca2+] | [1.06] | | | | | | | |
| Mg | 0.75–1.25 | | | | 2.5 | 0.75 | 0.75 | 0.75 |
| free [Mg2+] | [0.53] | | | | | | | |
| ΣmEq Cations | 142.7–153.2 | 137 | 68.5 | 137 | 87 | 146 | 147 | 141 |
| Cl | 100–106 | 109 | 55 | 109 | 49 | 101 | 102.5 | 106 |
| $HCO_3$ | 26–28 | | | | | | | |
| ΣPi | 1–1.45 | | | | 6.5 $H_2PO_4^-$ | | | |
| $SO_4$ | 0.32–0.94 | | | | | | | |
| L-lactate | 0.6–1.8 | 28 (d,l) | 14 (d,l) | | 25 (d,l) | 45 (d,l) | | 35 (d,l) |
| pyruvate | | | | | | | | |
| Lact/pyr | | oo | oo | | oo | oo | | oo |
| D B OHbutyrate | | | | | | | | |
| acetoacetate | | | | | | | | |
| B HB/acac | | | | | | | | |
| acetate | | | | 28 | | | 44.5 | |
| Other | | | | | | | | |
| ΣmEq anions | 128.7–139.4 | 137 | 69 | 137 | 87 | 146 | 147 | 141 |
| Na/Cl | 1.28–1.45 | 1.19 | 1.18 | 1.19 | 1.16 | 1.40 | 1.38 | 1.25 |
| Glucose or others | 3.9–5.6 | 278 | 139 | 278 | 278 | 83 | 236 | 236 |
| $CO_2$ | 0.99–1.39 | | | | | | | |
| pH | 7.35 | | | | | ~5.5–6.5 | ~5.5–6.5 | ~5.5–6.5 |
| ΣmOsm | 285–295 | 524? *(550.5) | 263 | 523 | 443 | 366 | 510 | 494 |
| Use: | | I.V. therapy for dehydration | I.V. therapy same as 2 c 1 | I.V. therapy same as 2 c 1 | Parenteral nutrition | Peritoneal dialysis | Peritoneal dialysis | Peritoneal dialysis |

*2 c 1. Facts and Comparisons Oct '81, p 52. The osmolarity listed by the reference appears to be incorrect at 524 mOsm. The correct osmolarity appears to be 550.5 mOsm.
2 c 2–2 c 3. Facts and Comparisons Oct '81, p52. Lippincott, St Louis
2 c 4. Facts and Comparisons Oct '81, p52. Lippincott, St Louis
2 c 5–2 c 7. Facts and Comparisons Oct '82, p704, Lippincott, St Louis

| Units mmoles L fluid | Normal Plasma N.E.J.M. 283, 1285 1970 | 37 2 c 8 L/P, BHB/Acac Ringer's & 5% Gluc | 38 2 c 9 Na/Cl, L/P Balanced Ringer's & 5% Gluc |
|---|---|---|---|
| Na | 136–145 | 130 | 130 |
| K | 3.5–5.0 | 4 | 4 |
| Ca | 2.1–2.6 | 1.5 | 1.5 |
| free [Ca2+] | [1.06] | | |
| Mg | 0.75–1.25 | | |
| free [Mg2+] | [0.53] | | |
| ΣmEq Cations | 142.7–153.2 | 137 | 137 |
| Cl | 100–106 | 104 | 96 |
| $HCO_3$ | 26–28 | | |
| ΣPi | 1–1.45 | | |

TABLE X-continued

| | | | | | | |
|---|---|---|---|---|---|---|
| SO$_4$ | 0.32-0.94 | | | | | |
| L-lactate | 0.6-1.8 | 24.5 | 35.9 | | | |
| pyruvate | | 3.5 | 5.1 | | | |
| Lact/pyr | | 7 | 7 | | | |
| D B OHbutyrate | | 3 | | | | |
| acetoacetate | | 2 | | | | |
| B HB/acac | | 1.5 | | | | |
| acetate | | | | | | |
| Other | | | | | | |
| ΣmEq anions | 128.7-139.4 | 137 | 137 | | | |
| Na/Cl | 1.28-1.45 | 1.24 | 1.35 | | | |
| Glucose or others | 3.9-5.6 | 278 | 278 | | | |
| CO$_2$ | 0.99-1.39 | | | | | |
| pH | 7.35-7.45 | | | | | |
| ΣmOsm | 285-295 | 550.5 | 550.5 | | | |
| Use: | | Improved 2 c 1, with redox balance and normal Na/Cl | 2 a 6 with Gluc. Normal BHB/Acac normal Na/Cl ratio | | | |

Class 2d Electrolyte Fluids for Contacting Living Cells Containing 3 to 4 Cations plus Non-Ionic Nutrients plus HCO$_3^-$/CO$_2$.

| Units mmoles L fluid | Normal Plasma N.E.J.M. 283, 1285 1970 | 2 d 1 Krebs Serum Substitute | 2 d 2 Tyrode's Solution | 39 2 d 3 Veech's Redox Balanced Salt Solution | 40 2 d 4 Veech's R.B.-Salt sine Pi cum 5% Glucose | 41 2 d 5 Veech's R.B.-Salt sine Pi |
|---|---|---|---|---|---|---|
| Na | 136-145 | 141 | 151.54 | 142 | 140.4 | 141 |
| K | 3.5-5.0 | 5.93 | 5.9 | 4.5 | 4.5 | 4 |
| Ca | 2.1-2.6 | 2.54 | 1.8 | 1.1 | 1.1 | 1.1 |
| free [Ca2+] | [1.06] | | | [1.06] | | |
| Mg | 0.75-1.25 | 1.18 | 0.45 | 0.56 | 0.56 | 0.56 |
| free [Mg2+] | [0.53] | | | [0.53] | | |
| ΣmEq Cations | 142.7-153.2 | 154.37 | 162.07 | 149.82 | 148.2 | 148.3 |
| Cl | 100-106 | 104.8 | 147.8 | 102 | 102 | 102 |
| HCO$_3$ | 26-28 | 24.9 | 11.9 | 29 | 29 | 29 |
| ΣPi | 1-1.45 | 1.23 | 1.22# | 1.1* | | |
| SO$_4$ | 0.32-0.94 | 2.36 | | [0.7] | | |
| L-lactate | 0.6-1.8 | | 1.33 | 10.7 | 10.7 | 10.8 |
| pyruvate | | 4.9 | 0.09 | 1.5 | 1.5 | 1.5 |
| Lact/pyr | | | 14.8 | 7 | 7 | 7 |
| D B OHbutyrate | | | | 3 | 3 | 3 |
| acetoacetate | | | | 2 | 2 | 2 |
| B HB/acac | | | | 1.5 | 1.5 | 1.5 |
| acetate | | | | | | |
| Other | | 2.45 glutamate$^-$ 5.4 fumerate$^{2-}$ | | | | |
| ΣmEq anions | 128.7-139.4 | 154.47 | 162.81 | 149.82 | 148.2 | 148.3 |
| Na/Cl | 1.28-1.45 | 1.35 | 1.03 | 1.39 | 1.38 | 1.38 |
| Glucose or others | 3.9-5.6 | 9.2 | 5.45 | 10 | 277 | 10 |
| CO$_2$ | 0.99-1.39 | 1.0 | 1.17 | 1.45 | 1.45 | 1.45 |
| pH | 7.35-7.45 | 7.4 | 7.1 | 7.40 | 7.40 | 7.40 |
| ΣmOsm | 285-295 | 308.2 | 328 | 308.6 | 573.2 | 306.4 |

TABLE X-continued

| Use: | Media tissue slices | For liver perfusion | For I.V. or general use to replace 2 b 1 & 2 d 1 | for peritoneal dial. or I.V. | for I.V. & peritoneal dialysis |
|---|---|---|---|---|---|

2 d 1. Krebs H A. Bichem Biophys Acta 4: 249–269, 1950
2 d 2. Tyrode M. J. Arch int Pharmacodyn 20: 205, 1910. #For use in liver perfusion with albumin see Schimassek H. Biochem Z 336: 460, 1963
2 d 3. *The apparent charge on sum Pi in the presence of these cations is about 1.46 not 1.8 presumably due to cation binding.

TABLE XI

Prior Art Hemodialysis Fluids. For recent discussion see Parsons FM, Stewart WK. Composition of Dialysis Fluid. In: Replacement of Renal Function by Dialysis (Drucker W, Parsons Fm, Maher JP, eds.) Martinus Nijhoff, Hingham, pp 148–170, 1983.

| Units mmoles L fluid | Normal Plasma N.E.J.M. 283, 1285 1970 | 2 d 6 Kolff 1947 | 2 d 7 Brigham 1952 | 2 a 16 Scribner's Acetate 1964 | 2 a 17 Commercial Acetate 1981 | 2 a 18 Bjaelder "Low" Acet. 1981 | 2 a 19 Kraut "High" Acet. 1981 | 2 b 2 COBE $HCO_3$—Acetic Acid, 1981 | 2 b 3 $HCO_3$—Acetic Acid |
|---|---|---|---|---|---|---|---|---|---|
| Na | 136–145 | 126 | 140 | 135 | 140 | 134 | 136 | 140 | 135 |
| K | 3.5–5.0 | 5.6 | 4 | 1.5 | 2 | 2.2 | 2.2 | 2 | 2 |
| Ca | 2.1–2.6 | 1.0 | 1.25 | 1.25 | 0.875 | 1.84 | 1.91 | 1.75 | 1.5 |
| free [Ca2+] | [1.06] | | | | | | | | |
| Mg | 0.75–1.25 | | 0.5 | 0.5 | 0.375 | 0 | 0 | — | 0.375 |
| free [Mg2+] | [0.53] | | | | | | | | |
| mEq Cations | 142.7–153.2 | 133.6 | 147.5 | 140 | 144.5 | 139.88 | 142.02 | 145.5 | 140.75 |
| Cl | 100–106 | 109 | 120.7 | 105 | 106 | 107.28 | 103.82 | 107 | 106.5 |
| $HCO_3$ | 26–28 | 23.9 | 26.8 | | | | | 33 | 33 |
| Pi | 1–1.45 | | | | | | | | |
| $SO_4$ | 0.32–0.94 | | | | | | | | |
| L-lactate | 0.6–1.8 | | | | | | | | |
| pyruvate | | | | | | | | | |
| Lact/pyr | | | | | | | | | |
| D B | | | | | | | | | |
| OHbutyrate | | | | | | | | | |
| acetoacetate | | | | | | | | | |
| B HB/ acac | | | | | | | | | |
| acetate | | | | | 35 | 38.5 | 32.6 | 38.2 | |
| Other | | | | | | | | 2 HAcetate 23.5 gluconate | 2 HAcetate |
| mEq anions | 128.7–139.4 | 132.9 | 147.5 | 140 | 144.5 | 139.88 | 142.02 | 145.5 | 141.5 |
| Na/Cl | 1.28–1.45 | 1.16 | 1.16 | 1.29 | 1.32 | 1.25 | 1.31 | 1.31 | 1.27 |
| Glucose or others | 3.9–5.6 | 76–151 | 10 | 0 | 0 | 0 | 0 | 0 | 0 |
| $CO_2$ | 0.99–1.39 | 0 | 1.24 | 0 | 0 | 0 | 0 | ~1.3 | ~1.3 |
| pH | 7.35–7.45 | ~8.6 | 7.4 | ~5.5–6.5 | ~5.5–6.5 | ~6.7 | ~6.7 | ~7.4 | ~7.4 |
| mOsm | 285–295 | 343–418 | 304.8 | 278.25 | 287.75 | 277.92 | 282.97 | 289.3 | 280.4 |

2 d 6. Kolff Wj. New Ways of Treating Uremia, J & A Chruchill, London, 1947
2 d 7. Murphy WP, Swan RC, Walter C, Weller JM, Merrill JP. J Lab Clin Med 40: 436, 1952. Essentially Krebs Henseleit, but with lower Mg and Ca.
2 a 16. Mion CM, Hegstrom RM, Boen ST, Scribner BH. Trans Am Soc Artif intern Organs 10: 110–113, 1964
2 a 17. Made in concentrates by numerous manufactures. The mean concentrations used are given in 2 d 17 according to Parsons FM and Stewart WK, listed above in title.
2 a 18. Bjaelder et al Nepbron 27: 142–145, 1981. "Low " acetate leaves the patients acidotic, "high" acetate leaves them in normal. Bjaelder's interpretation for the reasons for the acidosis are incorrect.
2 b 6. Kraut J et al. Clin Neph 15: 181, 1981. Used $HCO_3$ and acetic acid.
2 b 3. Commercial source. CDBE Laboratories, 1201 Oak Street, Lakewood Colorado.

TABLE III

Prior Art Peritoneal Dialysis Solutions
The compilation of solutions are taken from: Facts and Comparison J.B. Lippincott, 111 West Port Plaza, Suite 423, St Louis, Mo. 63146, October, 1982, p. 705–706.
Indication: Acute renal failure or exacerbation of chronic renal failure; acute poisoning by dialyzable toxins; acute pulmonary edema; intractable peripheral edema; anasarca; endogenous intoxication such as hyperkalemia, hyperuricemia, hypercalcemia, and uremia; hepatic coma, especially with hepatorenal syndrome.

| Product and Distributor | Dextrose g/Liter | $Na^+$ | $K^+$ | $Ca^{++}$ | $Mg^{++}$ | $Cl^-$ | Lactate | Acetate | mOsm/ Liter | Osmolarity How Supplied |
|---|---|---|---|---|---|---|---|---|---|---|
| Dianeal w/1.5% Dextrose(Travenol) | 15 | 141 | | 3.5 | 1.5 | 101 | 45 | | 366 | In 1000 and 2000 ml. |
| Dianeal PD-2 w/1.5% Dextrose (Travenol) | 15 | 132 | | 3.5 | 0.5 | 96 | 40 | | 346 | In 2000 ml. |
| Dianeal 137 w/1.5% Dextrose (Travenol) | 15 | 132 | | 3.5 | 1.5 | 102 | 35 | | 347 | In 2000 ml. |
| Inpersol w/1.5% Dextrose (Abbott) | 15 | 132 | | 3.5 | 1.5 | 99 | 35 | | 344 | In 1000 and 2000 ml. |
| Peridial 1 1/2-D (Cutter) | 15 | 133 | | 3.5 | 1.5 | 102 | 35 | | 348 | In 1000 and 2000 ml. |
| Peritoneal Dialysis w/1.5% Dextrose-Low Sodium (American-McGaw) | 15 | 131 | | 3.4 | 1.5 | 100 | 35 | | 345 | In 1000 and 2000 ml. |
| Dianeal K w/1.5% Dextrose | 15 | 141 | 4 | 3.5 | 1.5 | 105 | 45 | | 374 | In 1000 ml. |

TABLE III-continued

Prior Art Peritoneal Dialysis Solutions

The compilation of solutions are taken from: Facts and Comparison J.B. Lippincott, 111 West Port Plaza, Suite 423, St Louis, Mo. 63146, October, 1982, p. 705-706.

Indication: Acute renal failure or exacerbation of chronic renal failure; acute poisoning by dialyzable toxins; acute pulmonary edema; intractable peripheral edema; anasarca; endogenous intoxication such as hyperkalemia, hyperuricemia, hypercalcemia, and uremia; hepatic coma, especially with hepatorenal syndrome.

| Product and Distributor | Dextrose g/Liter | $Na^+$ | $K^+$ | $Ca^{++}$ | $Mg^{++}$ | $Cl^-$ | Lactate | Acetate | mOsm/ Liter | How Supplied |
|---|---|---|---|---|---|---|---|---|---|---|
| Dianeal K-141 w/1.5% Dextrose (Travenol) | 15 | 132 | 4 | 3.5 | 1.5 | 106 | 35 | | 355 | In 2000 ml. |
| Peritoneal Dialysis w/1.5% Dextrose-Potassium (American McGaw) | 15 | 140 | 4 | 4.0 | 1.5 | 105 | | 45 | 375 | In 2000 ml. |
| Peritoneal Dialysis w/1.5% Dextrose (American McGaw) | 15 | 141 | | 4.0 | 1.5 | 103 | | 45 | 370 | In 1000 and 2000 ml. |
| Dianeal PD-2 w/2.5% Dextrose (Travenol) | 25 | 132 | | 3.5 | 0.5 | 96 | 40 | | 396 | In 2000 ml. |
| Dianeal PD-2 w/4.25% Dextrose (Travenol) | 42.5 | 132 | | 3.5 | 0.5 | 96 | 40 | | 485 | In 2000 ml. |
| Dianeal w/4.25% Dextrose (Travenol) | 42.5 | 141 | | 3.5 | 1.5 | 101 | 45 | | 505 | In 2000 ml. |
| Dianeal 137 w/4.25% Dextrose (Travenol) | 42.5 | 132 | | 3.5 | 1.5 | 102 | 35 | | 486 | In 2000 ml. |
| Inpersol w/4.25% Dextrose (Abbott) | 42.5 | 132 | | 3.5 | 1.5 | 99 | 35 | | 484 | In 2000 ml. |
| Peridial 4 1/2-D (Cutter) | 42.5 | 133 | | 3.5 | 1.5 | 102 | 35 | | 487 | In 2000 ml. |
| Peritoneal Dialysis w/4.25% Dextrose-Low Sodium (American McGaw) | 42.5 | 131.5 | | 3.4 | 1.5 | 100 | 35 | | 485 | In 2000 ml. |
| Dianeal K-141 w/4.25% Dextrose (Travenol) | 42.5 | 132 | 4 | 3.4 | 1.5 | 106 | 35 | | 494 | In 2000 ml. |
| Peritoneal Dialysis w/4.25% Dextrose | 42.5 | 141.5 | | 4.0 | 1.5 | 103 | | 45 | 510 | In 2000 ml. |
| Peritoneal Dialysis Concentrate w/30% D* (American McGaw) | 15 | 130 | | 3.5 | 1.0 | 102 | | 34.5 | 345 | In 2000 ml. |
| Peritoneal Dialysis Concentrate w/50% D* (American McGaw) | 25 | 130 | | 3.5 | 1.0 | 102 | | 34.5 | 395 | In 2000 ml. |
| Peritoneal Dialysis Concentrate w/30% D* Low Sodium (American McGaw) | 15 | 118.5 | | 3.5 | 1.0 | 90.5 | | 34 | 320 | In 2000 ml. |
| Peritoneal Dialysis Concentrate w/50% D* | 25 | 118.5 | | 3.5 | 1.0 | 90.5 | | 34 | 370 | In 2000 ml. |

*Concentration of formulation after dilution with 10 parts water.

EXAMPLE 42

The following example illustrates usage of Class I solutions for electrolyte and fluid therapy.

The most commonly used electrolyte solution used today, by those skilled in the art, is so called "physiological" salt, or "normal saline" by which is means 0.9% NaCl in $H_2O$ in the U.S. or 0.95% NaCl in $H_2O$ in the United Kingdom. (See Table IX solutions 1a1 and 1a2 respectively). These solutions, wherein the milliequivalent ratio of Na/Cl is 1, are distinctly different from normal human plasma wherein the ratio of Na/Cl ranges from 1.28 to 1.45 (*N.E.J.M.* 283, 1285, 1970). Infusion of such solutions has long been recognized to be undesirable leading to a pathological condition known as "hyperchloremic acidosis". (See Black D. A. K., *Lancet* 1, 353, 1953, and *Harrison's Textbook of Medicine*, pp 230 to 236, 1983). The degree of the pathology induced by solutions where the ratio of Na/Cl is below the ratio 1.28-1.45 depends upon:

(1) the quantity of solution infused relative to the volume and electrolyte content of the extra- and intracellular $H_2O$ volume of the cells being contacted;

(2) the rate of infusion of solutions;

(3) the degree of existing pathology in the organism being contacted with such fluid;

(4) the efficiency of the kidney in excreting the excess of $Cl^-$ over $Na^+$ being administered.

In this example, the replacement of plasma $H_2O$ and salt content in the rat serves as a model stimulating the situation which might occur in a human patient when a severe burn over 50% of the body exists resulting in the loss of plasma $H_2O$ and electrolytes into transudates and blisters over the surface of damaged skin. Three solutions for therapy will be used: standard 0.9% aqueous NaCl (composition 1a1 of Table IX), standard lactated Ringer's U.S. (composition 2a3 of Table X) and a modified redox-balanced Ringer's Lactate solution containing, with near-equilibrium couples, (1-lactate$^-$/pyruvate$^-$ and D-betahydroxybutyrate$^-$/acetoacetate$^-$), $HCO_3^-/CO_2$ (composition 2b2 of Table X) in accord with the present invention. The composition of the 3 fluids are given in Table XIII below.

TABLE XIII

| | Composition of Fluids | | | (Electro2) |
|---|---|---|---|---|
| Units mmoles — L fluid | Normal Plasma N.E.J.M. 283, 1285 1970 | 1 a 1 Isotonic NaCl | 2 a 3 Lactated Ringer's | 2 b 2 R—B Lactated Ringer's $HCO_3^-/CO_2$ |
| Na | 136–145 | 155 | 130 | 130 |
| K | 3.5–5.0 | | 4 | 4 |
| Ca | 2.1–2.6 | | 1.5 | 1.5 |
| free [Ca2+] | [1.06] | | | |
| Mg | 0.75–1.25 | | | |
| free [Mg2+] | [0.53] | | | |
| Σ mEq Cations | 142.7–153.2 | 155 | 137 | 137 |
| Cl | 100–106 | 155 | 109 | 96 |
| $HCO_3$ | 26–28 | | | 29 |
| Σ Pi | 1–1.45 | | | |
| $SO_4$ | 0.32–0.94 | | | |
| L-lactate | 0.6–1.8 | | 28 (d,l) | 7 |
| pyruvate | | | | 1 |
| Lact/pyr | | | oo | 7 |
| D B OHbutyrate | | | | 3 |
| acetoacetate | | | | 1 |
| B HB/acac | | | | 3 |
| acetate | | | | |
| Other | | | | |
| Σ mEq anions | 128.7–139.4 | 155 | 137 | 137 |
| Na/Cl | 1.28–1.45 | 1.00 | 1.19 | 1.35 |
| Glucose or others | 3.9–5.6 | | | |
| $CO_2$ | 0.99–1.39 | | | 1.5 |
| pH | 7.35–7.45 | 6.0 | 6.5 | 7.4 |
| Σ mOsm | 285–295 | 310 | 272 | 274 |

METHODS 250 fed male Wistar rats are each anesthetized and systematically burned with gasoline over approximately the lower 50% of the body surface. A blood sample is taken from each rat prior to administration of the burn, and then again two hours after the burn from a venous canula inserted into the saphenous vein. Each animal is placed in a restraining cage.

In the opposite saphenous vein, a canula is inserted to measure plasma electrolyte content. Five minutes after administration of each electrolyte solution, blood is drawn for electrolyte analysis. Each rat's liver is removed, freeze clamped and the redox and phosphorylation states of liver measured by the methods previously described by Veech et al. (J. Biol. Chem. 254, 6538–6547, 1979).

RESULTS AND DISCUSSION

It is observed that ½ hour after the gasoline burn, a series of weeping blisters develop over the lower ½ of each rat's body. The volume of the transudate within these blisters is estimated by measurement of area and thickness to contain 4 ml of transudate or (250×0.07=17.5 ml blood volume) or about 40% of the rat's average total plasma volume. This deduction is confirmed by measurement of the rat hematocrit which is 55% while the Na+ is 155 millimoles per liter plasma and Cl− is 110 millimoles per liter plasma due to fluid loss. In the untreated controls rats, the hematocrit is 44%. Each treated animal's blood pressure is falling, heart rate is increasing, and urine output ceases.

Each treated animal is judged to be in hypo-volemic shock and 6 mls of the three different solutions are infused, by venous canula, over the next 10 minutes, into three different animals. Five minutes after completion of the infusion, electrolytes are drawn from the canula, the animals sacrificed, and the liver freeze clamped. The average blood electrolyte level, in each of the three groups of animals so infused, is shown in Table XIV below.

TABLE XIV

| | Composition of Plasma After Infusion | | | (Electro2) |
|---|---|---|---|---|
| Units mmoles/ L fluid | Normal Pasma N.E.J.M. 283, 1285, 1970 | 1 a 1 Isotonic NaCl | 2 a 3 Lactated Ringers | 2 b 2 R—B Lactated Ringers $HCO_3^-/CO_2$ |
| Na | 135–145 | 150 | 143 | 138 |
| K | 3.5–5.0 | 5 | 5 | 5 |
| Ca | 2.1–2.6 | 2.0 | 2.2 | 2.5 |
| free [$Ca^{2+}$] | [1.06] | | | |
| Mg | 0.75–1.25 | 1.0 | 1.0 | 1.0 |
| free [$Mg^{2+}$] | [0.53] | | | |

TABLE XIV-continued

| Composition of Plasma After Infusion | | | | (Electro2) |
|---|---|---|---|---|
| Σ meq Cations | 142.7–153.2 | 158 | 153.2 | 147.5 |
| Cl | 100–106 | 123 | 105 | 102 |
| HCO$_3$ | 26–28 | 18 | 13 | 27 |
| Σ Pi | 1–1.45 | 1.5 | 1.2 | 1 |
| L-lactate | 0.6–1.8 | 5.0 | 21 | 5 |
| pyruvate | | 0.3 | 1.0 | 0.7 |
| Lact/pyr | | | 21 | 7 |
| D-B—OH butyrate | | | | 2 |
| acetoacetate | | | | 0.7 |
| BHB/acac | | | | 3 |
| acetate | | | | |
| others | | | | |
| Σ meq anions | 128.7–139.4 | 146.3 | 141.2 | 138.65 |
| Na/Cl | 1.28–1.45 | 1.22 | 1.34 | 1.36 |
| Glucose | 3.9–5.6 | 8.2 | 10 | 7 |
| or others | | | | |
| CO$_2$ | 0.99–1.39 | 1.14 | 0.82 | 1.35 |
| pH | 7.35–7.445 | 7.30 | 7.30 | 7.4 |
| Σ m OsM | 285–295 | | | |

Having now fully described the invention, it will be apparent to one of ordinary skill in the art that many changes and modifications can be made thereto without departing from the spirit or scope of the invention as set forth herein.

It is observed that the animals given 1a1 (0.9% saline) solution each have hyperchloremic acidosis with a Na/Cl ratio of 1.22 and plasma pH of 7.30. The animals given solution 2a3 Ringer's Lactate solution each have lactic acidosis with a plasma pH of 7.3 and an elevated [lactate]/[pyruvate] ratio. Both groups of these animals have low serum [HCO$_3$] and have a compensated metabolic acidosis which requires that they hyperventilate off their CO$_2$. In contrast, the animals given solution 2b2 (Redox-balanced Ringers Lactate with HCO$_3$/-CO$_2$) each have a normal [lactate]/[pyruvate] ratio, a normal [HCO$_3^-$]/[CO$_2$] ratio and a normal plasma pH. More importantly, each of these animals achieves a replacement of H$_2$O and electrolytes as required for continued life, but without inducing an abnormal Na/Cl ratio, an abnormal redox state, or an abnormal phosphorylation potential. No change in respiratory pattern is observed in the grave life-threatening situation. Solution 2b2 is then an improvement over the state of the art.

In Table 3 is given the results of the freeze clamping of the liver to illustrate the effects of these solutions on the nucleotide ratios in liver cells. These results indicate that only in the liver cells of the rats treated with the redox-balanced Ringer's lactate solution (Table X, solution 2b2) of this invention do these ratios approach normal values. Here, it is seen that administration of Na/Cl in 1:1 ratio leads to no change in the cytoplasmic [NAD]/[NADH] but does cause an increase in the cytoplasmic [ATP]/[ADP][Pi]. With no intention to be bound by theory, the elevation of [ATP]/[ADP][Pi] would be expected from equation 7 given in another section. The conventional Ringer's lactate (2a3) gives a profound and pathological decrease in the cytoplasmic [NAD$^+$]/[NAD] to levels associated with alcoholic fatty liver. There is, of course, a predictable falls in the [ATP]/[ADP][Pi], since the redox state of the cytoplasmic NAD-couple is directly and inversely linked to the cytoplasmic [ATP]/[ADP][Pi] ratio as equation 5 shows.

In contrast, the new Redox Balanced Ringer's Lactate solution of the present invention does not change the cytoplasmic [NAD$^+$]/[NADH] from out of the normal range and causes no change in the [ATP]-/[ADP][Pi]. Replacement of needed H$_2$O and electrolytes has been accomplished without inducing acidosis or any other recognized pathologic effects which can be demonstrated by using NaCl in 1:1 ratio or standard Ringer's Lactate in this simulation of a very common clinical situation.

TABLE XV

Example 42
Case 1
Metabolite Contents of Freeze-Clamped
Rat Liver in Rats After Infusion with Normal
Saline, Ringer's Lactate, and Redox Balanced
Ringer's Lactate with HCO$_3^-$/CO$_2$
Values are in μmoles/g wet weight.

| | Normal Rat Solution | 0.9% NaCl Infusion 1.a.1. | Ringer's Lactate 2.a.3. | New R-B Ringer's Lactate with HCO$_3^-$/CO$_2$ 2.b.2 |
|---|---|---|---|---|
| Glucose | 7.3 | 8.0 | 13 | 8 |
| Glucose 6-P | 0.12 | 0.18 | 0.26 | 0.16 |
| Dihydroxy-acetone-P | 0.029 | 0.051 | 0.078 | 0.039 |
| 3-Phospho-glycerate | 0.309 | 0.369 | 0.56 | 0.35 |
| L-Lactate | 0.444 | 0.812 | 14.8 | 5.2 |
| Pyruvate | 0.086 | 0.165 | 0.70 | 0.74 |
| L-Lactate/pyr | 5.16 | 4.92 | 21 | 7.00 |
| 3-PG/DHAP | 10.65 | 7.24 | 7.14 | 8.93 |

TABLE XVI

Example
Case 1
Co-Factor Ratios of Freeze-Clamped
Liver of Rat After Infusions with 0.9% Normal
Saline, Ringer's Lactate, and Redox-Balanced
Ringer's Lactate with HCO$_3^-$/CO$_2$

| | Normal Rat | 0.9% NaCl Infused Rat 1.a.1 | Ringer's Lactate Infused Rat 2.a.3 | R-B Ringer's Lactate with HCO$_3^-$/CO$_2$ 2.b.2 |
|---|---|---|---|---|
| Free Cytoplasmic [NAD$^+$]/[NADH] | 1750 | 1790 | 429 | 1290 |
| Free Cytoplasmic | 14,000 | 20,900* | 5,000* | 12,000 |

TABLE XVI-continued

Example
Case 1
Co-Factor Ratios of Freeze-Clamped
Liver of Rat After Infusions with 0.9% Normal
Saline, Ringer's Lactate, and Redox-Balanced
Ringer's Lactate with $HCO_3^-/CO_2$

|  | Normal Rat | 0.9% NaCl Infused Rat 1.a.1 | Ringer's Lactate Infused Rat 2.a.3 | R-B Ringer's Lactate with $HCO_3^-/CO_2$ 2.b.2 |
|---|---|---|---|---|
| $\frac{[\Sigma ATP]}{[\Sigma ADP][\Sigma Pi]}$ $M^{-1}$ |  |  |  |  |

*indicates change is significant at $p > 0.05$.

EXAMPLE 43

Use of Solutions for Parenteral Nutrition

The procedure used is identical to that utilized by Woods, Eggleston and Krebs in *Biochem. J.* (1970) 119, 501–510.

Animals and Diets

Female Wistar rats, each weighing 170–215 g, are obtained and are fed on a standard small-animal diet.

Reagents

D-Glyceraldehyde, 1-α-Glycerophosphate (dicylohexylammonium salt) having a purity of 96% of the calculate L-form and other substances, nucleotides, coenzymes, and crystalline enzymes.

Liver Perfusion

The method of liver perfusion used is that described by Hems, Ross, Berry & Krebs (1966). The perfusion medium is the physiological saline (Krebs & Henseleit, 1932), containing washed aged human erythrocytes. The bovine serum albumin is dialyzed as a 10% solution (at 4° C.) against three changes of physiological saline (Krebs-Henseleit) and gassed with $CO_2+O_2$ (5:95).

The perfusion medium described by Hems et al. (1966) is used, which contains initially about 1 mM l-lactate [0.87±0.05 S.E.M. (14) umol/ml] derived from the erythrocytes. To decrease the initial lactate concentration, the erythrocytes are washed five times with ten times their volume of physiological saline. This lowers the initial lactate concentration in the perfusion medium to 0.23±0.02 S.E.M. (16) umol/ml. The medium is gassed with $CO_2+O_2$ (5:95) during perfusion.

Into the perfusion of 150 ml is added a sufficient quantity of two parenteral nutrient solutions, one containing 10 mM D-Fructose from a commercial source (5% Fructose in Electrolyte #75, Travenol, *Facts and Comparison*, August '83, p52b) and a new parenteral solution composition using glucose in place of fructose, a normal Na:Cl ratio, redox-balanced lactate/pyruvate and excess K as does Electrolyte #75. Glucose enters the metabolic sequence at a "safe entry" point as herein defined. The composition of each solution is given in Table XVII below.

Sampling of Liver

For the analysis of liver, samples are rapidly frozen in vivo or during perfusion, by using the deep cooled clamps of Wollenberger, Ristau & Schoffa (1960). The resulting disc of liver tissue is ground to a fine powder in a cooled mortar with frequent additions of liquid $N_2$. The liver powder is transferred to a tared centrifuge tube cooled in liquid $N_2$ and 4 ml of icecold 6% (w/v) $HClO_4$ is then added to each gram of liver powder with constant stirring. The resulting slurry is allowed to thaw and then is homogenized in the centrifuge tube at a low speed with a glass pestle. The homogenate is kept ice-cold for 30 minutes, centrifuged, and the resulting supernatant is brought to pH 6–7 with 20% (w/v) KOH to precipitate the excess of $HClO_4$ as $KClO_4$. The assays are carried out on the clear supernatant.

Preparation of Liver Aldolase

Livers of large (300–450 g) rats are bled by perfusion in situ with cold isoosmotic KCl and then homogenized with 4 vol. of KCl. After centrifugation at 30000×g for 20 minutes, the supernatant is fractionated with $(NH_4)_2SO_4$ as described by Leuthardt & Wolfe (1955). The final precipitate is taken up in a small volume of water (0.3 ml/g of original liver) and dialyzed against 200 vol. of water at 0 C., changed every hour for 4 h. The cloudy preparation is centrifuged and 0.1 ml of 0.1M EDTA is added to every 4 ml of clear supernatant.

TABLE XVII

| UNITS | COMPOSITION OF FLUIDS | | |
|---|---|---|---|
|  | (1) | (2) | (3) |
| m moles/L |  |  |  |
| Na | 136–145 | 40 | 40 |
| K | 3.5–5.0 | 35 | 35 |
| Ca | 2.1–2.6 |  |  |
| free [$Ca^{2+}$] | [1.06] |  |  |
| Mg | 0.75–1.25 |  |  |
| free [$Mg^{2+}$] | [0.53] |  |  |
| meq Cations | 142.7–153.2 | 75 | 75 |
| Cl | 100–106 | 47.5 | 29 |
| $HCO_3$ | 26–28 |  | 26 |
| Pi | 1–1.45 | 7.5 | 1.4 |
| $SO_4$ | 0.32–0.94 |  |  |
| l-lactate | 0.6–1.8 | 20(d,l) | 15.64 |
| pyruvate |  |  | 1.56 |
| Lact/pyr |  | (inf.) | 10 |
| d-Beta OH butyrate |  |  |  |
| Acetoacetate |  |  |  |
| Beta HB/acac |  |  |  |
| Acetate |  |  |  |
| Others |  |  |  |
| meq anions | 128.7–139.4 | 75 | 75 |
| Na/Cl | 1.28–1.45 | 0.84 | 1.36 |
| Glucose | 3.9–5.6 |  | 278 |
| Fructose |  | 278 |  |
| $CO_2$ | 0.99–1.39 |  | 1.5 |
| pH | 7.35–7.45 | — | 7.4 |
| m OsM | 285–295 | 428 | 429.5 |

Footnotes for Table 1
(1) Indicates: Normal Human Plasma as reported in N.E.J.M. 283, 1285, (1970).
(2) Indicates: 5 wt % Fructose in Electrolyte #75 (commercially available from Travenol as shown in "Facts & Comparisons" Aug. '83, p. 52b).
(3) Indicates 5% Glucose in Electrolyte Solution for parenteral nutrition from this patent following our outlines of safe entry points and a normalized Na/Cl ratio and redox state. Such a solution improves Solution 2 in this table.

Incubation for 1 h at 25° C. completely inactivated sorbitol dehydrogenase (EC 1.1.1.14) (Hers, 1956), which would otherwise react with fructose. The final preparation, containing 35–45 mg of protein/ml, is stored at −18° C. and is found to lose only about 30% activity in one year. In addition to aldolase activity, it also contains glycerol 1-phosphate dehydrogenase (EC 1.1.1.8) activity and triose phosphate isomerase (EC 5.3.1.1) activity.

Other Aldose Preparations

Chilled fresh rat and rabbit tissues are homogenized with 14 vol. of 1 mM-EDTA and centrifuged for 20 minutes at 30,000×g. The supernatant obtained is used in assays without further purification. A crystalline preparation of rabbit muscle aldolase is supplied by the Boehringer Corp. (London) Ltd.

Analytical Methods

ATP is determined by the method described by Lamprecht & Trautschold (1963), ADP and AMP are determined in the combined assay of Adam (1963). Pi was determined by the method described by Berenblum & Chain (1938) as modified by Martin & Doty (1949). Fructose 1-phosphate, is determined by the method of Eggleston (1970). Fructose 1,6 -diphosphate, is measured together with total triose phosphates in the combined assay of Bucher & Hohorst (1963); pyruvate, phosphoenolpyruvate, 2- and 3-phosphoglycerate are determined in sequence (Czok & Eckert, 1963). The references to other analytical methods are as follows: α-glycerophosphate (Hohorst, 1963b); L-(+)-lactate (Hohorst, 1963c); glucose 6-phosphate and fructose 6-phosphate (Hohorst, 1963c); glucose 1-phosphate (Bergmeyer & Klotzsch, 1963); glucose and fructose (Klotzmeyer & Bergmeyer, 1963); the sum of D-glyceraldehyde and glycerol (Pinter, Hayashi & Watson, 1967). For the fluorimetric determination of very low concentrations of glyceraldehyde 3-phosphate and dihydroxyacetone phosphate by the method of Veech, Raijman, Dalziel & Krebs (1969), a portion of the neutralized supernatant is shaken for 1 minute with Florisil (100–200 U.S. mesh) to remove flavins and then recentrifuged before use. In livers perfused with fructose where the concentration of dihydroxyacetone phosphate is increased, it is determined by the spectrophotometric method of Bucher & Hohorst (1963). IMP is determined by a combination of paper chromatographic separation (Krebs & Hems, 1953) and a spectrophotometric assay. A portion of deproteinized liver extract (0.1 or 0.2 ml) is dried onto a 1 cm area on Whatman no. 1 chromatograph paper under a current of hot air. Duplicates, with and without added IMP standards (10 ul, 2 mM solutions) on the same spot, are developed by descending chromatography with the isobutyric acid-ammonia solvent mixture described by Krebs & Hems (1953) for 45–48 h at room temperature. After drying in a current of air, the papers are examined under u.v. light from a Chromatolite lamp (Hanovia Ltd., Slough, Bucks, U.K.) and absorbent areas are ringed by pencil. Average distances run from the starting line are: IMP 23 cm, ATP 27 cm, ADP 32 cm, AMP and inosine 37 cm. IMP areas, and a blank area of similar size before the starting line, are cut out and dropped into 4 ml of 10 mM potassium phosphate buffer, pH 7.0. After gentle mixing at intervals for 1 h, 3 ml is removed and the extinction at 248 nm in 1 cm wide silica cells in a Zeiss spectrophotometer is determined. At this wavelength, the Emax.×$10^3$ for IMP is 12.3 (Deutsch, 1952). Recovery of standards by the whose procedure is 93–104%.

RESULTS

The values of metabolites found in freeze clamped liver are given in Table XVIII.

TABLE XVIII

Liver Contents of Metabolites (After 10 Minutes of Perfusion) Values Are In uMoles/g Wet Weight

|  | (1) | (2) | (3) |
|---|---|---|---|
| D-Glucose | 6.99 | 2.29 | 10 |
| D-Fructose | about 0 | 10 | about 0 |

TABLE XVIII-continued

Liver Contents of Metabolites (After 10 Minutes of Perfusion) Values Are In uMoles/g Wet Weight

|  | (1) | (2) | (3) |
|---|---|---|---|
| Glucose 6-P | 0.25 | 0.14 | 0.30 |
| Fructose 1-P | 0.23 | 8.72 | 0.25 |
| Dihydroxyacetone -P | 0.04 | 0.16 | 0.04 |
| 3 Phosphoglycerate | 0.26 | 0.16 | 0.26 |
| Lactate | 0.79 | 1.34 | 0.79 |
| Pyruvate | 0.08 | 0.15 | 0.08 |

Footnotes for Table XVIII
(1) Indicates liver before perfusion.
(2) Indicates perfusion with solution 1 from commercial sources.
(3) Indicates perfusion with solution 2 from this patient.

Infusion of a fructose solution at a rate sufficient to raise the blood fructose level to 1 mM drops liver and hence blood glucose level to 2.29 mM and raises fructose 1, P, over 35 fold to 8.7 umoles/g. In contrast, using a glucose solution so as to raise the blood level to 10 mM glucose has no appreciable effects except for a small elevation of glucose 6-P.

In Table XIX, we see that raising blood fructose causes a three fold drop in ATP and a seven fold increase in IMP. The phosphate is simply stripped off the nucleotides to put on fructose 1-P. In addition, the inorganic Pi in liver drops from 4.2. to 1.7 umoles/g weight. Taken together, this is a picture of profound metabolic disorder in intracellular energy metabolism which may be avoided by using the alternative NaCl balanced, redox-balanced solution which uses nutrients of the "safe entry point class".

TABLE XIX

Liver Content of Nucleotides and Pi Values are in umoles/g wet weight

|  | Control | Fructose Solution (1) | Glucose Solution (2) |
|---|---|---|---|
| ATP | 2.22 | 0.51 | 2.22 |
| ADP | 0.78 | 0.66 | 0.78 |
| AMP | 0.26 | 0.20 | 0.26 |
| IMP | 0.165 | 1.14 | 0.165 |
| Pi | 4.25 | 1.67 | 4.25 |
| metabolically active Pi | 13.75 | 13.88 | 13.80 |

In Table XX, we see the [NAD+]/[NADH] ratio calculated from the [1-lactate]/[pyruvate] ratio or the [malate]/[oxaloacetate] ratio increases with fructose by two fold. As predicted by the equation of the $K_{G+G}$ reaction, this is accompanied by an incredible elevation of the free [ΣATP]/[ADP] [ΣPi] ratio to 150,000M$^{-1}$, the highest values ever recorded. Whether near-equilibrium is reached in such an abnormal situation is not the point here. Rather, it is clear fructose abnormally decreases not only the total amounts of the adenine nucleotides (Table XIX) but also severely distorts their thermodynamic relationship thereby profoundly disordering the normal metabolic state of liver. In contrast, solution 2 has no effect, firstly because it does not violate the "safe entry point" concept, and also, because it has pH, redox and NaCl balance.

TABLE XX

Example 2:
Using Class 1 Solutions for Parenteral Nutrition

| | Control Liver | Liver Perfused with Parenteral Nutrient (1) | Liver Perfused with Parenteral Nutrient (2) |
|---|---|---|---|
| Free Cytoplasmic $\frac{[NAD^+]}{[NADH]}$ | 912 | 1812 | 912 |
| Free Cytoplasmic* $\frac{[\Sigma ATP]}{[\Sigma ADP][\Sigma Pi]} M^{-1}$ | 11,517 | 151,000 | 11,517 |

*The free cytoplasmic $\frac{[\Sigma ATP]}{[\Sigma ADP][\Sigma Pi]}$ is calculated from equation 5 in this disclosure as described by Veech R. L. et al, J. Biol. Chem. 254, 6538-6547, 1979.

The example also illustrates the concept of "safe entry points" discussed herein: Compounds which may be included in solutions which directly contact living cells, without, for instance, first passing through the gut wall to be metabolically changed, constitute the group herein herein identified by having "safe entry points". Members of the "safe entry point group" where levels over 3 mM may be used in fluids directly contacting cells are:

$$\frac{\text{l-Lactate}}{\text{pyruvate}}$$

$$\frac{\text{d B-Hydroxybutyrate}}{\text{acetoacetate}}$$

D-Glucose

The upper limits to which even these may be used depends upon the metabolite and medical situation and no upper limit can be set absolutely without such considerations. However, the sum of lactate and pyruvate is generally in the level of 10-12 mM in healthy, jogging adults. The sum of betahydroxybutyrate and acetoacetate is in the range 5-7 mM/L plasma in healthy individuals undergoing reducing three day fasts. (See Cahill G. F. and Aoki T. T. in *Cerebral Metabolism and Neural Function* (1980) Passonneau J. V., Hawkins R. A., Lust W. D. and Welsh F. A. eds; pp 234-242, Williams & Wilkins, Baltimore). Such levels may therefore be considered to be in a "normal" range and used safely in most normal conditions excepting perhaps ketones in pregnant women where the decision by the physician will depend upon the medical necessity. (See Rudolf M. C. J. and Sherwin R. S., *Clinics in Endocr. & Metab.* 12, pp 413-428, 1983).

The toxicity of elevating blood glucose above 13 mM/l is well documented in the studies of the University Diabetes Group and must be balanced in the physician's judgment by the need for calories in the patient. Glucose is herein demonstrated, however, to be much less toxic than fructose.

Compounds which may not be used parenterally as "safe entry points" into the metabolic sequence, as currently practiced in the art, are:
Acetate
Glycerol
Lactate (without pyruvate)
Pyruvate (without lactate)
Fructose The methods used in this example are found in the following reference: Woods HF, Eggleston LV, Krebs HA. The cause of the accumulation of fructose 1-P on fructose loading. *Biochem J* 119: 501-510, 1970.

EXAMPLE 44

Use of Class II Solutions for Peritoneal Dialysis

The procedure used here in similar to that utilized by Klim and Williamson in *Biochem. J.* (1982) 214, 459-464.

Materials

Animals

Male Wistar rats weighing 213+35 g (66), at time of death, are used; there are no significant differences between the mean body weights of the experimental groups. They are maintained on a standard small animal diet, and water ad libitum in an animal house with lights on from 08:00 to 20:00 h. Chronic uremia is induced by the five-sixths bilateral nephrectomy technique (Morrison, 1966). Uremic rats are allowed approximately 14 days to recover from the last operation before use.

Peritoneal-Dialysis Solutions

A commercial peritoneal dialysis solution is used, containing 45 mM acetate and 1.5% glucose (83 mM) and compared to a new dialysis solution of the present invention (Example 3). The composition of the two solutions is comparatively shown in Table XXI. Control rats are simply given glucose to raise their blood levels to those occurring in dialyzed animals.

The methods of measurement of liver metabolites are those of Veech and are described amply in the literature such as Veech et al. *J. Biol. Chem.* 254, 6538-6547, 1979; Veech, Eggleston & Krebs *Biochem. J.* 115, 609-619, 1969 and Veech et al. *FEBS Letts.*, 117, K65-72, 1980.

TABLE XXI

| Units m moles L Fluid | Composition of Dialysis Fluids | | |
|---|---|---|---|
| | Normal Plasma (1) | Commercial Fluid (2) | New Fluid (3) |
| Na | 136-145 | 140 | 140 |
| K | 3.5-5.0 | 4 | 4 |
| Ca | 2.1-2.6 | 2.0 | 2.0 |
| free [$Ca^{2+}$] | [1.06] | | |
| Mg | 0.75-1.25 | 0.75 | 0.75 |
| Sigma mEq. Cations | 142.7-153.2 | 150 | 150 |
| Cl | 100-106 | 105 | 105 |
| $HCO_3$ | 26-28 | | 29 |
| Sigma Pi | 1-1.45 | | |
| $SO_4$ | 0.32-0.94 | | |
| L-lactate | 0.6-1.8 | | 8.21 |
| pyruvate | | | 1.79 |
| Lact/pyr | | | 4.6 |
| D-Beta-OH butyrate | | | 3.24 |
| Acetoacetate | | | 2.76 |
| BetaHB/acac | | | 1.17 |
| Acetate | | 45 | |
| Sigma mEq anions | 128.7-139.4 | 150 | 150 |
| Na/Cl | 1.28-1.45 | 1.33 | 1.33 |
| Glucose | 3.9-5.6 | 83 | 83 |
| $CO_2$ | 0.99-1.39 | | 1.5 |
| pH | 7.35-7.45 | 5.5-6.5 | 7.4 |

TABLE XXI-continued

| Units m moles L Fluid | Composition of Dialysis Fluids | | |
|---|---|---|---|
| | Normal Plasma (1) | Commercial Fluid (2) | New Fluid (3) |
| Sigma m OsM | 285-295 | 379.75 | 379.75 |

Footnotes for Table 1
(1) indicates: Normal plasma N.E.J.M. 283, 1285, 1970.
(2) indicates: Commercial Fluid-Peritoneal dialysis with 1.5% Glucose. American McGaw, Facts and Comparisons, October 1982, page 704.
(3) indicates: New fluid-improved peritoneal dialysis fluid formulated in this disclosure is meant to mimic the ideal commercial fluid. This new fluid is not to be taken as "ideal" but is simply a way of illustrating why acetate should not beused. A better fluid would also contain $HCO_3/CO_2$, Lactate/pyr & Beta-HB-/AcAc but would have an increased Na:Cl ratio of between 1.38 to 1.41 to increase alkali reserve in the chronically acidotic uremics. $Cl^-$ could be 100, $HCO_3^-$ of 34 with $[CO_2]$ of 1.7 mM as an example of a fluid designed in conformity with the principles outlined herein. Such fluids have (1) redox balance and hence normal phosphorylation state achieved with (2) pair of ratioed couplesso as to achieve a normal M desired Na:Cl ratio (3) while causing less pathological consequences than present art allows.

The values of metabolites in rat liver are given after seventy minutes of peritoneal dialysis in Table XXII.

TABLE XXII

| N | Control (13) | (1) Acetate Peritoneal Dialysis (10) | (2) Redox-Balanced Dialysis Fluid (10) |
|---|---|---|---|
| | Values are given in n moles/g wet weight liver. | | |
| Dihydroxy-acetone P | 46 ±3 | 53 ±5 | 69 |
| 3-Phospho-glycerate | 294 ±15 | 405 ±27 | 294 |
| l-Lactate | 727 ±36 | 743 ±70 | 6081 |
| Pyruvate | 158 ±13 | 98 ±9 | 1326 |
| d-Beta Hydroxy-butyrate | 117 ±20 | 151 ±12 | 2400 |
| Acetoacetate | 100 ±19 | 117 ±8 | 1380 |
| Acetate | 20 | 33000 | 20 |

In Table XXIII are given the changes in liver content of divalent cations, Pi, PPi and total metabolizable phosphate containing compounds after such treatment:

Na Acetate currently account for about of 80% of hemodialysis in the United States. The increased Pi demonstrated herein during acetate dialysis is "hidden" in liver and flows out (into blood) after dialysis accounting for why such patients remain persistently hyperphosphotemic leading to much current pathology found in chronic dialysis patients.

The data presented in Table XXIII clearly show that peritoneal dialysis, with acetate containing fluids, leads to gross elevations of liver inorganic pyrophosphate and liver calcium. While not widely appreciated, inorganic pyrophosphate (PPi) is an important controller of cellular metabolic pathways of many types. See Lawson J. W. R. et al. in *Gluconeogenesis*, 1976 (Hanson R. W. & Mehlman M. A. Eds) pp 481–511, John Wiley & Sons, New York). Changes in PPi are therefore likely to be of widespread signficance. The 70% increase in liver calcium is, of course, clearly large and of potential significance because of the importance calcium plays as an activator of many intracellular protein kinases.

Finally, Table XXIII shows that acetate induces a rapid increase of 4.2 umoles/g wet weight of the liver's rapidly metabolizing phosphate compounds. It derives this excess $\Sigma Pi$ from the blood and other phosphate stores. When the acetate is finally metabolized, this phosphate returns to the blood where Pi is 1–1.45 mM. Since liver and blood are roughly equal in weight in the normal adult, this movement of $\Sigma Pi$ out of liver must inevitably lead to the hyperphosphatemia which is a major and persistent pathological sequalae of uremia treated by current dialysis practice. This persistent elevation of blood Pi leads to chronic hyperparathyroidism, hypocalcemia, accelerated bone disease, ectopic calcification of tissue and many other causes of morbidity and even mortality in chronic renal disease. Because the phosphate accumulates in the liver during acetate dialysis, it is effectively "hidden" from the beneficial effects which dialysis is trying to obtain, namely the removal of excess dietary $\Sigma Pi$ which is taken in by the patient during the intradialysis periods.

TABLE XXIII

Changes in Mg, Ca, Pi and PPi Content in Rat Liver During Dialysis.
Values in umoles/g wet weight liver.

| | Control (16) | (1) Acetate Dialysis (16) | Change Induced by Acetate Dialysis | (2) New Dialysis | Change Induced by new Dialysis |
|---|---|---|---|---|---|
| Ca | 1.06 | 1.76 | +.70 | 1.06 | 0 |
| Mg | 11.76 | 12.94 | +1.18 | 11.8 | 0 |
| Inorganic Pyrophosphate (PPi) | .018 | 0.198 | +0.18 | 0.018 | 0 |
| Inorganic Phosphate (Pi) | 3.19 | 4.55 | +1.36 | 3.19 | 0 |
| Sigma Adenine Nucleotides | 7.95 | 9.43 | +1.48 | 7.95 | 0 |
| Sigma Guanine Nucleodites | 1.56 | 1.97 | +0.41 | 1.56 | 0 |
| Sigma Glycolytic Pi | 0.65 | 1.65 | +0.06 | 0.85 | +.2 |
| Sigma Metabolic Pi from all measured Metabolites | 13.75 | 17.97 | +4.22 | 13.95 | +.2 |

It should be remembered that normal hemodialysis with 35 mM acetate makes the abnormal elevation in PPi reach 100 times normal with a quadrupling of liver Ca at the expense of bone stores of calcium. It is thus exaggerated in every way. Solutions containing 35 mM

TABLE XXIV

Table XXIV gives the results obtained for the redox and phosphorylation states calculated, as described in Equations 4 and 5. Values are given as means + S.E.M.

| N | Control (5) | (1) Acetate Dialysis (6) | (2) New Dialysis (6) |
|---|---|---|---|
| Cytoplasmic free [NAD+]/[NADH] | 1944 + 94 | 1209* + 88 | about 1944 |
| Mitochondrial free [NAD+]/[NADH] | 18.2 + 2.3 | 17.4 + 2.6 | about 18.2 |
| cytoplasmic [ΣATP]/[ΣADP][ΣPi] $M^{-1}$ | 25,800 + 3,200 | 13,700* + 2,600 | about 25,800 |

*Indicates significant difference at $P > 0.05$.

The use of acetate in a peritoneal dialysis fluid obviously causes a significant decreased in the free cytoplasmic [NAD+]/[NADH] and an even more profound decrease in the cytoplasmic [ΣATP]/[ΣADP][ΣPi] ratio. This is so because the free [NAD+]/[NADH] ratio of cytoplasm is directly linked to the free cytoplasmic [ΣATP]/[ΣADP][ΣPi] by equation 5. (see Veech, et al., *J. Biol. Chem.* 254, 6538–6547, 1979). On page 704 of *Facts and Comparisons*, October, 1982, are listed 16 peritoneal dialysis solutions, using 35 to 45 mMolar (d,l)-lactate in commercial peritoneal dialysis solutions made by four different commercial manufacturers. These solutions, in addition to the 7 commercial acetates containing peritoneal dialysis solutions, make up the current state of the art. None achieve the normal Na/Cl ratio they desire in the manner described herein.

No example of the effects of using 35 to 45 mM L-lactate alone, in a peritoneal dialysis solution, need be given. It is by now obvious, from the teachings here presented, that such solutions are entirely without redox balance but indeed induce a profound lactic acidosis with a pathological decrease in the free cytoplasmic [NAD+]/[NADH] and the free cytoplasmic [ATP]/[ADP][Pi] to which it is linked by equation 5. It is also obvious that redox-balanced solutions, made by the principles outlined herein, would be an advance in the present art.

EXAMPLE 45

Hemodialysis

Using hemodialysis equipment, which is the current major type in use, (see Keshaviah et al., *CRC Critical Reviews in Biomedical Engineering* 9, 201–244, 1983) and using the most common type of dialysis fluid currently in use in the art, which uses between 35 to 45 mMoles/L of Na acetate to correct the anion gap, (see Parsons, F. M. & Stewart, W. K., *The Composition of Dialysis Fluid in Replacement of Renal Function by Dialysis*, 2nd edition (1983) (Drukker W., Parsons F. M. & Maher J. F., eds) pp 148–170, (Martinus, Nijhoff, Hingham) we may obviously predict the effects, upon body organs such as the liver, of such treatment.

Methods

Rats are made uremic as described in the previous example. After five days, they are fasted, attached to a miniature hemodialysis apparatus, heparinized and dialyzed with two different solutions, one representing the most common types of currently used hemodialysis solutions, and another where the anion gap is made up without the use of $HCO_3^-/CO_2$, but instead, with the use of L-lactate/pyruvate and D-B-Hydroxybutyrate/acetoacetate as are given in the class 2-a solutions in this disclosure, as for example 2-a-8, Redox-Balanced Ringers. It should be understood that I do not conclude such a solution as 2-a-8 is the best solution for such a purpose, but I shall show it is superior to the existing art and may be used in the bulk of existing apparatus which contain deaerators* and currently use acetate containing hemodialysis fluids. (Keshaviah et al. *CRC Critical Reviews in Biomedical Engineering* 9, 201–244, 1983.) A few current machine, typically 1 out of 10 in the dialysis centers I have surveyed have dialysis machines of the type described by Miller J. H. et al. *Trans Am Soc artif Internal Organs* 25, 404–408, 1979. Such machines can use $HCO_3^-$ containing solutions. Such $HCO_3^-/CO_2$ solutions are preferred.

The compositions of the two example solutions are given in Table XXV.

TABLE XXV

Example 4
Solution for Hemodialysis of a Uremic Rat.

| Units mmoles L fluid | Normal Plasma N.E.J.M. 283, 1285 1970 | (1) Usual Hemo-dialysis Solution | (2) Redox-Balanced Hemodialysis Solution |
|---|---|---|---|
| Na | 136–145 | 130–135 | 130 |
| K | 3.5–5.0 | 0–1.5 | 4 |
| Ca | 2.1–2.6 | 1.25 | 1.5 |
| free [Ca2+] | [1.06] | | |
| Mg | 0.75–1.25 | 0.5 | — |
| free [Mg2+] | [0.53] | | |
| Σ mEq Cations | 142.7–153.2 | 133.5–140 | 137 |
| Cl | 100–106 | 100.5 | 96 |
| $HCO_3$ | 26–28 | | |
| Σ Pi | 1–1.45 | | |
| $SO_4$ | 0.32–0.94 | | |
| L-lactate | 0.6–1.8 | | 32.1 |
| pyruvate | | | 1.9 |
| Lact/pyr | | | 17 |
| D B OHbutyrate | | | 5 |
| acetoacetate | | | 2 |
| B HB/acac | | | 2.5 |
| acetate | | 33.5–40 | |
| Other | | | |
| Σ mEq anions | 128.7–139.4 | 133.5–140 | 137 |
| Na/Cl | 1.28–145 | 1.29–1.34 | 1.35 |
| Glucose or others | 3.9–5.6 | 0–101 | 0 |
| $CO_2$ | 0.99–1.39 | 0 | 0 |
| pH | 7.35–7.45 | ~6.5 | ~6.5 |
| Σ sOsm | 285–295 | 270.25 to 375 | 272.5 |

(1) The composition of the usual hemodialysis solution is taken from Parson's and Stewart, 1983, cited above.
(2) Composition of solution 2-a-8 is taken from this application except that the lactate/pyruvate ratio is decreased to 17 to accomodate the absence of glucose since most current hemodialysis fluids use acetate without glucose. This composition is chosen to compare with current acetate hemodialysis practice. This solution should not be taken as "ideal" or even as recommended, but rather illustrative.

The rats are dialyzed with solutions 1 and 2 for four hours; the animals are sacrificed and the livers freeze clamped. A group of normal rats, starved 48 hours, are also sacrificed and their livers freeze clamped to serve as controls. Metabolites are measured, as previously described.

In Table XXVI, we see that both acetate and new redox-balanced dialysis fluids elevate liver sugar and the first portion of the gluconeogenic pathway. During acetate dialysis, changes occur throughout the gluconeogenic sequence and the ratio of one metabolite to another changes.

TABLE XXVI

Liver Metabolites from Rats Dialysed with Acetate Dialysis Fluid versus New Redox-Balanced Dialysis Fluids without $HCO_3^-/CO_2$
Values are given as means + S.E.M. in nmoles/g wet weight. A * indicates a significant difference from normal rats at $P < 0.05$ as judged by Student's T Test.

|  | Untreated Starved Rats | Commercial Acetate Dialysis | New Redox-Balanced Dialysis |
|---|---|---|---|
| N | 13 | 10 | |
| $10^{-3} \times$ glucose | 4.81 + 0.21 | 7.94 + 0.42 | 7.2* |
| glucose 6-P | 59 + 2 | 99* + 10 | 88.5* |
| glucose 1-P | 7 + 1 | 11* + 1 | 10.5* |
| fructose 6-P | 17 + 1 | 32* + 3 | 25.2* |
| fructose 1,6 bis-P | 4.6 + 0.4 | 23* + 6 | 6.9 |
| DHAP | 11 + 1 | 36* + 4 | 16.5 |
| 3-phosphoglycerate | 156 + 14 | 581* + 62 | 234 |
| PEP | 73 + 5 | 330* + 40 | 110 |
| pyruvate | 10 + 1 | 27* + 6 | 1260* |
| L-lactate | 171 + 17 | 721 + 208 | 21300* |
| L-malate | 268 + 28 | 592* + 84 | 402 |
| α-ketoglutarate | 118 + 13 | 86 + 17 | 177 |
| isocitrate | 17 + 2 | 41* + 3 | 25.5 |
| citrate | 308 + 42 | 944* + 85 | 462 |
| acetoacetate | 638 + 33 | 643 + 66 | 1330* |
| D-B OHbutyrate | 1643 + 75 | 983* + 83 | 3300* |
| UDP-glucose | 350 + 15 | 367 + 25 | 350 |
| UTP | 205 + 9 | 186 + 8 | 205 |
| acetate | 20 | 25000 | 20 |

In Table XXVII are presented the changes in the controlling co-factor ratios after the two types of dialysis.

TABLE XXVII

Free Nucleotide Ratios in Freeze Clamped Rat Liver After Acetate and Redox-Balanced Hemodialysis
Values are given as mean + S.E.M. An * indicates a significant difference from control values of $P < 0.02$ as judged.

| (n) | Starved Control (13) | Acetate Dialysis (10) | Redox-Balanced Dialysis |
|---|---|---|---|
| Cytoplasmic $\frac{[NAD^+]}{[NADH]}$ | 587 + 86 | 391 + 35 | 587 |
| $10^3 \times \frac{[NADP^+]}{[NADPH]}$ | 7.3 + .7 | 2.1* + .3 | 7.3 |
| $\frac{[\Sigma ATP]}{[\Sigma ADP][\Sigma Pi]} M^{-1}$ | 3710 + 580 | 2090 + 280 | 3710 |
| mitochondrial $\frac{[NAD^+]}{[NADH]}$ | 8.1 + 0.7 | 13.8* + 1.4 | 8.1 |

In Table XXVII we see that acetate dialysis causes oxidation of the mitochondrial $[NAD^+]/[NADH]$ ratio and reduction of the free cytoplasmic $[NADP^+]/[NADPH]$ ratio while redox-balanced dialysis causes no changed as judged by the isocitrate/α-ketoglutarate ratio.

In Table XXVIII are presented the results of the measurement of the Ca, Mg, phosphate and pyrophosphate content of rat liver after acetate versus redox-balanced hemodialysis.

TABLE XXVIII

Changes in Mg, Ca and Phosphate Compounds in Liver Following Acetate versus Redox-Balanced Hemodialysis.

|  | Control | Acetate Hemodialysis | Redox-Balanced Hemodialysis |
|---|---|---|---|
| n | 13 | 10 | |
| Ca | 1.33 | +2.89 | 0 |
| Mg | 10.1 | +1.8 | 0 |
| PPi | 0.024 | +2.00 | 0 |
| Pi | 4.22 | +3.73 | 0 |
| Σ Adenine Nucleotide Pi | 9.32 | +0.07 | 0 |
| Σ Guanine Nucleotide Pi | 1.76 | +0.19 | 0 |
| Σ Glycolytic Pi | 0.36 | +0.86 | +.50 |
| Σ Pi Increased from All measured metabolites | 15.71 | +8.85 | +.50 |

We see in Table XXVIII that acetate dialysis raises inorganic pyrophosphate 200 times while redox-balanced dialysis makes no change. Acetate hemodialysis increases liver calcium three fold; redox-balanced dialysis makes no change. Acetate hemodialysis increases total liver metabolizable phosphate by 8.8 m moles/g, while redox-balanced dialysis increases liver metabolizable phosphate by only 0.5 m moles/g, or 16 times. The "hidden" phosphate, inaccessible to dialysis after acetate hemodialysis, is the largest ever seen. The metabolic pathology is therefore even greater than that seen in Example 44.

EXAMPLE 45

Solutions of this invention when administered not only regulate redox state and phosphorylation, but also further tend to normalize the following states:
(1) Distribution of water between intracellular and extracellular fluid.
(2) Distribution of the inorganic electrolytes $Na^+$, $K^+$, $Cl^-$, and $Ca^{2+}$ between intracellular and extracellular fluid, and
(3) Transmembrane cellular potential. ΔE
The following equations state the governing scientific laws involved:

0. Eqn 0 - The Second Law
   J. Willard Gibbs. On the equilibrium of heterogeneous substances. J Conn Acad Sci 1876: III: 343.
0-1 Definition of Gibbs Free Energy and Other Properties of State:
   $G = H - TS$
   where:
   $G \sim$ Gibbs free energy
   $H \sim$ Enthalpy or heat content
   $T \sim$ absolute temperature
   $S \sim$ Entropy, or state of randomness or disorder
0-1a Entropy may be more rigorously defined by statistical and quantum mechanics in the Boltzmann Equation:
   $S = k_B \ln \Omega$
   where:
   $S \sim$ Entropy $k_B \sim$ Boltzmann constant $= \frac{R \text{ (gas constant)}}{\text{Avagadro's number}}$
   $= 1.38 \times 10^{-23} J/°K$ $\Omega \sim$ Degeneracy
0-2 $\Delta G = \Delta H - T \Delta S$
   where $\sim$ change in -continued 0-3 Standard Free Energy $\sim \Delta G^o$ $$\Delta G = \Delta G^o + RT \ln \frac{[products]}{[reactants]}$$

where:
R $\sim$ gas constant
 = 1.987 calories/°K./mole and °K. $\sim$ 273 + °C.
T = °K.
ln $\sim$ 2.303 log$_{10}$ 0-3a $\Delta G^o = -RT \ln K_{eq}$
where:

$$K_{eq} \sim \frac{[products]}{[reactants]}$$

0-4 At equilibrium, $\Delta G = 0$, so in $A + B \rightleftharpoons C + D$ $$\Delta G = -RT \ln K_{eq} + RT \ln \frac{[C][D]}{[A][B]}$$

where:
[ ] $\sim$ activity or $\sim$ concentration

"A theory is the more impressive the greater the simplicity of its premises, the more different are the kinds of things it relates, and the more extended is its range of applicability . . . It is the only physical theory of universal content which I am convinced, that within the framework of applicability of its basic concepts, will never be overthrown.

A. Einstein

I Eqn 1 - The Henderson-Hasselbalch Equation
The major buffer and controller of extra- and intracellular pH.
Henderson LJ. Blood, A Study in General Physiology. Silliman Lectures, Yale University Press, 1928

1.a
$$pH = pK_{a'} + \log \frac{[HCO_3^-]}{[CO_2]}$$

where:
pK$_{a'}$ = 6.10 at 38° C. and serum concentrations of electrolytes 1.b The solubility of CO$_2$ in fluid, i.e. dissolved CO$_2$ gas plus H$_2$CO$_3$ from:

$$CO_2 + H_2O \rightleftharpoons H_2CO_3$$

$$[CO_2] \text{ in mmol/liter} = \frac{pCO_2 \text{ in mmHg}}{760 \text{ mmHg}} \cdot \frac{\alpha \text{ml } CO_2/\text{ml of } H_2O}{22.26 \text{ L/mole}} \cdot \frac{1000 \text{ mmol}}{\text{mole}}$$

$\alpha_{CO_2}$ = 0.553/ml serum H$_2$O at 38° C. from:
Van Slyke DD. J Biol Chem 73: 765-799, 1928.

1.c The pH of a bicarbonate containing solution to which has been added a carbocylic acid such as acetic, lactic, acetoacetic acid with a pK' in the 3 to 4 range and where the concentration of HCO$_3$ is much larger than the concentration of carboxcylic acid:

$$pH = pK_{a'} - \log \left\{ \frac{[HCO_3^-]}{2([HCO_3^-] - [HA])} - \frac{1}{2} \right\}$$

Thus adding 1.8 mM Hlactate and 0.2 mM Hpyruvate to 25 mM NaHCO$_3$ yields what pH?

$$pH = pK_{a'} - \log \left\{ \frac{[25]}{2([HCO_3 - [HA])} - \frac{1}{2} \right\}$$

= 6.1 − (1.36)
= 7.46

-continued

II Donnan Equilibrium Equation
Donnan FG. Z Electrochem 17: 572, 1911
Donnan FG. Chem Rev 1: 73-90, 1924.

1. From Gibbs (Eqn 0)

$$RT \ln \frac{[Cl^-]_1}{[Cl^-]_2} + RT \ln \frac{[Na^+]_1}{[Na^+]_2} = 0$$

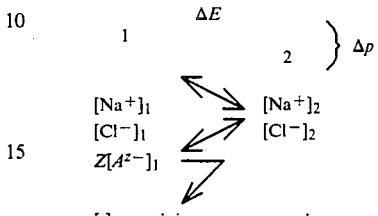

[ ] $\simeq$ activity $\simeq$ concentration
A $\simeq$ non-diffusable polyanion
Z $\simeq$ valance of polyanion Or:

1.a
$$\frac{[Cl^-]_1}{[Cl^-]_2} = \frac{[Na^+]_2}{[Na^+]_1}$$

Therefore: $\frac{[Cl^-]_1}{[Cl^-]_2} = \frac{[Cl^-]_2}{[Cl^-]_1 + Z[A^{z-}]_1} = \frac{[Na^+]_2}{[Na^+]_1}$ and for polyvalents:

$$\left( \frac{[Anions]_1}{[Anions]_2} \right)^{1/z \text{ anions}} = \left( \frac{[Cations]_2}{[Cations]_1} \right)^{1/z \text{ cations}}$$

2. From the Law of Electrically Neutrality:
[Na$^+$]$_2$ = [Cl$^-$]$_2$
[Na$^+$]$_1$ = [Cl$^-$]$_1$ + Z[A$^{z-}$]$_1$ 3. Quadratic equation:

$$x = \frac{-b \pm \sqrt{b^2 - 4ac}}{2a}$$

Example: Consider albumin dialysed against 100% CO$_2$/ 3.13 NaHCO$_3$ buffer with 1.17 mM albumin (i.e. 8% solution). Hypothetically keep charge on albumin at −20/mole.

$$\frac{[HCO_3^-]_i}{[HCO_3^-]_o} = \frac{[HCO_3^-]_o}{[HCO_3^-]_i + 20[Alb^{-20}]} = \frac{[Na^+]_o}{[Na^+]_i}$$

$$\frac{[HCO_3^-]_i}{[3.13 \times 10^{-3}]} = \frac{[3.13 \times 10^{-3}]}{[HCO_3^-]_i + 20[1.17 \times 10^{-3}]}$$

[HCO$_3^-$]$_i$ = 0.4 × 10$^{-3}$M

II Eqn 2 Multicomponent Donnan Equilibrium System for Solutions Such as the Hemodialysis of Blood Plasma Electrolytes:
where $\Delta p = 0$ and all components but albumin are permeant. Subscript $_o$ $\sim$ in dialysis fluid, subscript $_i$ $\sim$ in patient's plasma, $\Delta p$ $\sim$ difference in pressure.

2.a
$$\frac{[Na^+]_i}{[Na^+]_o} = \frac{[K^+]_i}{[K^+]_o} = \left| \frac{[Ca^{2+}]_i}{[Ca^{2+}]_o} \right|^{\frac{1}{2}} = \left| \frac{[Mg^{2+}]_i}{[Mg^{2+}]_o} \right|^{\frac{1}{2}} =$$

$$\frac{[Cl^-]_o}{[Cl^-]_i} = \frac{[HCO_3^-]_o}{[HCO_3^-]_i} = \left| \frac{[Pi]_o}{[Pi]_i} \right|^{1/1.8} = \frac{[lac^-]_o}{[lac^-]_i} =$$

-continued $$\frac{[pyr^-]_o}{[pyr^-]_i} = \frac{[acac^-]_o}{[acac^-]_i} = \frac{[BHB^-]_o}{[BHB^-]_i} = \frac{[acet^-]_o}{[acet^-]_i}.$$

Statement of electrical neutrality on two sides of an uncharged membrane 2.b.1. $[Na^+]_o + [K^+]_o + 2[Ca^{2+}]_o + 2[Mg^{2+}]_o = [Cl^-]_o + [HCO_3^-]_o + 1.8[Pi^{-1.8}]_o + [lac^-]_o + [pyr^-]_o + [acac^-]_o + [BHB^-]_o + [acet^-]_o$ 2.b.2. $[Na^+]_i + [K^+]_i + 2[Ca^{2+}]_i + 2[Mg^{2+}]_i = [Cl^-]_i + [HCO_3^-]_i + 1.8[Pi^{-1.8}]_i + [lac^-]_i + [pyr^-]_i + [acac^-]_i + [BHB^-]_i + [acet^-]_i + Z[prot^{z-}]_i$ Distribution of cations on two sides of the membrane:

2.c $$[K^+]_i = [K^+]_o \frac{[Na^+]_i}{[Na^+]_o} ; [Ca^{2+}]_i = [Ca^{2+}]_o \left| \frac{[Na^+]_i}{[Na^+]_o} \right|^2 ;$$

$$[Mg^{2+}]_i = [Mg^{2+}]_o \left| \frac{[Na^+]_i}{[Na^+]_o} \right|^2$$

Distribution of Anions:

2.d $$[Cl^-]_i = \frac{[Na^+]_o}{[Na^+]_i} [Cl^-]_o; [HCO_3^-]_i = \frac{[Na^+]_o}{[Na^+]_i} [HCO_3^-]_o;$$

$$[acet^-]_i = \frac{[Na^+]_o}{[Na^+]_i} [acet^-]_o; [Pi]_i = \left| \frac{[Na^+]_o}{[Na^+]_i} \right|^{1.8} [Pi]_o;$$

$$[lac^-]_i = \frac{[Na^+]_o}{[Na^+]_i} [lac^-]_o; [pyr^-]_i = \frac{[Na^+]_o}{[Na^+]_i} [pyr^-]_o;$$

$$[acac^-]_i = \frac{[Na^+]_o}{[Na^+]_i} [acac^-]_o; [BHB^-]_i = \frac{[Na^+]_o}{[Na^+]_i} [BHB^-]_o$$

Now solving for $[Na^+]_i/[Na^+]_o$ for a dialysis fluid$_o$ of known composition:

2.e $$\frac{[Na^+]_i}{[Na^+]_o} [Na^+]_o + [K^+]_o + \frac{2[Na^+]_i}{[Na^+]_o} |[Ca^{2+}]_o +$$

$$[Mg^{2+}]_o| = \frac{[Na^+]_o}{[Na^+]_i} [Cl^-]_o + [HCO_3^-]_o + [acet^-]_o +$$

$$[lact^-]_o + [pyr^-]_o + [acac^-]_o + [BHB^-]_o +$$

$$1.8 \left| \frac{[Na^+]_o}{[Na^+]_i} \right|^{0.8} [Pi]_o + \frac{[Na^+]_i}{[Na^+]_o} |Z|[prot^{z-}]$$

and:

2.f $$\frac{[Na^+]_o + [K^+]_o}{[Na^+]_o^2} [Na^+]_i^2 +$$

$$\frac{2([Ca^{+2}]_o + [Mg^{2+}]_o)}{[Na^+]_o^3} [Na^+]_i^3 - |Z| \frac{[prot^{z-}]}{[Na^+]_o} [Na^+]_i -$$

$(1.8[Pi]_o[Na^+]_o^{0.8})[Na^+]_i^{(-0.8)} = [Cl^-]_o + [HCO_3^-]_o + [acet^-]_o + [lact^-]_o + [pyr^-]_o + [acac^-]_o + [BHB^-]_o$ Plasma [concentration] $\sim 0.935 \times$ plasma H$_2$O [concentration]

III Eqn 3. Nernst Equation - $\Delta E$

Nernst W. Theoretical Chemistry 4th Edition, 1904, McMillan, London. See also Silliman Lecture, 1906, Yale U. Press, New Haven.

3.

$$\Delta E = -\frac{RT}{nF} \ln \frac{[anion^-]outside}{[anion^-]inside}$$

or:

$$\Delta E = -\frac{RT}{nF} \ln \frac{[cation^+]inside}{[cation^+]outside}$$

where:
at 38° C. $T \sim 311°$ K.
$R$, the gas constant $\sim 8.314$ joules/degree/mole
$n \sim$ number of equivilents
F, the Faraday, $\sim 96,494$ coulombs
$\Delta E \sim$ potential in volts
To convert ln to log$_{10}$, multiply by 2.303
From Cornell N, Anal Biochem 1980; 102: 326–331, for isolated hepatocytes from starved rats incubated in Krebs-Henseleit.

$$\Delta E = -0.0617 \log \frac{[0.128 \text{ M Cl}^-]outside}{[0.041 \text{ M Cl}^-]inside}$$

$\Delta E = -0.0305$ V or $-30.5$ mV
and for cat brain, from Eccles JC. The Physiology of Nerve Cell, 1957, Johns Hopkins U Press, Baltimore.

$$\Delta E = -0.0617 \log \frac{[0.125 \text{ M Cl}^-]outside}{[0.009 \text{ M Cl}^-]inside}$$

$\Delta E = -0.0705$ V or $-70.5$ mV 3.b Redox Potential of Half Reactions $$E_h = E^o + \frac{RT}{nF} \ln \frac{[oxidized]}{[reduced]}$$

where:
$R \sim 8.31431$ J/°K./mole
$T \sim$ °K.
$n \sim$ number of electrons
F $\sim$ Faraday $\sim 96,494$ coulombs
ln $\sim 2.303 \log_{10}$ IV Eqn 4 Redox State Equations. [NAD$^+$]/[NADH] or [NADP$^+$]/[NADPH].

Near equilibrium reactions are given a number depending upon location. The $E^{o'}$ of the [NAD$^+$]/[NADH] couple at pH 7 is $-0.32$ V. That of the [NADP$^+$]/[NADPH] couple, $-0.335$ V.

| Abbreviation Definition of $K_{eq}$ Enzyme No. | Value of $K_{eq}$ at pH = 0 | Value of $K_{eq}$ at pH 7 | $E^{o'}$ at pH 7.0 oxidized/reduced V | $E^{o'}$ at pH 7.0 CO$_2$ = 1.5 mM or 0.5 mM NH$_4^+$ or 1 mM Pi V |
|---|---|---|---|---|
| Cytoplasmic NAD - Linked Dehydrogenases | | | | |
| 4C1 $K_{LDH} = \frac{[pyruvate^-][NADH][H^+]}{[1\text{-lactate}^-][NAD^+]}$ EC 1.1.1.27 | $1.11 \times 10^{-11}$M | $1.11 \times 10^{-4}$ | $-0.201$ | |

-continued

| | | | | | |
|---|---|---|---|---|---|
| 4C2 | $K_{MDH} = \dfrac{[\text{oxaloacetate}^{2-}][\text{NADH}][\text{H}^+]}{[\text{l-malate}^{2-}][\text{NAD}^+]}$<br>EC 1.1.1.37 | $2.86 \times 10^{-12}$M | $2.86 \times 10^{-5}$ | $-0.184$ | |
| 4C3 | $K_{GPDH} = \dfrac{[\alpha\text{-glycerol-P}^{2-}][\text{NADH}][\text{H}^+]}{[\text{DHAP}^{2-}][\text{NAD}^+]}$<br>EC 1.1.1.94 | $1.3 \times 10^{-11}$M | $1.3 \times 10^{-4}$ | $-0.203$ | |
| 4C4 | $K_{GAPDH} = \dfrac{[1,3\ \text{DiPG}^{4-}][\text{NADH}][\text{H}^+]}{[\text{GAP}^{2-}][\text{P}_i^{2-}][\text{NAD}^+]}$<br>EC 1.2.1.12 | $5.3 \times 10^{-8}$M | $5.3 \times 10^{-1}$ | $-0.302$ | $-0.222$ Here, Pi is a reactant |
| | $K_{ADH} = \dfrac{[\text{acetaldehyde}][\text{NADH}][\text{H}^+]}{[\text{ethanol}][\text{NAD}^+]}$<br>EC 1.1.1.1 | $1.94 \times 10^{-11}$M | $1.9 \times 10^{-4}$ | $-0.209$ | |
| | $K_{IdDH} = \dfrac{[\text{d-fructose}][\text{NADH}][\text{H}^+]}{[\text{d-sorbitol}][\text{NAD}^+]}$<br>EC 1.1.1.14 | $1.14 \times 10^{-9}$M | $1.14 \times 10^{-2}$ | $-0.262$ | |

Mitochondrial NAD - Linked Dehydrogenases

| | | | | | |
|---|---|---|---|---|---|
| 4M1 | $K_{HBDH} = \dfrac{[\text{acetoacetate}^-][\text{NADH}][\text{H}^+]}{[\text{d-B-hydroxybutyrate}^-][\text{NAD}^+]}$<br>EC 1.1.1.30 | $4.93 \times 10^{-9}$M | $4.93 \times 10^{-2}$ | $-0.281$ | |
| 4M2 | $K_{GlDH} = \dfrac{[\alpha\text{-KG}^{2-}][\text{NH}_4^+][\text{NADH}][\text{H}^+]}{[\text{l-glutamate}][\text{NAD}^+]}$<br>EC 1.4.1.3 | $3.87 \times 10^{-13}$M$^2$ | $3.87 \times 10^{-6}$M | $-0.158$ | $-0.257$ |
| | $K_{AlDH} = \dfrac{[\text{acetate}^-][\text{NADH}][\text{H}^+]^2}{[\text{acetaldehyde}][\text{NAD}^+]}$<br>EC 1.2.1.3 | $1.45 \times 10^{-5}$M$^2$ | $1.45 \times 10^{+9}$ | $-0.596$ | |

Cytoplasmic NADP - Linked Dehydrogenases

| | | | | | |
|---|---|---|---|---|---|
| 4T1 | $K_{IcDH} = \dfrac{[\alpha\text{-KG}^{2-}][\text{CO}_2][\text{NADPH}]}{[1_s\text{-isocitrate}^{3-}][\text{NADP}^+]}$<br>EC 1.1.1.42 | 1.17M | 1.17M | $-0.337$ | $-0.422$ Here, CO$_2$ is a reactant |
| 4T2 | $K_{\text{Malic Enz}} = \dfrac{[\text{pyruvate}^-][\text{CO}_2][\text{NADPH}]}{[\text{malate}^{2-}][\text{NADP}^+]}$<br>EC 1.1.1.40 | $3.44 \times 10^{-2}$M | | | |
| 4T3 | $K_{6PGDH} = \dfrac{[\text{ribulose 5-P}^{2-}][\text{CO}_2][\text{NADPH}]}{[\text{6-phosphogluconate}^{3-}][\text{NADP}^+]}$<br>EC 1.1.1.43 | $1.72 \times 10^{-1}$M | | | |

Linking Isomerases

| | | | | | |
|---|---|---|---|---|---|
| 4L1 | $K_{GOT} = \dfrac{[\alpha\text{-KG}^{2-}][\text{l-aspartate}^-]}{[\text{l-glutamate}^-][\text{oxaloacetate}^-]}$<br>EC 2.6.1.1 | 6.61 | | | |
| 4L2 | $K_{GPT} = \dfrac{[\alpha\text{-KG}^{2-}][\text{l-alanine}]}{[\text{l-glutamate}^-][\text{pyruvate}^-]}$<br>EC 2.6.1.2 | 1.52 | | | |
| 4L3 | $K_{TPI} = \dfrac{[\text{dihydroxyacetone-P}^{2-}]}{[\text{glyceraldehyde 3-P}^{2-}]}$<br>EC 5.3.1.1 | 22 | | | |

References for Values of Near-Equilibrium Reactions in Equation 4

| Equation | Abbreviation | Reference |
|---|---|---|
| 4C1 | $K_{LDH}$ | Williamson DH, Lund P, Krebs HA. Biochem J 103: 514–527, 1967 |
| 4C2 | $K_{MDH}$ | Guynn R, Gelberg H, Veech RL. J Biol Chem 248: 6957–6965, 1973 |
| 4C3 | $K_{GPDH}$ | Russman W. Thesis, Munich, 1969. |
| 4C4 | $K_{GAPDH}$ | Cornell N, Leadbetter M, Veech RL. J Biol Chem 254: 6522–6527, 1979 |
| 4M1 | $K_{HBDH}$ | Williamson DH, Lund P, Krebs HA. Biochem J 103: 514–527, 1967 |
| 4M2 | $K_{GLDH}$ | Engel P, Dalziel K. Biochem J 105: 691–695, 1967 |
| 4T1 | $K_{IcDH}$ | Londesbourgh J, Dalziel K. Biochem J 110: 217–222, 1968 |
| 4T2 | $K_{M.E.}$ | Veech R, Eggleston LV, Krebs HA. Biochem J 115: 609–619, 1967 |

| 4T3 | $K_{6PGDH}$ | Villet R, Dalziel K. Biochem J 115: 633–638, 1969 |
| 4L1 | $K_{GOT}$ | Krebs HA. Adv Enz Reg 13: 449–472, 1975 |
| 4L2 | $K_{GPT}$ | Krebs HA. Adv Enz Reg 13: 449–472, 1975 |
| 4L3 | $K_{TPI}$ | Veech RL, Raijman L, Dalziel K, Krebs HA. Biochem J 115: 837–842, 1969 |

*The enzyme aldose reductase EC 1.1.1.21 may be redox active during fructose infusion in certain tissues. The reaction is:

$$K_{Aldose\ R} = \frac{[d\text{-sorbitol}][NADPH][H^+]}{[d\text{-glucose}][NADP^+]} \sim 2 \times 10^{-11} \text{ M.* My estimate}$$

For description, see Hayman S, Kinoshita JH. J Biol Chem 240: 877, 1965

V Eqn 5 Phosphorylation State Equations - $[\Sigma ATP]/[\Sigma ADP][\Sigma Pi]$
Veech RL, Lawson JR, Cornell NW, Krebs HA. J Biol Chem 254: 6538–6547, 1979

5a. The equilibrium constant of the glyceraldehyde 3-phosphate dehydrogenase (EC 1.1.1.29) and 3 phosphoglycerate kinase reactions (EC 2.7.2.3) at 38° C., I = 0.25, and free $[Mg^{2+}]$ = 1 mM is:

$$K_{G+G} = \frac{[\Sigma 3PG]}{[\Sigma GAP]} \cdot \frac{[\Sigma ATP]}{[\Sigma ADP][\Sigma Pi]} \cdot$$

$$\frac{[NADH][H^+]}{[NAD^+]} = 1.83 \times 10^{-4}$$

5b. Combining the above reaction with $K_{LDH}$ and substituting $[DHAP] = [GAP]/22$ $$\frac{K_{G+G}}{K_{LDH}} = \frac{[\Sigma 3PG]}{[\Sigma GAP]} \cdot \frac{[\Sigma ATP]}{[\Sigma ADP][\Sigma Pi]} \cdot$$

$$\frac{[1\text{-lactate}]}{[\text{pyruvate}]} = 1.65 \times 10^{+7} M^{-1}$$

5c. Or:

$$\text{Free Cytoplasmic } \frac{[\Sigma ATP]}{[\Sigma ADP][\Sigma Pi]} = \frac{[\Sigma DHAP]}{[\Sigma 3PG]} \cdot$$

$$\frac{[\text{pyruvate}]}{[1\text{-lactate}]} \times 7.5 \times 10^{+5} M^{-1}$$

5d. Alternatively, from the creatine phosphokinase reaction (EC 2.7.3.2)

$$K_{CK} = \frac{[\Sigma ATP]}{[\Sigma ADP]} \cdot$$

$$\frac{[\text{creatine}]}{[\Sigma \text{creatine-P}][H^+]} = 1.66 \times 10^{-9} M^{-1}$$

For the Pyrophosphorylation State or [PPi]/[Pi]:
Lawson JWR, Guynn RW, Cornell NW, Veech RL. In Gluconeogenisis (Hanson RW, Mehlman MA eds) pp 481–511, John Wiley, New York, 1976

5e. From the UDPG Pyrophosphorylase reaction (EC 2.7.7.9):

$$\text{Free Cytoplasmic [PPi]} = \frac{[\Sigma \text{glucose 1-P}][\Sigma UTP]}{[\Sigma UDPglucose]°K_{UDPGPPiase}}$$

where $K_{UDPGPPiase} = 4.55$

5f. For liver and blood glucose:

$$K_{G\text{-}PPi\ Trans\ Pase} = \frac{[\Sigma \text{ Glucose 6-P}][\Sigma Pi]}{[\text{Glucose}][\Sigma PPi]} = 45.9$$

5g.

$$K_{G6\text{-}P\text{-}PPi\ Trans\ Pase} = \frac{[\text{free F 1,6 diP}][\Sigma Pi]}{[\Sigma \text{fructose 6-P}][\Sigma PPi]} = 29.0$$

VI Eqn 6 Determination of Osmotic Pressure - $\pi$
Van't Hoff JH. Arch Neerl Sci 20: 239–303, 1886
$\pi = \Sigma[C] RT$
where:
$\pi \sim$ osmotic pressure in atmospheres (relative to pure $H_2O$)

$\Sigma[C] \sim$ [concentrations] of solutes in mole/liter
$R \sim$ gas constant = 0.082 liter atmospheres/mole/degree K
$T \sim 273 + °C$.

VII Eqn 7 The Equation of State of the Cell
Relating the E across the cell membrane, the distribution of $[Na^+]$, $[K^+]$, $[Cl^-]$, and $[Ca^{2+}]$ between extracellular fluid and cytoplasmic $H_2O$ and hence cell volume to the cytoplasmic $[ATP]/[ADP][Pi]$ $$\Delta G_{Na/K\ ATPase} = \Delta G°_{ATPase} + \Delta G°_{ions} +$$

$$RT \ln \frac{[\Sigma ADP][\Sigma Pi]}{[\Sigma ATP]} +$$

$$RT \ln \frac{[Na^+]_o^3 [K^+]_i^2 [Cl^-]_o}{[Na^+]_i^3 [K^+]_o^2 [Cl^-]_i} + T\Delta S$$

Since $\Delta G = 0$, then:
$0 = -7.73$ kcal/mole $+ 0 + (-6.3$ kcal/mole) $+$
$\qquad$ 8.5 kcal/mole $+ 5.5$ kcal/mole As 1 kcal/mole = $\frac{0.082 \text{ liter atmos/mole/°K.}}{1.98 \times 10^{-3} \text{ kcal/mole/°K.}} \times$

$$\frac{1}{22.4 \text{ l/mole}} = 1.85 \text{ atmospheres}$$

then the $TS$ term = $5.5 \times 1.85 = 10.2$ atmospheres.
And further from Van't Hoff (Eqn 6)

$$\Sigma[C]_{in} - \Sigma[C]_{out} = \frac{\pi}{RT}$$

$\Sigma[C]_{in} - \Sigma[C]_{out} = 0.40$ moles/L
Eqn 7 states that since uT $H_2O$ outside = uT $H_2O$ inside, the cell is prevented from swelling by the $Na^+/K^+$ ATPase which electroneutrally pumps out 2 mOsmoles/ATP hydrolysed. The $\Delta E$ across the cell (membrane) is reflected by the distribution of $[Cl^-]_o/[Cl^-]_i$ in accordance with the Nernst equation (Eqn 3). The $T\Delta S$ or decreased entropy within the living cell represents the increase "order" characteristic of the living cell. See Eqn 0.

7b. From the high capacity $Na^+/Ca^{2+}$ exchanger written in an electroneutral manner reflecting the free permeability of $Cl^-$ in accordance with the dictates of the Nernst equation, (Eqn 3):

$$3Na^+_o + Ca^{2+}_i + Cl^-_o \rightleftharpoons 3Na^+_i + Ca^{2+}_o + Cl^-_i$$

The net osmolar movement of eqn 7a is 2 osmoles $\longrightarrow$ outside.
In contrast, the net movement of eqn 7b is 3 osmoles $\longrightarrow$ inside, requiring the $Na^+/K^+$ ATPase to cycle 3 times for each 2 times the $Na^+/Ca^{2+}$ exchange mechanism operates in order to maintain osmotic equilibrium.
The gradient $[Ca^{2+}]_i/[Ca^{2+}]_o$ is thus a direct function of the $[Na^+]_o^3/[Na^+]_i^3$, (the $[Cl^-]_o/[Cl^-]_i$), and a function of the phosphorylation and entropy state of the cell.

It will be clear to those skilled in the art that equation 7 is the statement of the reaction which links the external environment of the cell to its internal environment and metabolic machinery. Extracellular fluid is thus a creation of the metabolic process of the cell. Changing the external [Na+], [K+], [Cl−], or [Ca2+], or the [H2O] must necessarily effect the same parameters inside the cell.

Additionally, the redox and phosphorylation states, the ΔE, and the TΔS of the cell are all related and therefore manipulable by the relationships given.

To control these parameters one needs to use solutions as provided herein which include defined concentrations of Na+, K+, Cl−, and Ca++ and the related ions HCO3−, H+, at a defined Mg2+ concentration and with a defined osmotic pressure.

Thus, the present invention provides a process for regulating:

(1) Distribution of water between intracellular and extracellular fluid.

(2) Distribution of the inorganic electrolytes Na, K, Cl and Ca between intracellular and extracellular fluid.

(3) and transmembrane cellular potential

This process is practiced by contacting cells with aqueous near-equilibrium couples as taught by this inventor or by varying the external concentration of Na+, K+, Cl− or Ca2+. For example a solution with low Na:Cl ratio raises the phosphorylation potential (See Table III above). In other circumstances, raising Na:Cl outside may raise cellular [Ca2+] for example in rat liver.

Having now fully described the invention, it will be apparent to one of ordinary skill in the art that many changes and modifications can be made thereto without departing from the spirit or scope of the invention as set forth herein.

I claim:

1. An aqueous solution suitable for fluid therapy comprising on the basis of 1 liter of solution about 130 to 165 mM sodium, about 80 to 130 mM chloride, and about 0.5 to 60 mM at least one of the following:

(a) l-lactate and pyruvate, the l-lactate to pyruvate ratio being about 20:1 to 1:1, (b) d-beta hydroxybutyrate and acetoacetate, the d-beta hydroxybutyrate to acetoacetate ratio being about 6:1 to 0.5:1, the sodium to chloride ratio being about 1.24 to 1.6, and the pH ranging from about 5 to 9.

2. A solution in accordance with claim 1 containing from about 0.5 to 5 mM calcium.

3. A solution in accordance with claim 1 containing from about 0.5 to 3 mM magnesium.

4. A solution in accordance with claim 1 containing from about 0.5 to 10 mM potassium.

5. A solution in accordance with claim 1 containing from 0 to about 300 mM glucose.

6. A solution in accordance with claim 1 containing from about 0.5 to 60 mM of bicarbonate and carbon dioxide, the bicarbonate to carbon dioxide ratio being about 0.1:1 to 55:0.1.

7. An electrolyte solution suitable for dilution and for resuscitation therapy comprising on the basis of 1 liter of solution 160 to 2400 mM sodium and sufficient mM chloride to produce a sodium to chloride ratio from about 1.24 to 1.6, and from about 80 to 465 mM of at least one of the following:

(a) l-lactate and pyruvate, the l-lactate to pyruvate ratio being about 20:1 to 1:1, (b) d-beta hydroxybutyrate and acetoacetate, the d-beta-hydroxybutyrate to acetoacetate ratio being about 6:1 to 0.5:1, the pH being about 5 to 9.

8. The solution of claim 7 which has been diluted with an aqueous dextrose solution to produce a product solution containing less than about 130 mM sodium.

9. An in vivo process for maintaining normal cellular free [NAD+]/[NADH] ratios and phosphorylation states which comprises introducing parenterally into a living mammal a physiologically effective amount an aqueous solution comprising on the basis of 1 liter of solution about 130 to 165 mM sodium, about 80 to 130 mM chloride, and about 0.5 to 80 mM of at least one of the following:

(a) l-lactate and pyruvate, the l-lactate to pyruvate ratio being about 20:1 to 1:1, (b) d-beta hydroxybutyrate and acetoacetate, the d-betahydroxybutyrate to acetoacetate ratio being about 6:1 to 0.5:1, the sodium to chloride ratio being about 1.24 to 1.6, and the pH ranging from about 5 to 9.

10. The process of claim 9 wherein said solution additionally contains from 0 to about 300 mM glucose.

11. The process of claim 9 wherein said solution additionally contains about 10 to 60 mM bicarbonate and carbon dioxide, the bicarbonate to carbon dioxide ratio being about 0.1:1 to 55:0.1 and wherein the free cytosolic [NADP+]/[NADPH] ratios are also maintained.

12. In a process where renal function of a living mammal is replaced by dialysis and wherein the dialysis fluid contains dissolved therein from about 130 to 165 mM sodium, and also from about 81 to 130 mM chloride, and said fluid has a sodium to chloride ratio ranging from about 1.24 to 1.6, a pH from about 5 to 9, and a milliosmolarity from about 260 to 800, the improvement which comprises including in said dialysis fluid from about 25 to 455 mM of at least one of the following substance pairs in the respective concentrations indicated:

from about 0 to 55 mM bicarbonate and carbon dioxide, the bicarbonate to carbon dioxide ratio being 0.1:1 to 55:0.1, from about 0 to 55 mM of l-lactate and pyruvate, the l-lactate to pyruvate ratio being 20:1 to 1:1, and from about 0 to 55 mM of d-betahydroxybutyrate and acetoacetate, the d-betahydroxybutyrate to acetoacetate ratio being 6:1 to 0.5:1.

13. The process of claim 8 wherein said solution additionally contains from 0 to about 45 mM bicarbonate.

14. The process of claim 13 wherein said pH of said solution is achieved by admixture of said bicarbonate to said carboxylic acid and wherein the final concentrations thereof are such as to produce a pH in said solution which satisfies the relationship:

$$pH = pK_{a'} - \log\left(\frac{[HCO_3^-]}{2([HCO_3^-] - [HA])} - \frac{1}{2}\right)$$

wherein:

$pK_{a'}$ is defined as the apparent dissociation constant of carbonic acid under physiological conditions at physiological temperature and ionic strength and is taken to be 6.1, $[HCO_3^-]$ is the concentration of bicarbonate present in said solution, $[HA]$ is the concentration of said carboxylic acid, and pH is conventionally defined as the negative logarithm to the base ten of the hydrogen ion concentration of the resulting said solution.

15. The process of claim 13 wherein said carbon dioxide is produced in situ by including in said solution a dissolved mixture of
(A) at least one member of the group consisting of physiologically acceptable bicarbonate salts, and
(B) at least one carboxylic acid selected from the group consisting of l-lactic acid, pyruvic acid, d-betahydroxybutyric acid, and acetoacetic acid,
and provided that:
(a) the total molar quantity of said carboxylic acid and the total molar quantity of said bicarbonate salts is such that there is produced in said solution a quantity of dissolved carbon dioxide sufficient to make said mole ratio of said bicarbonate anions to said carbon dioxide fall in within said range, and
(b) the total quantity of all bicarbonate anions remains within a value such that said mole ratio of said bicarbonate anions in said solution to said carbon dioxide falls within said range, and
(c) the total individual quantities of said respective carboxylic acids is such that said mole ratio of l-lactate to pyruvate, and said mole ratio of d-betahydroxybutyrate to acetoacetate each remain within said respective ranges.

* * * * *